United States Patent [19]

Bundy

[11] E Re. 30,053

[45] Reissued Jul. 24, 1979

[54] PG-TYPE, 1,9-LACTONES

[75] Inventor: Gordon L. Bundy, Kalamazoo, Mich.

[73] Assignee: The Upjohn Company, Kalamazoo, Mich.

[21] Appl. No.: 869,900

[22] Filed: Jan. 16, 1978

Related U.S. Patent Documents

Reissue of:

[64] Patent No.: 4,049,648
Issued: Sep. 20, 1977
Appl. No.: 670,522
Filed: Mar. 29, 1976

U.S. Applications:

[63] Continuation-in-part of Ser. No. 589,724, Jun. 23, 1975, abandoned.

[51] Int. Cl.[2] ..... C07D 313/00

[52] U.S. Cl. ..... 542/426; 260/340.2; 260/343.41; 260/448.8 R; 260/514 D; 424/279; 542/429; 562/503

[58] Field of Search ..... 260/343.2 F, 340.2, 260/240 R, 343.41; 542/426, 429

[56] References Cited

U.S. PATENT DOCUMENTS

| | | | |
|---|---|---|---|
| 3,864,387 | 2/1975 | Nelson | 560/60 |
| 3,935,240 | 1/1976 | Mallion | 260/469 |

FOREIGN PATENT DOCUMENTS

| | | | |
|---|---|---|---|
| 50-13385 | 2/1975 | Japan | 260/343.41 |

OTHER PUBLICATIONS

Corey, J.A.C.S. 97, p. 653, 1975.

*Primary Examiner*—John M. Ford
*Assistant Examiner*—Jane T. Fan
*Attorney, Agent, or Firm*—Robert A. Armitage

[57] ABSTRACT

The present invention provides novel 1,9 lactones of prostaglandin-type free acids and a process for their preparation. These lactones are useful for the same pharmacological purposes as the corresponding prostaglandin-type free acids.

113 Claims, No Drawings

PG-TYPE, 1,9-LACTONES

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation-in-part of copending application Ser. No. 589,724, filed June 23, 1975, now abandaned.

BACKGROUND OF THE INVENTION

This invention provides novel compositions of matter.

Particularly this invention provides novel lactones of some of the known prostaglandins or prostaglandin analogs.

The known prostaglandins include the PGE compounds, e.g. prostaglandin $E_1$ ($PGE_1$), prostaglandin $E_2$ ($PGE_2$), prostaglandin $E_3$ ($PGE_3$), and dihydroprostaglandin $E_1$ (dihydro-$PGE_1$).

The known prostaglandins include $PGF_\alpha$ compounds, e.g. prostaglandin $F_{1\alpha}$ ($PGF_{1\alpha}$), prostaglandin $F_{2\alpha}$ ($PGF_{2\alpha}$), prostaglandin $F_{3\alpha}$ ($PGF_{3\alpha}$), and dihydroprostaglandin $F_{1\alpha}$ (dihydro-$PGF_{1\alpha}$).

The known prostaglandins include $PGF_\beta$ compounds, e.g. prostaglandin $F_{1\beta}$ ($PGF_{1\beta}$), prostaglandin $F_{2\beta}$ ($PGE_{2\beta}$), prostaglandin $F_{3\beta}$ ($PGE_{3\beta}$), and dihydroprostaglandin $F_{1\beta}$ (dihydro-$PGF_{1\beta}$).

The known prostaglandins include PGA compounds, e.g. prostaglandin $A_1$ ($PGA_1$), prostaglandin $A_2$ ($PGA_2$), prostaglandin $A_3$ ($PGA_3$), and dihydroprostaglandin $A_1$ (dihydro-$PGA_1$).

The known prostaglandins include PGB compounds, e.g. prostaglandin $B_1$ ($PGB_1$), prostaglandin $B_2$ ($PGB_2$), prostaglandin $B_3$ ($PGB_3$), and dihydroprostaglandin $B_1$ (dihydro-$PGB_1$).

Each of the above mentioned known prostaglandins (PG's) is a derivative of prostanoic acic which has the following structure and carbon atom numbering

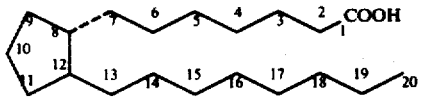

See, for example, Bergstrom et al., Pharmacol. Rev. 20, 1 (1968), and references cited therein. A systematic name for prostanoic acid is 7-[(2β-octyl)-cyclopent-1α-yl]heptanoic acid.

$PGE_1$ has the following structure:

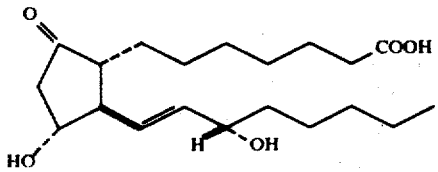

$PGE_2$ has the following structure:

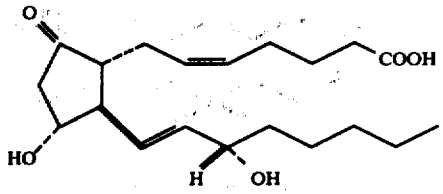

$PGE_3$ has the following structure:

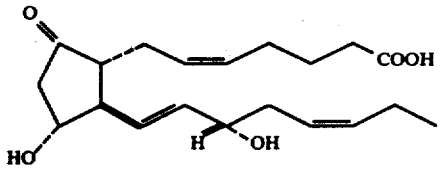

Dihydro-$PGE_1$ has the following structure:

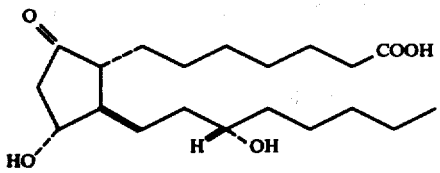

$PGF_{1\alpha}$ has the following structure:

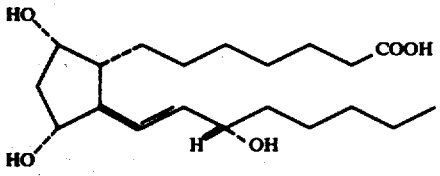

$PGF_{2\alpha}$ has the following structure:

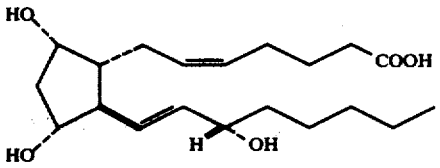

$PGF_{3\alpha}$ has the following structure:

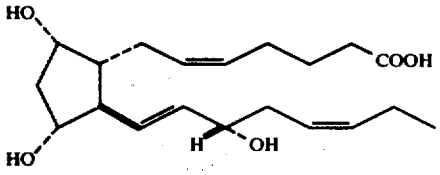

Dihydro-$PGF_{1\alpha}$ has the following structure:

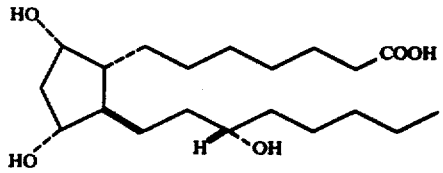

$PGF_{1\beta}$ has the following structure:

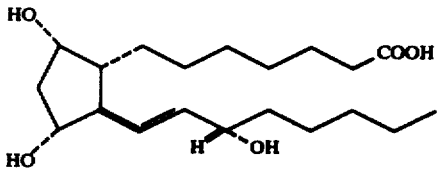

$PGF_{2\beta}$ has the following structure:

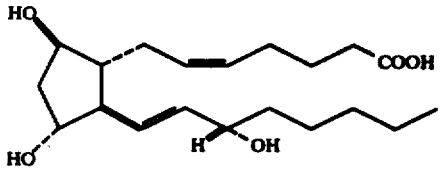

$PGF_{3\beta}$ has the following structure:

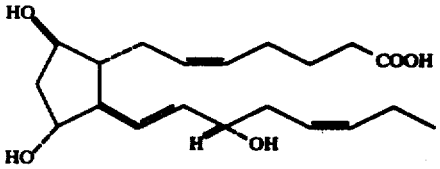

Dihydro-$PGF_{1\beta}$ has the following structure:

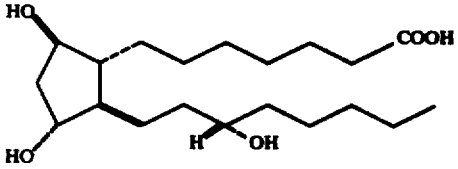

$PGA_1$ has the following structure:

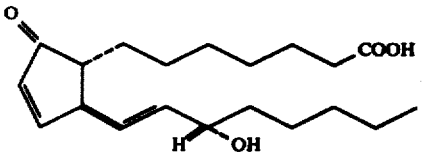

$PGA_2$ has the following structure:

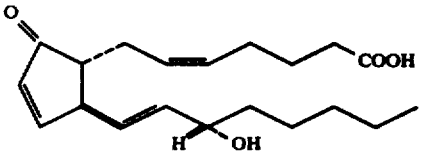

$PGA_3$ has the following structure:

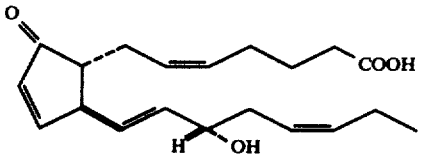

Dihydro-$PGA_1$ has the following structure:

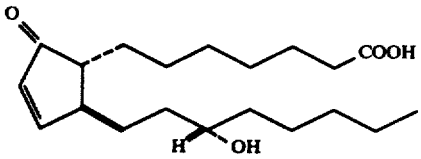

$PGB_1$ has the following structure:

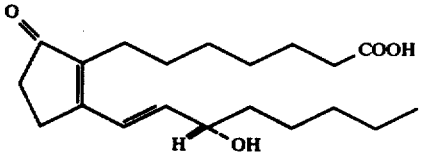

$PGB_2$ has the following structure:

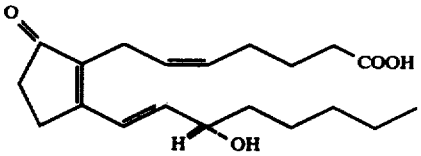

$PGB_3$ has the following structure:

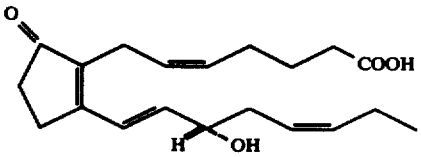

Dihydro-$PGB_1$ has the following structure:

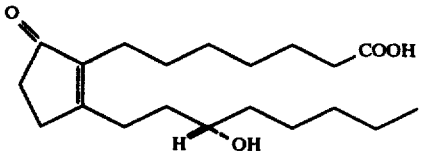

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (~) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins.

Expressions such as C-9, C-11, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin.

For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins is intended, the word "racemic" or "dl" will precede the prostaglandin name.

The term "prostaglandin-type" (PG-type) compound, as used herein, refers to any cyclopentane derivative herein which is useful for at least one of the same pharmacological purposes as the prostaglandins, as indicated herein.

The term prostaglandin-type intermediate, as used herein, refers to any cyclopentane derivative useful in preparing a prostaglandin-type compound.

The formulas, as drawn herein, which depict a prostaglandin-type compound or an intermediate useful in preparing a prostaglandin-type compound, each represent the particular stereoisomer of the prostaglandin-type compound which is of the same relative stereochemical configuration as a corresponding prostaglandin obtained from mammalian tissues, or the particular stereoisomer of the intermediate which is useful in preparing the above stereoisomer of the prostaglandin-type compounds.

The term "prostaglandin analog", as used herein, represents that stereoisomer of a prostaglandin-type compound which is of the same relative stereochemical configuration as a corresponding prostaglandin obtained from mammalian tissues, a mixture comprising that stereoisomer and the enantiomer thereof, or the enantiomer thereof. In particular, where a formula is used to depict a prostaglandin- type compound herein, the term prostaglandin analog refers to the compound of that formula, or a mixture comprising that compound and the enantiomer thereof.

The term "prostaglandin-type lactone" as used herein refers to a 1,9-; 1,11-; or 1,15-lactone of a prostaglandin or prostaglandin analog, but only to the extent that the C-9, C-11, or C-15 position, respectively, is hydroxylated and thus capable of lactone formation with the PG carboxyl. For example, as applied to a PGE-type compound (e.g. $PGE_2$) the term "prostaglandin-type lactone" refers only to a 1,11- or 1,15-lactone. Further, where a formula is used to depict a prostaglandin-type lactone herein, or a prostaglandin analog from which the prostaglandin-type lactone is prepared, the term "prostaglandin-type lactone" refers to the compound of that formula (or the lactone prepared therefrom) or a mixture comprising that compound (or the lactone prepared therefrom) and the enantiomer thereof.

The various PG's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

a. stimulating smooth muscle (as shown by tests, for example, on guinea pig ileum, rabbit duodenum, or qerbil colon);
b. affecting lipolytic activity (as shown by antagonism of epinephrine induced release of glycerol from isolated rat fat pads);
c. inhibiting gastric secretion and reducing undesirable gastrointestinal effects from systematic administration of prostaglandin synthetase inhibitors;
d. controlling spasm and facilitating breathing in asthmatic conditions;
e. decongesting nasal passages;
f. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);
g. affecting the reproductive organs of mammals as labor inducers, abortifacients, cervical dilators, regulators of the estrus, and regulators of the menstrual cycle; and
h. accelerating growth of epidermal cells and keratin in animals.

For the $PGF_\alpha$ compound these biological responses include:

a. stimulating smooth muscle (as shown by tests on guinea pig ileum, rabbit duodenum, or gerbil colon);
b. inhibiting gastric secretion and reducing undesirable gastrointestinal effects from systemic administration of prostaglandin synthetase inhibitors;
c. decongesting nasal passages;
d. decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and
e. affecting the reproductive organs of mammals as labor inducers, abortifacients, cervical dilators, regulators of the estrus, and regulators of the menstral cycle.

For the $PGF_\beta$ compounds these biological response include:

a. stimulating smooth muscle (as shown by tests on guinea pig ileum, rabbit duodenum, or gerbil colon);
b. inhibiting gastric secretion and reducing undesirable gastrointestinal effects from systematic administration of prostaglandin synthetase inhibitors;
c. controlling spasm and facilitating breathing in asthmatic conditions;
d. decongesting nasal passages;
e. decreasing blood platelet adhesion (as shown by platelet to glass adhesiveness) and inhibiting blood platelet aggregation and thrombis formation induced by various physical stimuli (e.g., arterial injury) or chemical stimuli (e.g., ADP, ATP, serotinin, thrombin, and collagen); and f. affecting the reproductive organs of mammals as labor inducers, abortifacients, cervical dilators, regulators of the estrus, and regulators of the menstrual cycle.

For the PGA compounds these biological responses include:

a. stimulating smooth muscle (as shown by tests on quinea pig ileum, rabbit duodenum, or gerbil colon);
b. inhibiting gastric secretion and reducing undesirable gastrointestinal effects from systematic administration of prostaglandin synthetase inhibitors;
d. controlling spasm and facilitating breathing in asthmatic conditions;
d. decongesting nasal passages; and
e. increasing kidney blood flow.

For the PGB compounds these biological responses include:

a. stimulating smooth muscle (as shown by tests on guinea pig ileum, rabbit duodenum, or gerbil colon); and
b. accelerating growth of epidermal cells and keratin in animals.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination wth less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g. diabetes mellitus, vascular diseases, and hyperthyroidism.

The prostaglandins so cited above as useful in mammals, including man and certain useful animals, e.g., dogs and pigs, to reduce and control excessive gastric secetion, therby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-flammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex, and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.1 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimerics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose, in a dose range of about 10 μg. to about 10 mg. per ml. of a pharmacologically suitable liquid vehicle or as an aerosol spray, both for topical application.

The prostaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injections at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration in advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg. per ml. of the prostaglandin pound. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

In addition to the discovery of the prostaglandins cited above, various prostaglandin analogs have likewise been discovered. In particular, there are known prostaglandin analogs of the formula

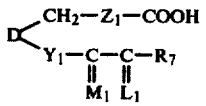

I wherein D is

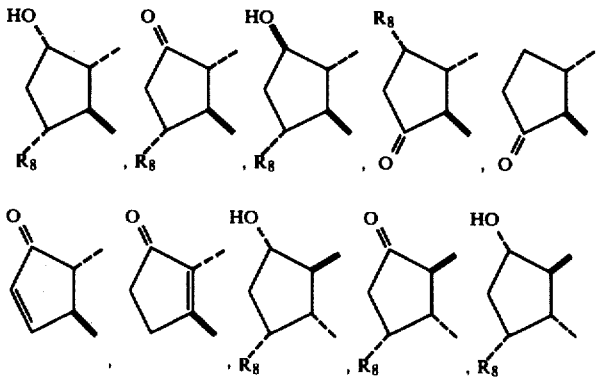

-continued

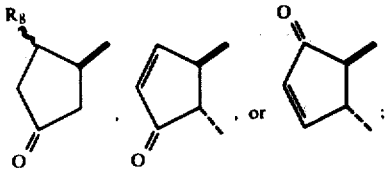

wherein $R_8$ is hydrogen or hydroxy;

wherein $L_1$ is

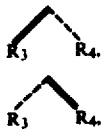

or a mixture of

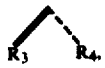

and

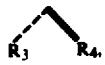

wherein $R_3$ and $R_4$ are hydrogen, methyl, or fluoro, being the same or different, with the proviso that one of $R_3$ and $R_4$ is fluoro, only when the other is hydrogen or fluoro;

wherein $M_1$ is

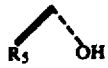

or

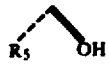

wherein $R_5$ is hydrogen or methyl;

wherein $R_7$ is $-(CH_2)_m-CH_3$, wherein $m$ is one to 5, inclusive, cis—CH=CH—$CH_2$—$CH_3$, or

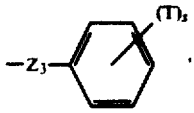

wherein T is chloro, fluoro, trifluoromethyl, alkyl of one to 3 carbon atoms, inclusive, or alkoxy of one to 3 carbon atoms, inclusive, the various T's being the same or different, s is zero, one, 2, or 3, and $Z_3$ is oxa or methylene, with the proviso that not more than two T's are other than alkyl, and the further proviso that $Z_3$ is oxa only when $R_3$ and $R_4$ are hydrogen or methyl, being the same or different;

wherein $Y_1$ is trans—CH=CH—, —$CH_2CH_2$—, cis—CH=CH—, or —C≡C—; and wherein $Z_1$ is cis—CH=CH—$CH_2$—$(CH_2)_g$—$CH_2$—, (1)

cis—CH=CH—$CH_2$—$(CH_2)_g$—$CF_2$—, (2)

cis—$CH_2$—CH=CH—$(CH_2)_g$—$CH_2$—, (3)

—$(CH_2)_3$—$(CH_2)_g$—$CH_2$—, (4)

—$(CH_2)_3$—$(CH_2)_g$—$CF_2$—, (5)

—$CH_2$—O—$CH_2$—$(CH_2)_g$—$CH_2$—, (6)

(7)

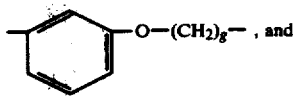

, and (8)

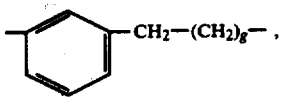

wherein g is one, 2, or 3.

While the use and preparation of many of the prostaglandin analogs described above is widely known in the art, the Appendix, hereto provides a discussion of the preparation of each of the various compounds depicted by formula I above.

For the prostaglandin analogs described in formula I above, a convenient classification system according to cyclopentane ring structure is effected by referencing:

a. $PGF_\alpha$-type compounds when D is

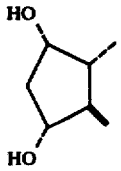

b. 11-deoxy-$PGF_\alpha$-type compounds when D is

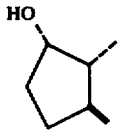

c. PGE-type compounds when D is

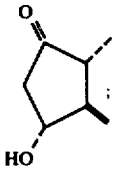

d. 11-deoxy-PGE-type compounds when D is

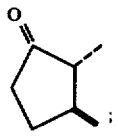

e. PGF$_\beta$-type compounds when D is

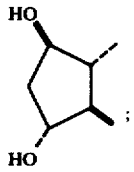

f. PGD-type or 9$\beta$-PGD-type compounds when D is

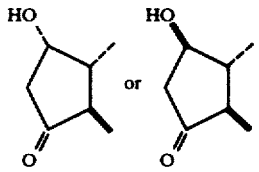

and g. 9-deoxy-PGD-type compounds when D is

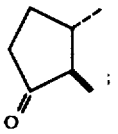

h. 9-deoxy-9,10-didehydro-PGD-type compounds when D is

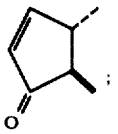

and i. PGA-type compounds when D is

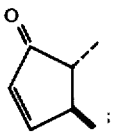

j. PGB-type compounds when D is

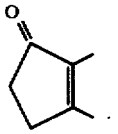

k. 8$\beta$,12$\alpha$-PGF$_\alpha$-type compounds when D is

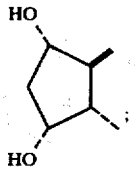

l. 8$\beta$,12$\alpha$-11-deoxy-PGF$_\alpha$-type compounds when D is

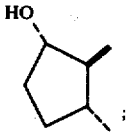

m. 8$\beta$,12$\alpha$-PGE-type compounds when D is

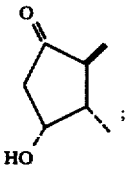

n. 8$\beta$,12$\alpha$-11-deoxy-PGE-type compounds when D is

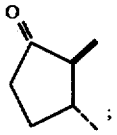

o. 8$\beta$,12$\alpha$-PGF$_\beta$-type compounds when D is

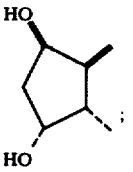

p. 8$\beta$,12$\alpha$-PGD-type or 8$\beta$,9$\beta$,12$\alpha$-PGD-type compounds when D is

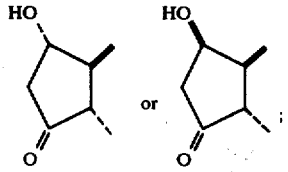

q. 8$\beta$,12$\alpha$-9-deoxy-PGD-type compounds when D is

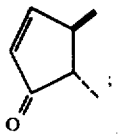

and s. 8β,12α-PGA-type compounds when D is

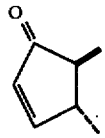

Those prostaglandin analogs wherein $Z_1$ is cis—CH=CH—$CH_2$—$(CH_2)$—$CH_2$— or cis—CH=CH—$CH_2$—$(CH_2)_g$—$CF_2$— are named as "$PG_2$" compounds. The latter compounds are further characterized as "2,2-difluoro" $PG_2$-type compounds. When g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in $PGE_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —$(CH_2)_3$—$(CH_2)_g$—$CH_2$— or —$(CH_2)_3$—$(CH_2)_g$—$CF_2$, wherein g is as defined above, the PG analogs so described are "$PG_1$" compounds. When g is 2 or 3, the "2a-homo" and "2a, 2b-dihomo" compounds are described as is discussed in the preceding paragraph.

When $Z_1$ is —$CH_2$—O—$CH_2$—$(CH_2)_g$—$CH_2$— the PG analogs so described are named as "5-oxa-$PG_1$" compounds. When *g* is 2 or 3, the compounds so described are "2a-homo" or "2a, 2b-dihomo" compounds, respectively, as discussed above.

When $Z_1$ is cis—$CH_2$—CH=CH—$(CH_2)_g$—$CH_2$—, wherein g is as defined above, the PG analogs so described are named "cis-4,5-didehydro-$PG_1$" compounds. When g is 2 or 3, the compounds so described are further characterized as "2a-homo" or "2a,2b-dihomo" compounds, respectively, as discussed above.

For the PG analogs wherein $Z_1$ is

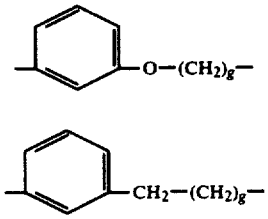

there are described, respectively, 3-oxa-3,7-inter-m-phenylene-4,5,6-trinor or 3,7-inter-m-phenylene-4,5,6-trinor-PG-type compounds, when *g* is one. When *g* is 2 or 3, the above compounds are additionally described as "2a-homo" or "2a,2b-dihomo" PG-type compounds, respectively.

The prostaglandin analogs described herein which contain a cis—CH=CH— moiety at the C-13 to C-14, the compounds so described are "13-cis" compounds.

Further when the C-13 to C-14 moiety is —C≡C— or —$CH_2CH_2$— the compounds so described are named as "13,14-didehydro" or "13,14-dihydro" compounds, respectively.

When $R_7$ is —$(CH_2)_m$—$CH_3$, wherein m is as defined above, the PG analogs so described are named as "19,20-dinor", "20-nor", "20-methyl", or "20-ethyl" compounds when m is one, 2,4, or 5, respectively. When $R_7$ is

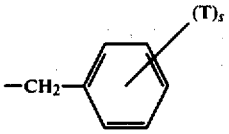

wherein T and s are as defined above, the PG analogs so described are named as "17-phenyl-18,19,20-trinor" compounds, when s is 0. When s is one, 2, or 3, the corresponding compounds are named as "17-(substituted phenyl)-18,19,20-trinor" compounds.

When $R_7$ is

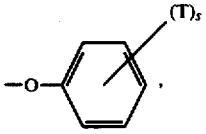

wherein T and s are as defined above, and neither $R_3$ nor $R_4$ is methyl, the PG analogs so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy or 16-(substituted phenoxy)-18,19,20-trinor" compounds, respectively.

When $R_7$ is cis—CH=CH—$CH_2$—$CH_3$, the compounds so described are "$PG_3$" or "cis-17,18-didehydro" compounds depending on whether $Z_1$ is cis—CH=CH—$(CH_2)_g$—$C(R_2)_2$, wherein $R_2$ is hydrogen or fluoro, or another moiety, respectively.

When at least one of $R_3$ and $R_4$ is not hydrogen then (except for the 16-phenoxy compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $R_5$ is methyl, the compounds so described are named as "15-methyl" compounds.

Some formulas of 13-cis-cyclopentane derivatives described hereinafter contain a moiety of the formula:

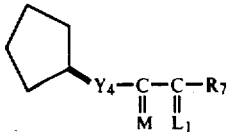

wherein the cyclopentane ring is variously substituted, wherein M is variously defined according to the subscripts provided herein; wherein $L_1$ and $R_7$ are as defined above; and wherein $Y_4$ is cis—CH=CH—. Optionally the above formula is depicted with one or both of $L_1$ and M above the carbon atom to which it is attached, e.g., as follows:

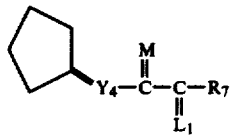

When either of the above representations is employed, it is hereby defined to indicate the following convention with respect to the representation of the cis-13 double bond:

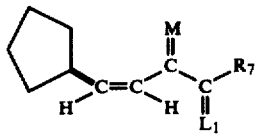

Further in employing this convention when M is, for example,

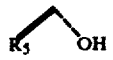

or

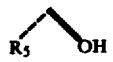

then the corresponding representations:

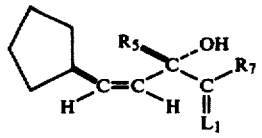

or

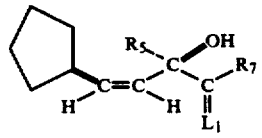

are intended, respectively. Accordingly all the formulas herein which represent 13-cis cyclopentane derivatives are depicted by the same convention as that for the cis-13-$PGE_1$ when drawn as follows:

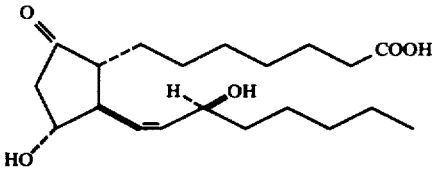

Thus, by this convention the (15S)-hydroxy of cis-13-$PGE_1$ is in the beta configuration.

cis-13-PG-type compounds as drawn herein which have an hydroxy or methoxy at C-15 in the alpha configuration are of the opposite relative stereochemical configuration at C-15 as that of cis-13-$PGE_1$, and are therefore named as "15-epi" compounds. When the beta hydroxy or methoxy configuration is present, no special designation of this stereochemistry is provided.

Accordingly, 15-epi-16,16-difluoro-cis-13-$PGD_2$ is depicted herein as follows:

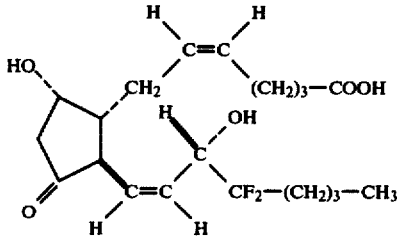

Alternate representations of cis-13-$PGE_1$ affect the depiction of C-15 as an alpha or beta hydroxy. Thus, by a representation contrary to the instant convention, cis-13-$PGE_1$ appears as follows:

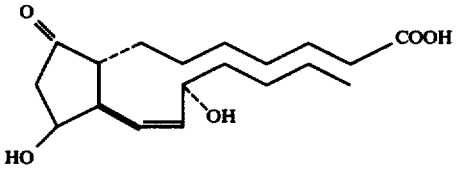

Accordingly, care must be taken to consistently draw the formulas of cis-13-PG-type compounds herein such that the C-15 carbon atoms is properly represented, i.e., all cis-13-15-epic-PG's are of the 15α-hydroxy configuration.

13,14-trans-13,14-dihydro, or 13,14-didehydro cyclopentane derivatives which contain the moiety

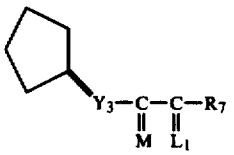

wherein the cyclopentane ring is variously substituted, wherein M is variously defined according to the subscripts provided herein; wherein $L_1$ and $R_7$ are as defined above; and wherein $Y_3$ is trans—CH=CH—, —$CH_2CH_2$—, or —C≡C— respectively. When this representation is employed, it is hereby defined to indicate the following convention with respect to the representation of the C-13 to C-14 moiety:

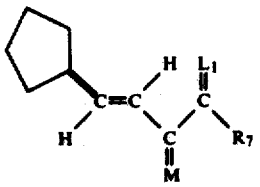

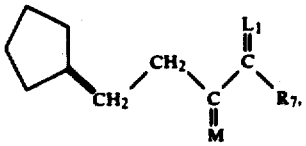

or

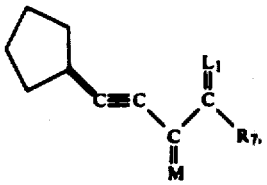

respectively. Likewise in employing this convention when M is, for example

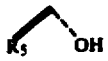

or

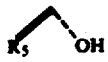

then the corresponding representation for the trans-13 compounds:

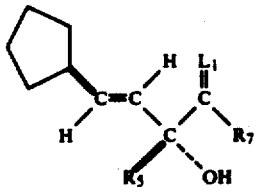

or

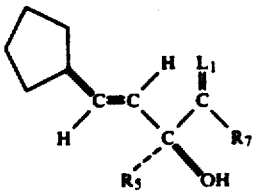

the 13,14-dihydro compounds:

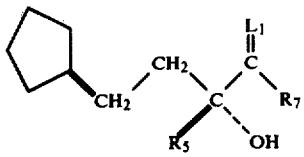

or

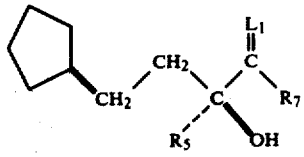

and the 13,14-didehydro compounds:

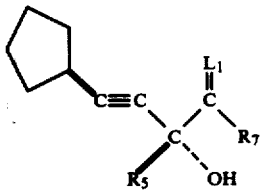

or

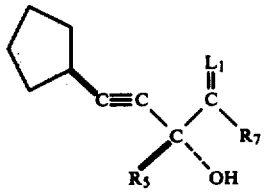

are intended, respectively. Accordingly all the formulas herein which represent trans-13, 13,14-dihydro, or 13,14-didehydro-cyclopentane derivatives are depicted by the same convention as that for $PGE_1$ when drawn as above, i.e.,

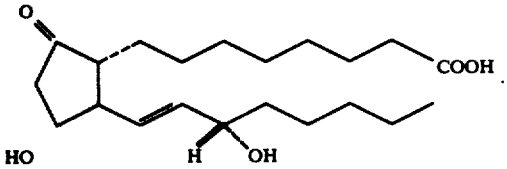

Thus, for all trans-13, 13,14-dihydro, or 13,14-didehydro-PG-type compounds, as drawn herein the 15α-hydroxy configuration corresponds to the relative C-15 stereochemical configuration of $PGE_1$ as obtained from mammalian tissues. No special designation of the C-15 stereochemistry is provided in naming these compounds. For compounds of the opposite stereochemical configuration at C-15 (i.e., 15β-hydroxy), the description "15-epi" will be employed.

The prostaglandin analogs of formula I are known to correspond to the prostaglandins described above, in that these prostaglandin analogs exhibit prostaglandin-like activity.

Specifically the PGE-, 8β,12α-PGE-, 8β,12α-11-deoxy-PGE-, and 11-deoxy-PGE-type compounds correspond to the PGE compounds described above, in that these PGE-, 8β,12α-PGE-, 8β,12α-11-deoxy-PGE-, and 11-deoxy-PGE-type compounds are useful for each of the above-described purposes for which the PGE compounds are used, and are used in the same manner as the PGE compounds, as described above.

The $PGF_\alpha$-, 8β,12α-$PGF_\alpha$-, 8β,12α-11-deoxy-$PGF_\alpha$-, and 11-deoxy-$PGF_\alpha$-type compounds correspond to the $PGF_\alpha$compounds described above, in that these $PGF_{60}$ -, 8β,12α-$PGF_\alpha$, 8β,12α-11-deoxy-$PGF_\alpha$-, and 11-deoxy-$PGF_\alpha$-type compounds are useful for each of the above-described purposes for which the $PGF_\alpha$ compounds are used, and are used in the same manner as the PGF compounds, as described above.

The PGD-, 9β-PGD-, 8β,12α-PGD-, 8β,9β,12α-PGD-, 9-deoxy-PGD-, 8β,12α-9-deoxy-PGD-, 8β,12α-9,10-didehydro-9-deoxy-PGD-, and 9,10-didehydro-9-deoxy-PGD-type compounds of formula I correspond to the PGE or $PGF_\alpha$ compounds described above, in that these PGD-, 8β,12α-PGD-, 9-deoxy-PGD-, 8β,12α-9-deoxy-PGD-, 8β,12α-9-deoxy-9,10-didehydro-PGD-, or 9-deoxy-9,10-didehydro-PGD-type compounds are useful for each of the above-described purposes for which either the PGE or $PGF_\alpha$ compounds are used, and are used in the same manner as the PGE and PGFα compounds, as described above.

The PGA- or 8β,12α-PGA-type compounds of formula I correspond to the PGA compounds described above, in that these PGA- or 8β,12α-PGA-type compounds are useful for each of the above described purposes for which the PGA compounds are used, and are used in the same manner as the PGA compounds, as described above. The PGB-type compounds of formula I correspond to the PGB compounds described above in that the PGB compounds are useful for each of the above described purposes for which PGB compounds are used, and are used in the same manner as the PGB compounds described above.

The prostaglandins described above, ar all known to be potent in causing multiple biological responses even at low doses. Moreover, for many applications, there prostaglandins are known to exhibit a relatively short duration of biological activity. Significantly, the prostaglandin analogs of formula I are known to be substantially more selective with regard to potency in causing prostaglandin-like biological responses, and have a somewhat longer duration of biological activity. Thus, each of these prostaglandin analogs is known to be equally or even more useful than one of the corresponding prostaglandins described above for at least one of the pharmacological purposes indicated above for the latter.

Another property of the prostaglandin analogs of formula I, compared with the corresponding prostaglandins, is that these PG analogs are known to be capable of effective administration orally, sublingually, intravaginally, buccally, or rectally in many cases where the corresponding prostaglandin is known to be effective only by the intravenous, intramuscular, or subcutaneous injection or infusion methods of administration indicated above as used of these prostaglandins. When alternate routes of administration are employed, they are known to facilitate maintaining unilevels of these compounds in the body with fewer, shorter, or smaller doses, and to make possible self-administration by the patient.

Accordingly, the prostaglandin analogs of formula I are known to be capable of administration in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are known to be preferred. For subcutaneous or intramuscular injection, sterile solutions or suspensions are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, the use of sterile tablets or silicone rubber capsules or other objects containing or impregnated with the substance is known.

Methods for the preparation of large ringed lactones are known in the art. See, for example, E. J. Corey, et al., Journal of the American Chemical Society 96: 5614 (1974). Further, certain 1,9 lactones of cyclopentane containing carboxylic acids are known in the art. See Sourth African Application No. 737,357, Derwent Farmdoc CPI No. 28414V, which discloses 1,9-lactones of μ-heterocyclic prostaglandin analogs; Japanese Application No. 50-0037-793, Derwent Farmdoc CPI No. 61147W, which discloses 15-deoxy-15-methyl-$PGF_{2\alpha}$, 1,9-lactone; and E. J. Corey, et al., Journal of the American Chemical Society 97: 653 (1975), which discloses $PGF_{2\alpha}$ 1,9-lactone. Further, the latter reference additionally discloses $PGF_{2\alpha}$, 1,15-lactone.

Finally, see Japanese Patent Application No. 50013-385, Derwent Farmdoc CPI No. 56267W, which discloses 1,9lactones of $PGF_{2\alpha}$ and (15RS)-15-methyl-$PGF_{2\alpha}$.

SUMMARY OF THE INVENTION

This invention provides novel bicyclic, cyclopentane-containing lactones.

This invention further provides novel processes for preparing these lactones.

In particular, this specification discloses:

1. a 1,9-, 1,11-, or 1,15-lactone of a prostaglandin analog of the formula

II

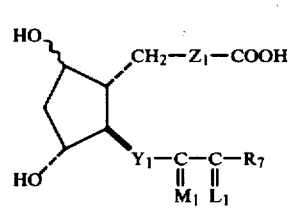

or

III

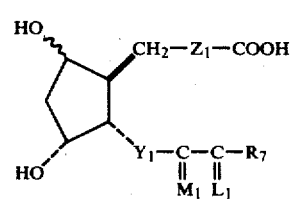

wherein $L_1$, $M_1$, $R_7$, $Y_1$, and $Z_1$ are as defined above;

2. a 1,9- or 1,15-lactone of a prostaglandin analog of the formula
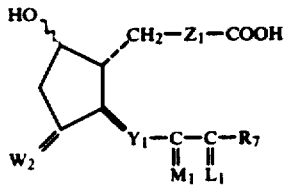
IV
or
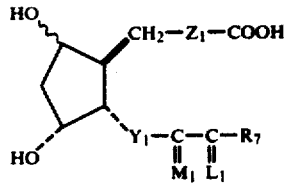
V
wherein $L_1$, $M_1$, $R_7$, $Y_1$, and $Z_1$ are as defined above; and
wherein $W_2$ is
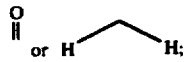
3. a 1,11 or 1,15-lactone of a prostaglandin analog of the formula
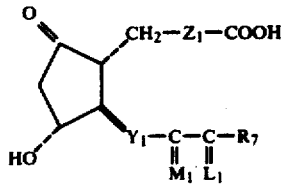
VI
or
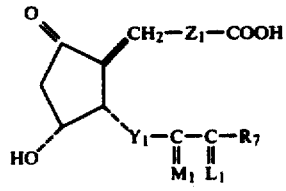
VII
wherein $L_1$, $M_1$, $R_7$, $Y_1$, and $Z_1$ are as defined above;
4. a 1,15-lactone of a prostaglandin analog of the
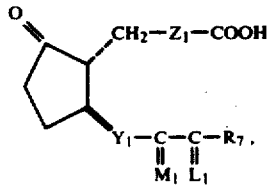
VIII
IX
-continued
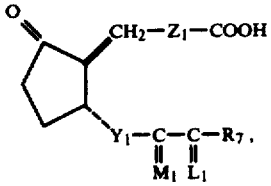
X
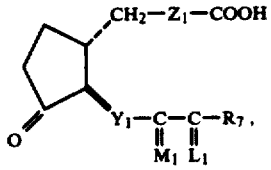
XI
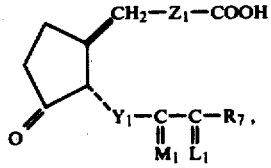
XII
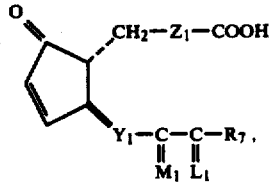
XIII
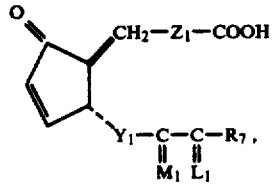
XIV
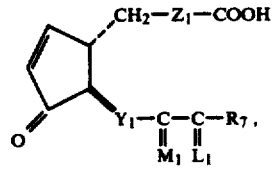
XV
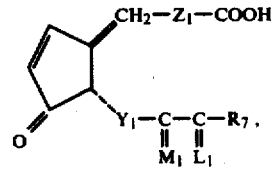
or
XVI -continued

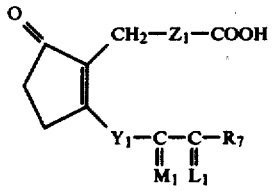

wherein $L_1$, $M_1$, $R_7$, $Y_1$, and $Z_1$ are as defined above.

The charts herein describe methods whereby the prostaglandins or prostaglandin analogs, hereinabove described, are transformed to 1,9-, 1,11-, or 1,15-lactones. Since each of these prostaglandins or prostaglandin analogs exhibits an hydroxyl at C-15, each is therefore capable of forming a 1,15-lactone. Further, 1,9- or 1,11-lactones of each of the prostaglandins or prostaglandin analogs hereinabove described is likewise capable of formation, depending upon whether the cyclopentane ring structure exhibits a 9-hydroxyl or an 11-hydroxyl, respectively. Thus, the PGA-, PGB-, 9-deoxy-PGD-, 9-deoxy-9,10-didehydro-PGD-, and 11-deoxy-PGE-type compounds or their 8β,12α-isomers are capable of forming only 1,15-lactones. The PGD-, 9β-PGD-, 11-deoxy-PGF$_\alpha$-, and 11-deoxy-PGFβ-type compounds or their 8β,12α-isomers are capable only of forming 1,9- or 1,15-lactones. The PGE-type compounds or their 8β,12α-isomers are capable of forming only 1,11- or 1,15-lactones. Finally, the PGF$_\alpha$- or PGF$_\beta$-type compounds or their 8β,12α-isomers are capable of forming 1,9-, 1,11-, or 1,15-lactones.

Chart A

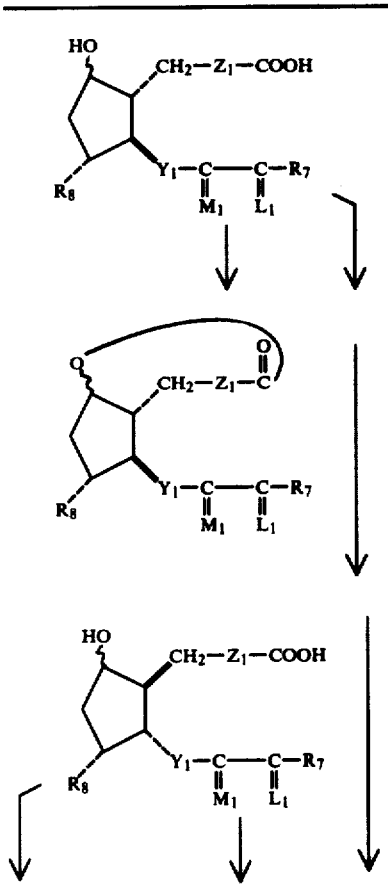

XXI

XXII

XXIII

XXIV

Chart A-continued

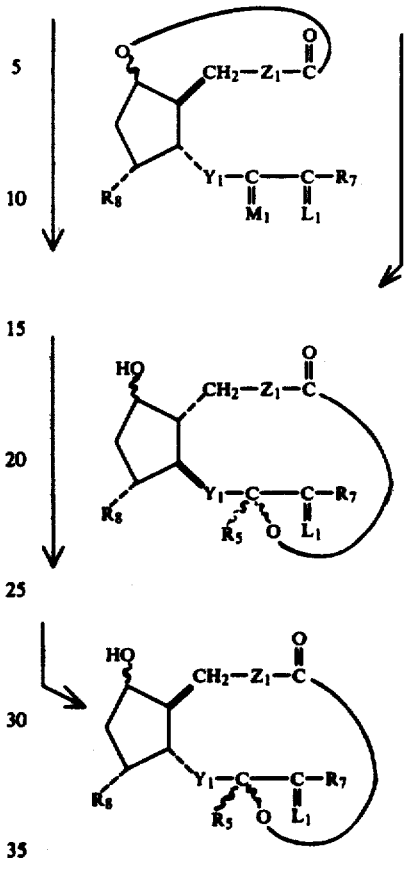

XXV

XXVI

Chart B

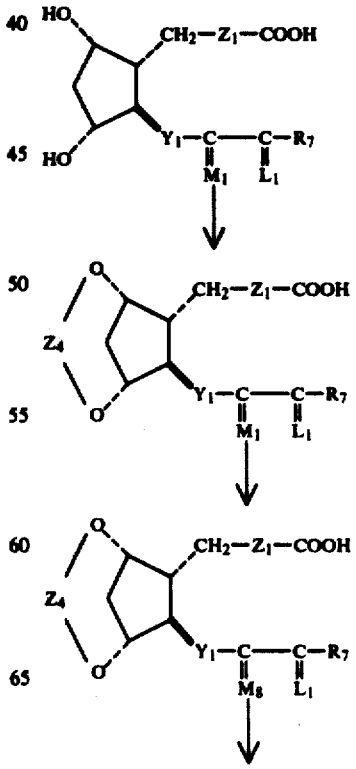

XXXI

XXXII

XXXIII

-continued
XXXIV
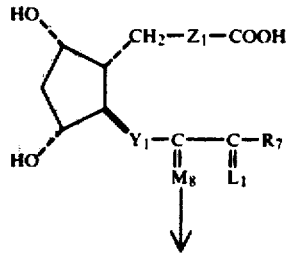
XXXV
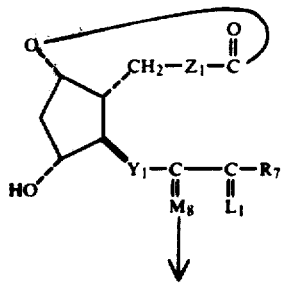
XXXVI
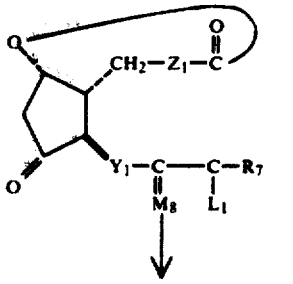
XXXVII
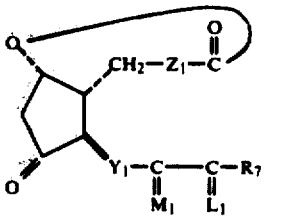
Chart C
XLI
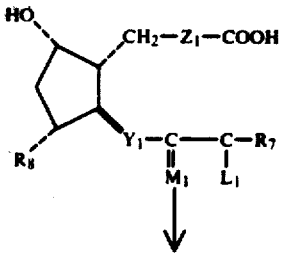
XLII
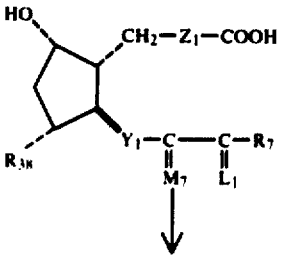
Chart C-continued
XLIII
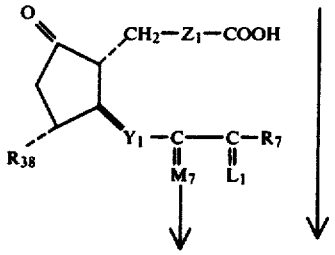
XLIV
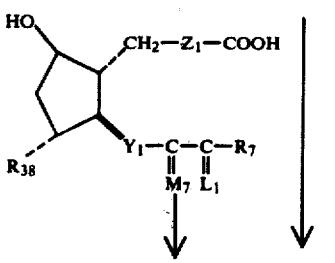
XLV
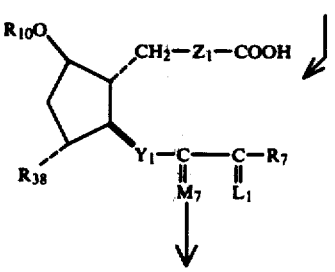
XLVI
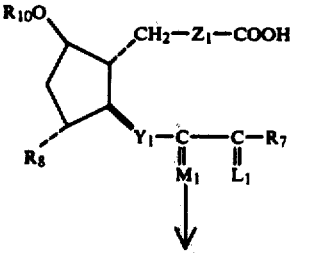
XLVII
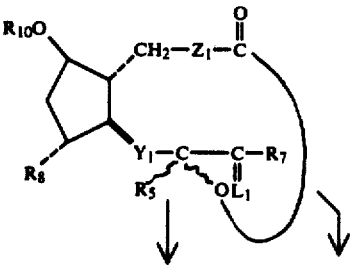
XLVIII
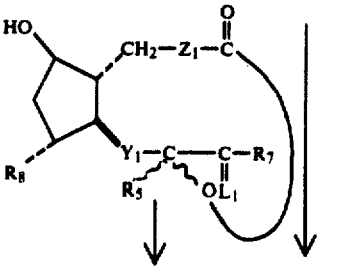

Chart C-continued
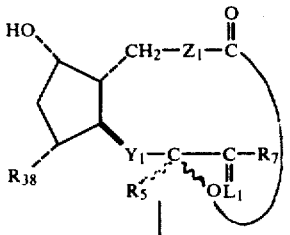
XLIX
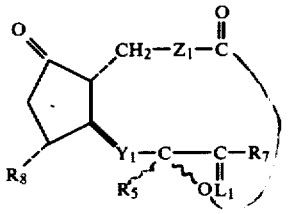
L
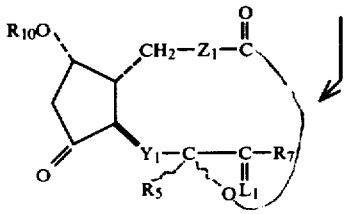
LI
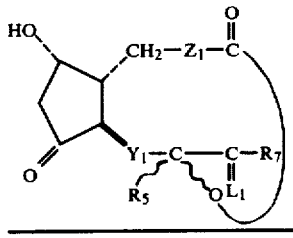
LII
Chart D
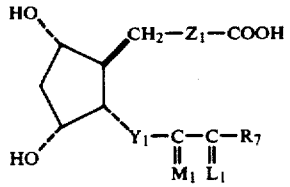
LXI
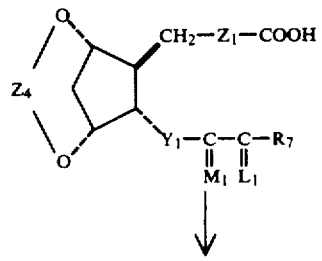
LXII
LXIII
Chart D-continued
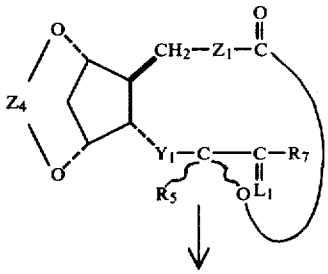
LXIV
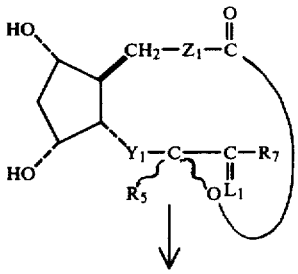
LXV
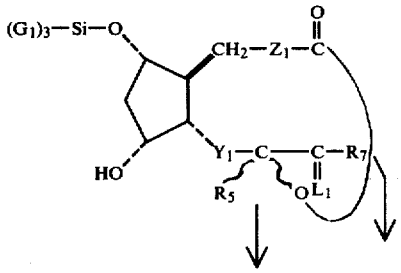
LXVI
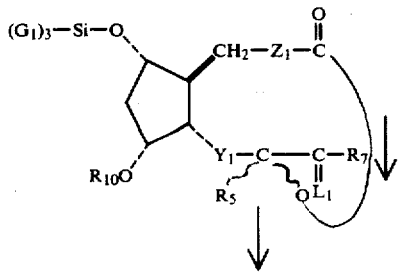
LXVII
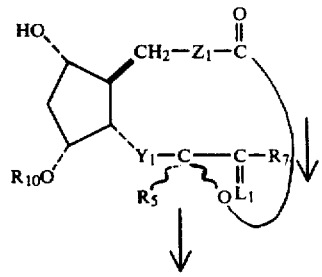
LXVIII Chart D-continued
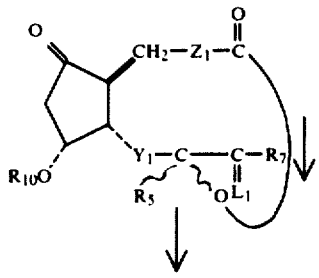
LXIX
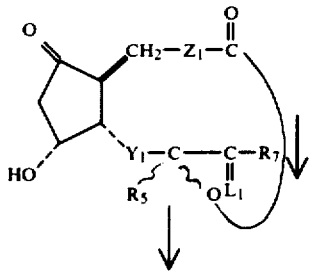
LXXI
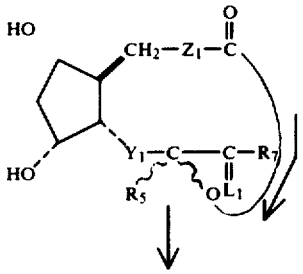
LXXII
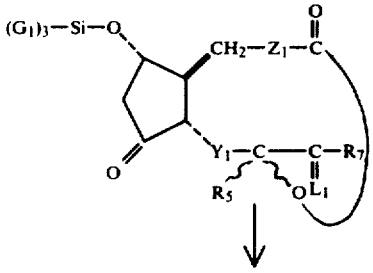
LXIII
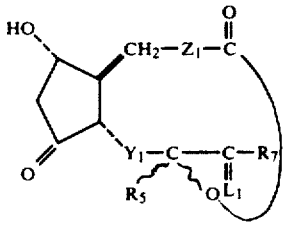
Chart E
LXXXI
Chart E-continued
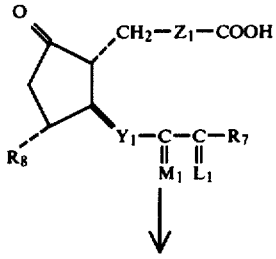
LXXXII
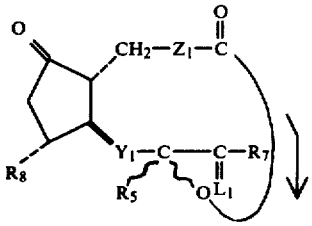
LXXXIII
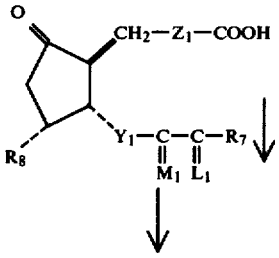
LXXXIV
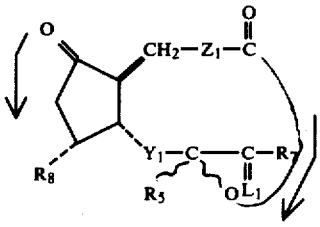
LXXXV
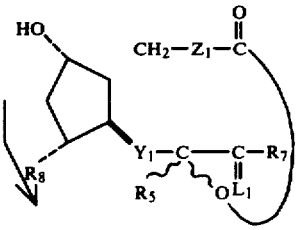
LXXXVI
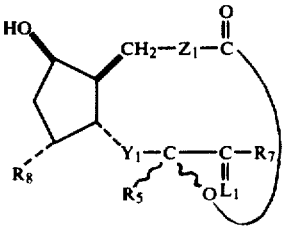

Chart F
XCI
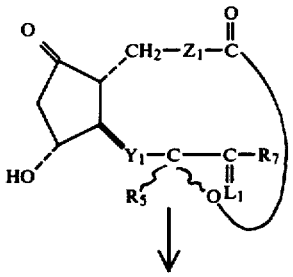
XCII
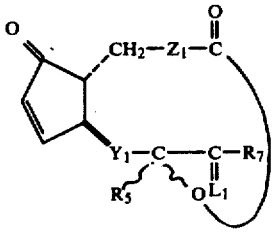
XCIII
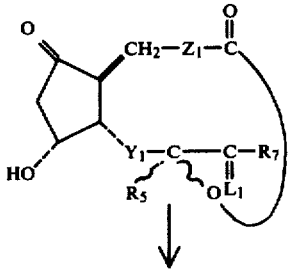
XCIV
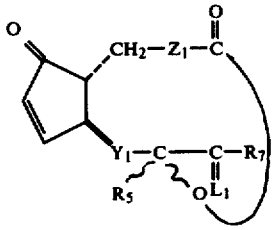
XCV
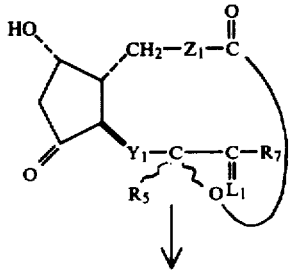
XCVI
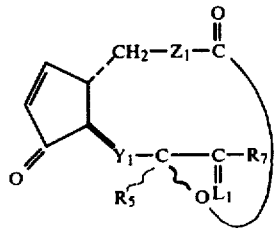
XCVII
Chart F-continued
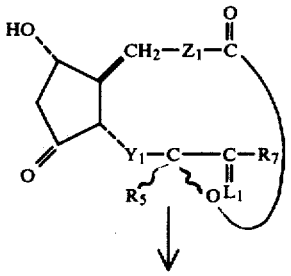
XCVIII
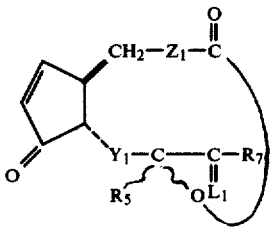
CHART G
CI
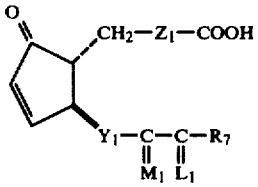
CII
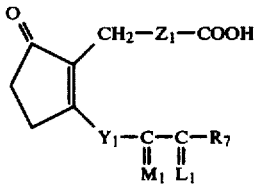
CV
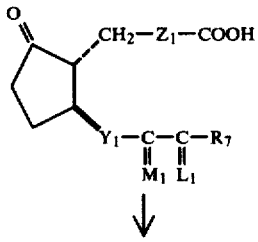
CVI
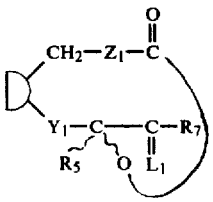

Chart H
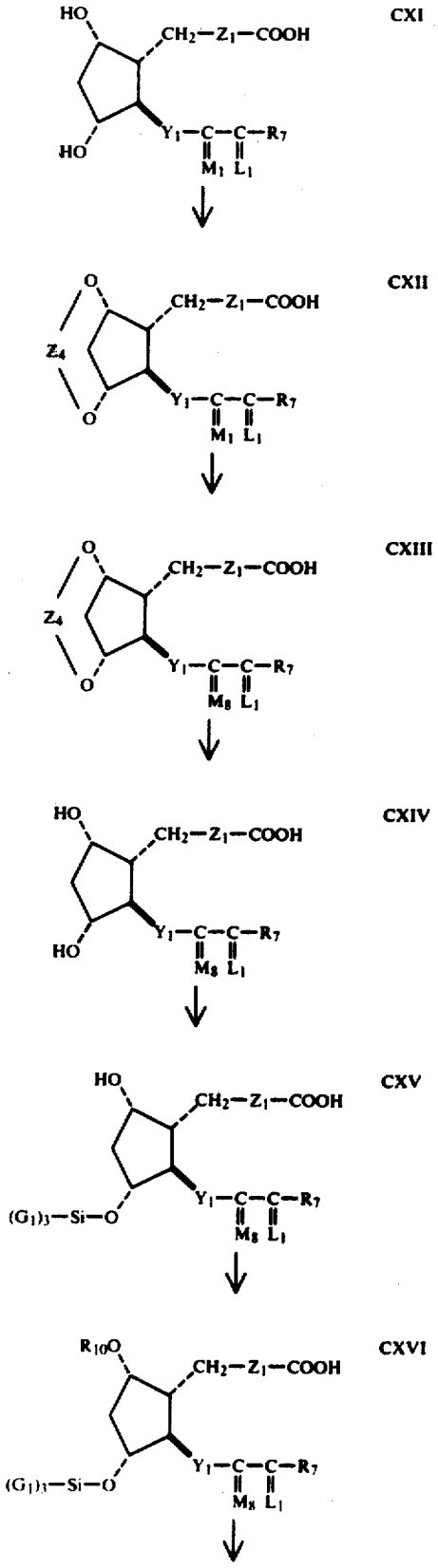
-continued
Chart H
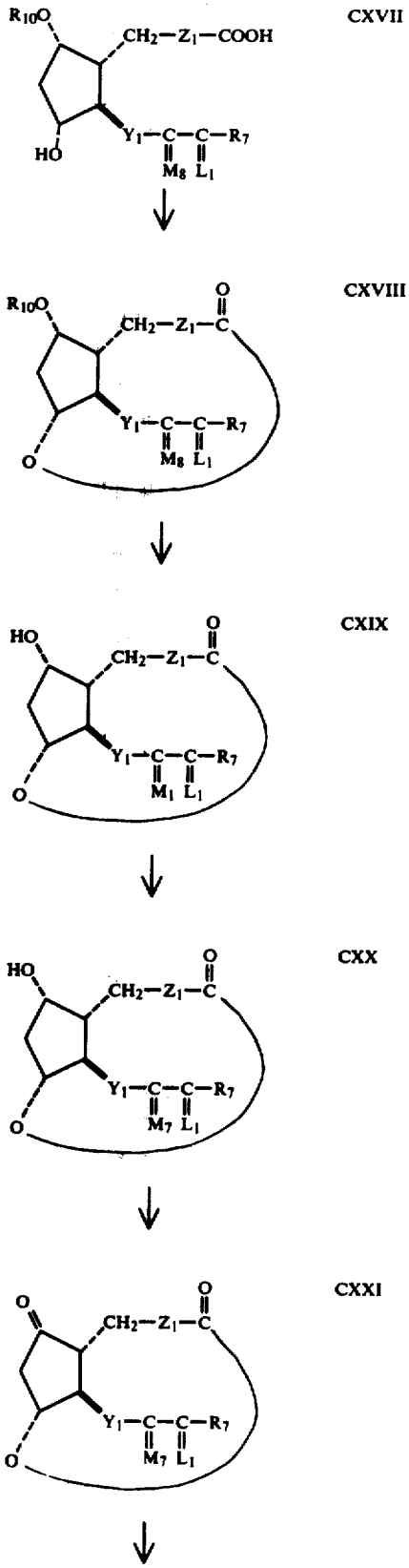

-continued
Chart H
CXXII
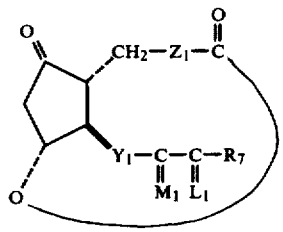
CXXIII
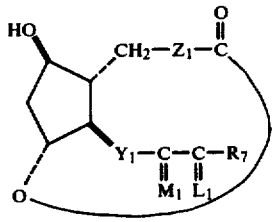
Chart J
CXXXI
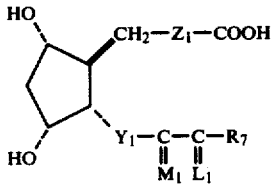
CXXXII
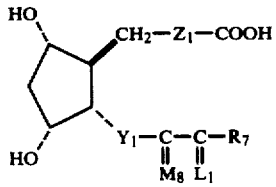
CXXXIII
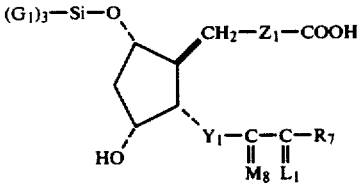
Chart J-continued
CXXXIV
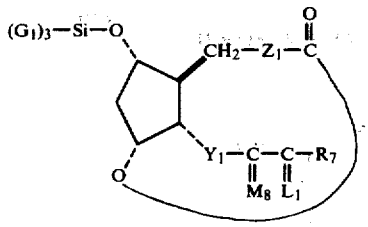
CXXXV
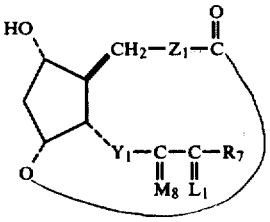
CXXXVI
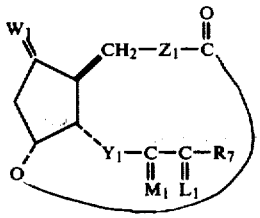
Chart K
CXLI
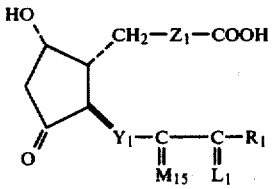
CXLII
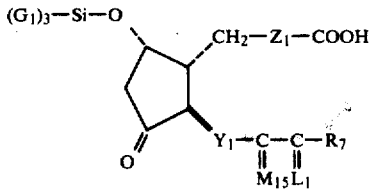

Chart K-continued
CXLIII
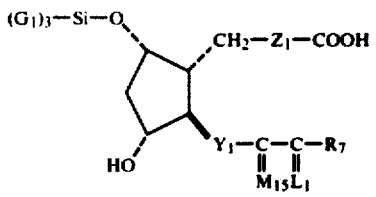
CXLIV
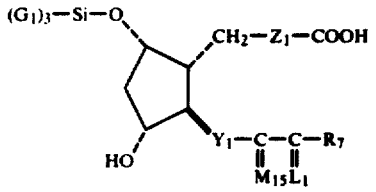
CXLV
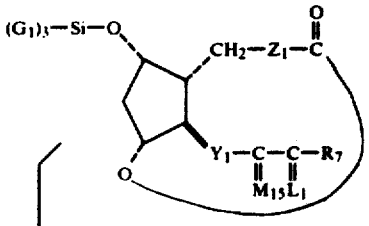
CXLVI
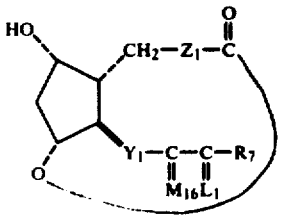
CXLVII
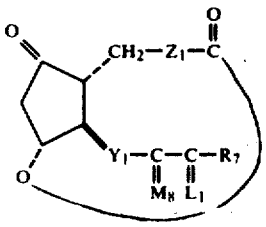
Chart K-continued
CXLVIII
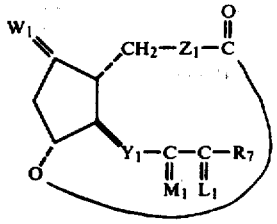
Chart L
CLI
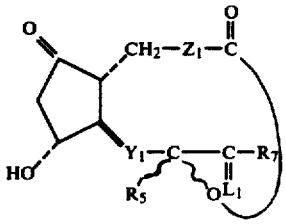
CLII
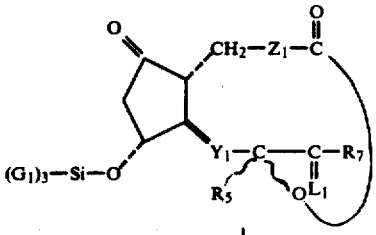
CLIII
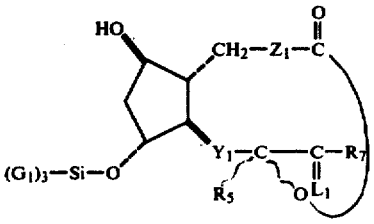
CLIV
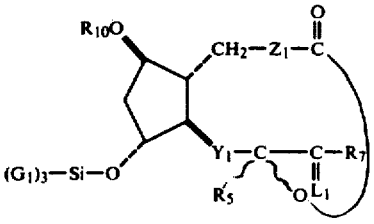
CLV -continued
Chart L
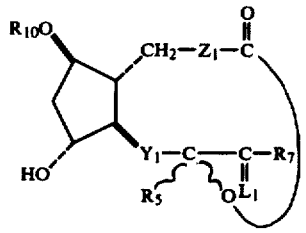
CLVI
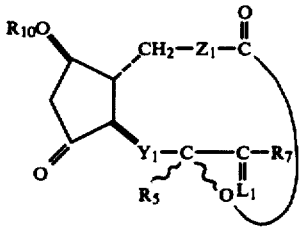
CLVII
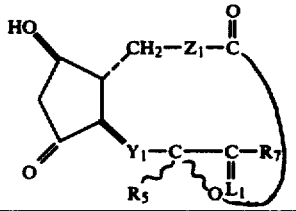
Chart M
CLXI
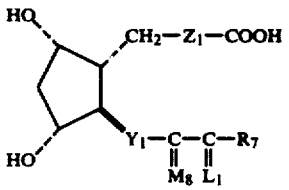
CLXII
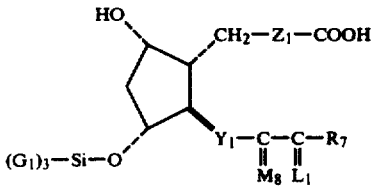
CLXIII
-continued
Chart M
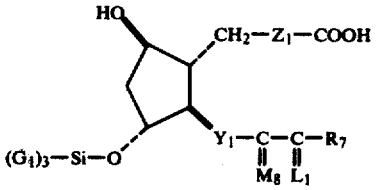
CLXIV
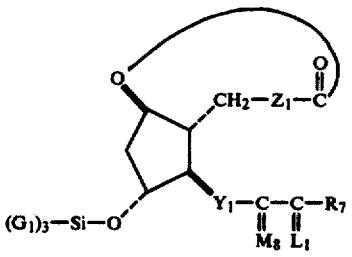
CLXV
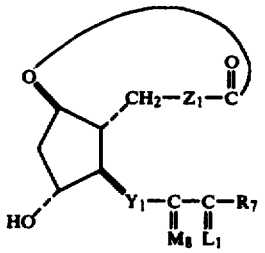
CLXVI
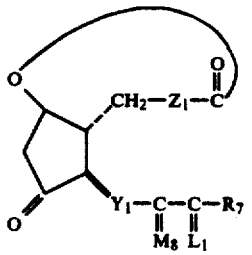
CLXVII
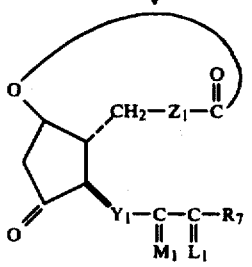
CHART N
CLXXI -continued
CHART N
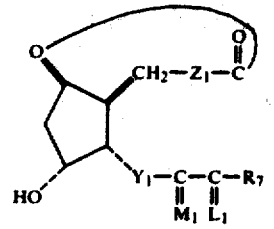
CLXXII
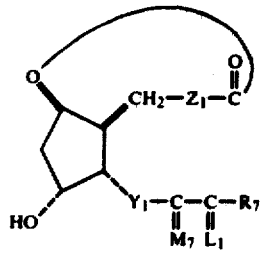
CLXXIII
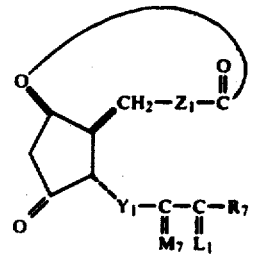
CLXXIV
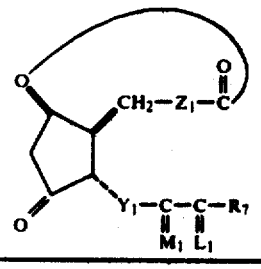
Chart O
CLXXVI
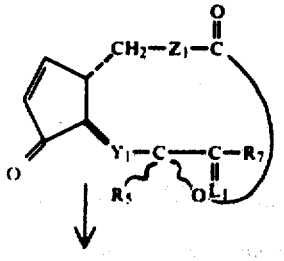
CLXXVII
-continued
Chart O
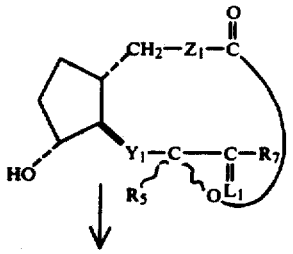
CLXXIII
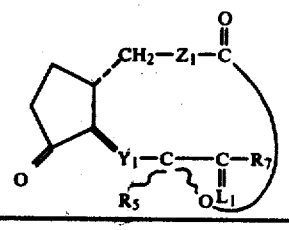
Chart P
CLXXXI
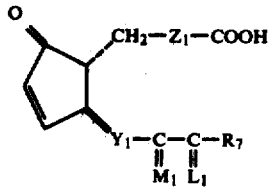
CLXXXII
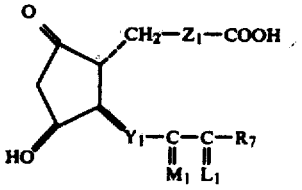
CLXXXIII
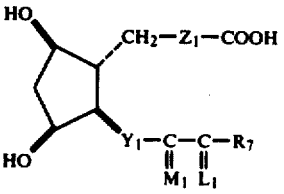
CLXXXIV -continued
Chart P
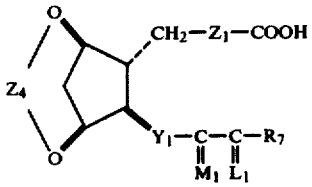
CLXXXV
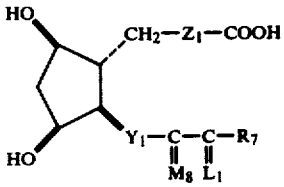
CLXXXVI
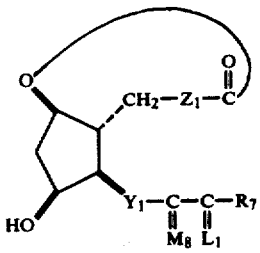
CLXXXVII
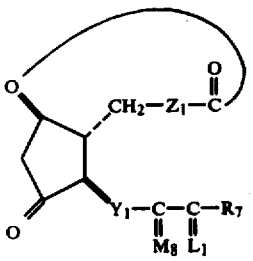
CLXXXVIII
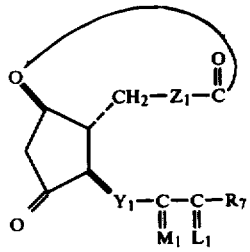
Chart R
CXCI
-continued
Chart R
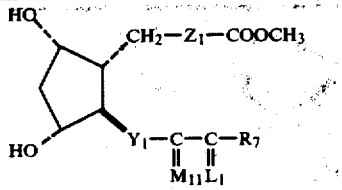
CXCII
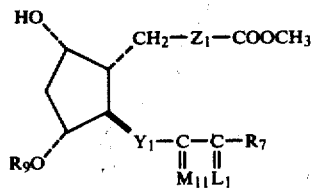
CXCIII
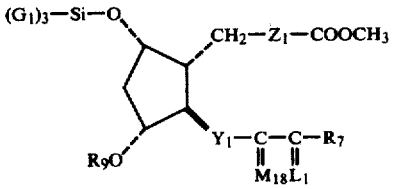
CXCIV
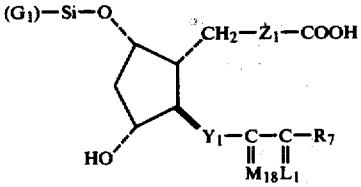
CXCV
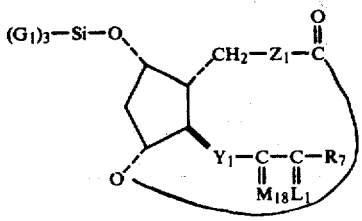
CXCVI
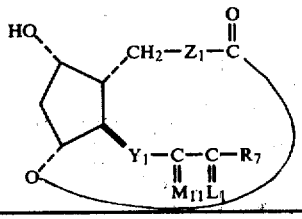
Whereas the present specification describes each of the various lactones of each of the various prostaglandins or prostaglandin analogs described above, the charts below describe methods whereby the desired lactone product is obtained with high selectivity. In each case, the lactonization step itself proceeds by methods known in the art.

For example, South African Pat. No. 737,357 (Derwent Farmdoc CPI No. 28,414V) teaches the preparation of 1,9-lactones of certain PG-type compounds by application of heat to neat samples of the PG-type product. However, for the purposes of the present invention, the method described therein is unsuitable in that only complex mixtures of products are thereby produced.

A further method for lactonization of PG-type compounds is described by Japanese Patent Application No. 5-0037-793 (Derwent Farmdoc CPI No. 61147W) and Japanese Patent Application No. 5-0013-385 (Derwent Farmdoc CPI No. 56267W) wherein trifluoroacetic acid and trifluoroacetic anhydride are employed as lactonization agents. Further, lactonization for prostaglandin-type products is accomplished by the lactonization procedure of S. Masaume, Journal of the American Chemical Society 97, 3515 (1975). By this procedure a mercuric trifluoroacetate catalyzed ring closure of an $\omega$-hydroxy-t-butythiol ester is employed.

However, the preferred procedure of lactonization of the prostaglandin analog described herein proceeds by transformation of the carboxyl of the prostaglandin type compound to a corresponding 2-pyridinethiol ester, followed by ring closure. The general method for this preferred lactonization process is described by E. J. Corey, Journal of the American Chemical Society 96, 5614 (1974), and its application to $PGF_{2\alpha}$ is described by E. J. Corey, et al., Journal of the American Chemical Society 97, 653 (1975). By this preferred procedure the formation of the 2-pyridinethiol ester proceeds by reaction of the prostaglandin type free acid with 1.5 equivalents of 2,2'-dipyridyl disulfide and 1.5 equivalents of triphenylphosphine in a dry (anhydrous) oxygen free xylene or benzene diluent. The 2-pyridinethiol esterification proceeds at room temperature, in about 2–24 hr. The ring closure then proceeds by first diluting the thiol ester obtained above with dry, oxygen free xylene or benzene and thereafter heating to reflux for 1–24 hr.

A modification of the preferred procedure for lactonization is described by H. Gerlach, et al., Helv. Chim. Acta. 57 (8) 2661 (1974). This modification involves ring closure of an $\omega$-hydroxy-2-pyridine thiol ester with silver ion (perchlorate or fluoroborate) catalysis in benzene at room temperature.

With respect to the charts below:

$L_1$, $M_1$, $Y_1$, and $R_7$ are as defined above.

$R_8$ is hydrogen or hydroxy.

$R_9$ is an acyl protecting group.

$R_{10}$ is a blocking group.

$R_{33}$ is —O—Si—$(G_1)_3$ wherein $G_1$ is alkyl, cycloakyl, aralkyl, phenyl, or phenyl substituted with alkyl or halogen, the various $G_1$'s of a —Si—$(G_1)_3$ moiety being the same or different.

$Z_4$ is

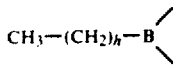

-continued

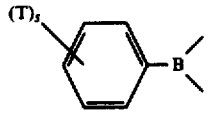

wherein T and s are as defined above, and wherein h is 2 to 4, inclusive, preferably 3.

$M_7$ is

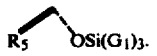

or

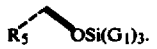

$M_8$ is

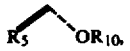

or

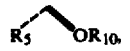

wherein $R_5$ and $R_{10}$ are as defined above.

$M_{11}$ is

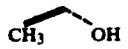

or

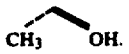

$M_{15}$ is

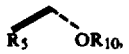

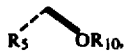

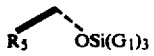

or

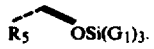

$M_{16}$ is

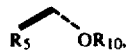

-continued

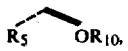

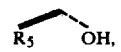

or

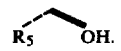

$M_{18}$ is

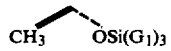

or

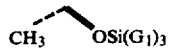

Acyl protecting groups, according to $R_9$, include:

a. benzoyl;

b. benzoyl substituted with one, 2, 3, 4, or 5 alkyl of one to 4 carbon atoms, inclusive, phenyl alkyl of 7 to 10 carbon atoms, inclusive, phenyl, or nitro, with the proviso that not more than 2 substituents are other than alkyl, and that the total number of carbon atoms in the substituents does not exceed 10 carbon atoms, with the further proviso that the substituents may be the same or different;

c. benzoyl substituted with alkoxy carbonyl wherein the alkoxy carbonyl moiety is of 2 to 5 carbon atoms, inclusive;

d. naphthoyl;

e. naphthoyl substituted with one to 9, inclusive, alkyl of one to 4 carbon atoms, inclusive, phenyl alkyl of 7 to 10 carbon atoms, inclusive, or nitro, with the proviso that not more than 2 substituents on either of the naphthyl rings does not exceed 10 carbon atoms, with the further proviso that the various substituents are the same or different; or f. alkanoyl of 2 to 12 carbon atoms, inclusive.

In preparing these acyl derivatives of the hydroxy-containing compounds herein methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. a tertiary amine such as pyridine, triethylamine, or the like. The reaction is carried out under a variety of conditions, using procedures generally known in the art. Generally mild conditions are employed: 20°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides $(R_9)_2O$, or acyl chlorides ($R_9Cl$): benzoyl; substituted benzoyl, e.g., p-phenylbenzoyl, (2-, 3-, or 4-)-methylbenzoyl, (2-, 3-, or 4-)-ethylbenzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,5-trimethylbenzoyl, pentamethylbenzoyl, alpha-phenyl(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching site.

The acyl protecting groups, according to $R_9$, are removed by deacylation. Alkali metal carbonates are employed effectively at ambient temperature for this purpose. For example, potassium carbonate in methanol at about 25° C. is advantageously employed. By the preferred process herein, however, an alkali metal hydroxide is employed in aqueous methanol, e.g. potassium hydroxide.

Those blocking groups within the scope of $R_{10}$ are any group which replaces a hydroxy hydrogen and is neither attacked by nor as reactive to the reagents used in the transformations used herein as an hydroxy is and which is subsequently replaceable with hydrogen in the preparation of the prostaglandin-type compounds. Several blocking groups ae known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51-79 (1969). Those blocking groups which have been found useful include:

a. tetrahydropyranyl;

b. tetrahydrofuranyl; and c. a group of the formula $$-C(OR_{11})(R_{12})-CH(R_{13})(R_{14}),$$

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —(CH- $_2)_a$— or —$(CH_2)_b$— O —$(CH_2)_c$ wherein a is 3, 4, or 5, or b is one, 2, or 3, and *c* is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula $$—C(OR_{11})(R_{12})—CH(R_{13})(R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(OR_{11})(R_{12})=C(R_{13})(R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking groups is achieved.

Various reactions in the succeeding charts introduce silyl groups of the formula —$Si(G_1)_3$. In some cases, such silylations are general, in that they silylate all hydroxy hydrogens, while in other cases they are selective, in that while one or more hydroxyls are silylated, at least one other hydroxyl remains unaffected. For any of these silylations, silyl groups within the scope of —$Si(G_1)_3$ include trimethylsilyl, dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(β-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subject to chromatographic purification, then the use of silyl groups known to be unstable to chromatography (e.g. trimethylsilyl) should be avoided. Further, when silyl groups are to be introduced selectively, silylating agents which are readily available and known to be useful in selective silylations are employed. For example, triphenylsilyl groups and t-butyldimethylsilyl groups are employed when selective introduction is required. Further, when silyl groups are to be selectively hydrolyzed over protecting groups according to $R_{10}$ or acyl protecting groups, then the use of silyl groups which are readily available and known to be easily hydrolyzable with tetran-butylammonium fluoride are employed. A particularly useful silyl group for this purpose is t-butyldimethylsilyl, although other silyl groups (e.g. trimethylsilyl) are likewise employed.

With respect to Chart A, a method is provided where the formula XXI $PGF_{\alpha}$-, 11-deoxy-$PGF_{\alpha}$-, $PFG_{\beta}$-, or 11-deoxy-$PGF_{\beta}$-type compound is transformed to a formula XXII 1,9-lactone or formula XXV 1,15-lactone. Further, Chart A provides a method whereby the formula XXIII 8β,12α-$PGF_{\alpha}$-, 11-deoxy-8β,12α-$PGF_{\alpha}$-, 8β,12α-$PGF_{\beta}$-,, or 11-deoxy-8β,12α-$PGF_{\beta}$-type compound is transformed to a corresponding formula XXIV 1,9 or formula XXVI 1,15-lactone.

The lactonization of Chart A (XXI to XXII or XXV and XXIII to XXIV and XXVI) proceeds as is described above. The product of lactonization is recovered as a mixture of 1,9- and 1,15-lactones. The predominant product is the 1,9-lactone, the proportion of which is increased by the use of benzene rather than xylene, in the lactonization.

Chart B provides a method whereby the formula XXXVII PGD-type, 1,9-lactone is prepared from the formula XXXI $PGF_{\alpha}$-type compound. Likewise, the 8β,12α-$PGF_{\alpha}$-type compound corresponding to formula XXXI is employed to prepare a corresponding 8β,12α-PGD-type compound corresponding to formula XXXVII.

The formula XXXII compound is prepared from the formula XXXI compound by cyclo(alkyl or arylboronization). Accordingly, the bycicylic formula XXXII compound is prepared by reaction of the formula XXXI compound with a slight stoichiometric excess of a corresponding alkyl or arylboronic acid. The course of the reaction is conveniently monitored gas chromatography and the reaction is preferably carried forth under vigorous stirring at reflux temperature. The preferred reaction diluent for this transformation is methylene chloride, although other suitable organic solvents are alternatively employed. The formula XXXII compound so formed is then etherified at the C-15 position by replacing the hydroxyl hydrogen with a blocking group according to $R_{10}$. Procedures described above for the use of such blocking groups are employed. Thereafter the formula XXXIV compound is prepared from the formula XXXIII compound by decycloboronization. For this purpose an alkali hydroxide (e.g. sodium, lithium, or potassium hydroxide) is combined with the formula XXXIII compound in a water miscible diluent capable of yielding a homogeneous reaction mixture (e.g. methanol or ethanol). The resulting solution is thereafter treated with dilute aqueous hydrogen peroxide. Thereafter the formula XXXV compound is prepared from the formula XXXIV compound by the lactonization procedure described above. This formula XXXV $PGF_{\alpha}$-type, 1,9-lactone is then transformed to the corresponding PGD-type 1,9-lactone by oxidation of the C-11 hydroxy to an oxo. Methods known in the art for such an oxidation are employed. Thus, for example, a slight stoichiometric excess of Jones reagent is reacted with the formula XXXV compound at a temperature of −20° to −40° C. The formula XXXVII compound is then prepared from the formula XXXVI compound by hydrolysis of the blocking group, employing methods hereinabove described.

Chart C provides a method whereby the formula XLI $PGF_{\alpha}$- or 11-deoxy-$PGF_{\alpha}$-type compound is transformed to a formula XLVIII $PGF_{\alpha}$-, 11-deoxy-$PFG_{\alpha}$-, or 11-deoxy-$PGF_{\beta}$-type, 1,15-lactone or a formula L PGE- or 11-deoxy-PGE-type, 1,15-lactone or a formula LII PGD-type, 1,15-lactone.

By the procedure of Chart C the formula XLI compound is transformed to the formula XLII compound by selective silylation at C-11 and C-15 over C-9. Silyl groups according to the formula $—Si(G_1)_3$, wherein $G_1$ is defined above, are advantageously employed. For selective monosilylation procedures see U.S. Pat. No. 3,822,303, issued July 2, 1974, German Offenlegungsschrift No. 2,259,195 (Derwent Farmdoc CPI No. 36457U-B) or Netherlands Pat. No. 7,214,142 (Derwent Farmdoc CPI No. 26221U-B). Subsequently, there are performed the optional transformations of the formula XLII compound to the formula XLIII compound, and thereafter the formula XLIV compound. The formula XLIII compound is prepared from the formula XLII compound by oxidation of the 9-hydroxy to an oxo. Methods known in the art are employed. For example, the use of the Jones reagent or the Collins reagent or such additional reagents as are known to transform $PGF_{\alpha}$-type compounds to corresponding PGE-type compounds is known and employed herein. Subsequently, the formula XLIII compound is transformed to the formula XLIV compound by reduction of the 9-oxo of the formula XLIII compound to the corresponding 9-hydroxy compound and separation of the 9β-hydroxy isomer from the isomeric mixture so formed. This reduction is performed by methods known in the art. For example, the use of sodium, potassium, or lithium borohydride reducing agents and such other agents as is known in the art for reduction of PGE-type compounds to mixtures of $PGF_{\alpha}$ and $PGF_{\beta}$-type compounds is known and employed herein. The 9-epimeric mixture is conveniently separated by silica gel chromatography, yielding the formula XLIV product.

Thereafter, the formula XLII or formula XLIV compounds are transformed to the formula XLV compound by replacing the 9-hydroxy hydrogen with a blocking group according to $R_{10}$. Methods known in the art and hereinabove described are employed. Thereafter the formula XLV compound is transformed to the formula XLVI compound by selective hydrolysis of any silyl groups over any blocking groups according to $R_{10}$. This selective removal of any silyl groups is accomplished by methods known in the art. See for reference Corey, et al., Journal of the American Chemical Society 94, 6190 (1972). An especially useful reagent for this purpose is tetra-n-butyl-ammonium fluoride in tetrahydrofuran.

Thereafter the formula XLVI compound is transformed to the formula XLVII compound by 1,15-lactonization. Lactonization methods described above are employed.

The formula XLVIII $PGF_{\alpha}$-, 11-deoxy-$PGF_{\alpha}$-, $PGF_{\beta}$-, or 11-deoxy-$PGF_{\beta}$-type, 1,15-lactones are then prepared from the formula XLVII compound by hydrolysis of the blocking group according to $R_{10}$. This hydrolysis proceeds by methods hereinabove described.

The formula L PGE- or 11-deoxy-PGE-type, 1,15-lactone is then prepared from the formula XLVIII $PGF_{\alpha}$- or 11-deoxy-$PGF_{\alpha}$-type, 1,15-lactone by first selective silylation at C-11 over C-9 (formula XLIX) employing methods described in the transformation of the formula XLI compound to the formula XLII compound; oxidizing the formula XLIX silylated compounds so formed to a corresponding 9-oxo compound, employing methods known in the art for transformation of $PGF_{\alpha}$-type compounds to PGE-type compounds as described above; and thereafter optionally hydrolyzing any silyl group employing methods and procedures known in the art.

Alternatively the formula XLVII compound is employed in the preparation of the formula LI compound. In this transformation the 11-hydroxy of the formula XLVII compound is oxidized to the corresponding formula LI 11-oxo compound. Procedures known in the art are employed. For example, see Tetrahedron Letters, 2235 (1974). Useful reagents for this purpose include those oxidizing reagents described above as useful in the transformation of PGF-type compounds to PGE-type compounds. The formula LI compound is then hydrolyzed at C-9, preparing the formula LII PGD-type, 1,15-lactone.

Chart D provides a method whereby the formula LXI 8β,12α-$PGF_{\alpha}$-type compound is transformed to a formula LXIV 8β,12α-$PGF_{\alpha}$-type, 1,15-lactone; a formula LXIX 8β,12α-PGE-type, 1,15-lactone; a formula LXXI 8β,12α-$PGF_{\beta}$-type, 1,15-lactone; or a formula LXXIII 8β,12α-PGD-type, 1,15-lactone. Additionally, the transformations of the formula LXI compound to the formula LXII compound are optionally employed on the 8,12-isomers of those depicted by formulas LXI to LXIV, respectively, thereby preparing the $PGF_{\alpha}$-type, 1,15-lactone corresponding to formula LXIV.

The transformation of the formula LXI compound to the formula LXII compound of Chart D proceeds by the method described in Chart B for the preparation of the formula XXXII compound from the formula XXXI compound. Thereafter, the formula LXXII compound is 1,15-lactonized, forming the formula LXIII compound. This lactonization proceeds by the methods hereinabove described. Thereafter, the formula LXIII compound is decyclo(alkylboronized) employing the procedure described in Chart B for the transformation of the formula XXXIII compound to the formula XXXIV compound. Accordingly, the 8β,12 α-$PGF_{\alpha}$-type, 1,15-lactones are prepared.

Thereafter, the formula XLIV compound is transformed to the formula LXV compound by selective silylation of the C-9 hydroxy over the C-11 hydroxy. This selective silylation proceeds by methods known in the art. For example, see U.S. Pat. No. 3,822,303, issued July 2, 1974, German Offenlegungsschrift, No. 2,259,195 (Derwent Farmdoc CPI No. 36457U-B) or Netherlands Pat. No. 7,214,142 (Derwent Farmdoc CIP No. 26221U-B). Thereafter, the formula LXV compound is employed in the preparation of either the formula LXVI compound or the formula LXXII compound.

The formula compound is transformed to the formula LXVI compound by replacing the 11-hydroxy hydrogen with a blocking group according to $R_{10}$. Methods known in the art, hereinabove described, are employed.

The formula LXVI compound is then transformed to the formula LXVII compound by selective hydrolysis of the silyl group over the blocking group according to $R_{10}$. Methods hereinabove described for such selective hydrolysis are employed. See the transformation of the formula XLIV compound to the formula XLVI compound of Chart C.

Thereafter, the formula LXVII compound is transformed to the formula LXVIII compound by oxidation of the 9-hydroxy to a corresponding 9-oxo compound. Reagents and procedures known in the art for transformation of $PGF_{\alpha}$-type compounds to PGE-type compounds are employed. The formula LXVIII compound is then hydrolyzed, whereby blocking groups according to $R_{10}$ are removed, thereby preparing the formula LXIX 8β,12α-PGE-type, 1,15-lactone. Methods of hydrolysis of blocking groups according to $R_{10}$ hereinabove described are employed.

Thereafter the formula LXIX compound is transformed to the formula LXXI compound by a ring carbonyl reduction, employing methods known in the art for the transformation of PGE-type compounds to the corresponding $PGF_{\beta}$ compounds. Accordingly, sodium, potassium, or lithium borohydride is employed in the reduction, followed by chromatographic separation of the 9β-hydroxy epimer from the 9-epimeric mixture so formed. Accordingly, there is prepared 8β,12α-$PGF_{\beta}$-type, 1,15-lactones of formula LXXI.

The formula LXV compound is employed in the preparation of the formula LXXII compound by selective oxidation of the C-11 hydroxy to a corresponding oxo. Methods described in Chart G and the transformation of formula LXVII compound to the formula formula LI compound are employed. Thereafter the formula LXXII compound is transformed to the formula LXXIII 8β,12α-PGD-type, 1,15-lactone following procedures described above for hydrolysis of silyl groups.

Chart E provides a method whereby the formula LXXXI PGE- or 11-deoxy-PGE-type starting material is transformed to the formula Ixxxii PGE- or 11-deoxy-PGE-type, 1,15-lactones, or the formula LXXXV $PGF_{\alpha}$-, 11-deoxy-$PGF_{\alpha}$-, $PGF_{\beta}$-, or 11-deoxy-$PGF_{\beta}$-type, 1,15-lactones. Further, Chart E describes the use of the formula LXXXIII 8β,12α-PGE- or 11-deoxy-8β,12α-PGE-type compound in the preparation of the formula LXXXIV 8β,12α-PGE- or 11-deoxy-8β,12α-PGE-type, 1,15-lactones or the formula LXXXVI 8β,12α-$PGF_{\alpha}$-, 11-deoxy-8β,12α-$PGF_{\alpha}$-, 8β,12α-$PGF_{\beta}$-, or 11-deoxy-8β,12α-$PGF_{\beta}$-type, 1,15-lactones.

For the transformation of the formula LXXXI or LXXXIII compound to the formula LXXXII or formula LXXXIV compound, respectively, lactonization methods hereinabove described are employed. Thereafter, the formula LXXXIV or formula LXXXVI compound is prepared from the formula LXXXIII compound, respectively, by a ring carbonyl reduction, followed by separation of C-15 epimers. These ring carbonyl reductions and epimeric separations are performed by methods described hereinabove. See the transformation of the formula XLIII compound to the formula LXIV compound of Chart C.

Chart F provides a method whereby the formula XCI PGE-type compound is transformed to the formula XCII PGA-type, 1,15-lactone; the formula XCIII 8β,12α-PGE-type, 1,15-lactone is transformed to the formula XCIV 8β,12α-PGA-type, 1,15-lactone; a formula XCV PGD-type, 1,15-lactone is transformed to a formula XCVI 9-deoxy-9,10-didehydroPGD-type, 1,15-lactone; or a formula XCVII 8β,12α-PGD-type, 1,15-lactone is transformed to a formula XCVIII 9-deoxy-9,10-didehydro-8β,12α-PGD-type, 1,15-lactone.

For each of the above transformations of Chart F, the hydroxyl on the cyclopentane ring is dehydrated to the corresponding compound with α,β-unsaturation to the ketone employing mild acidic dehydration. For example, methods known in the art for the transformation of PGE-type compounds to PGA-type compounds are employed. Alternatively, the various starting materials of Chart F are transformed to corresponding acetates (e.g. employing acetic anhydride), and thereafter chromatographed on silica gel to effect the desired dehydration.

Chart G provides a method whereby the formula CI PGA-type compound, formula CII PGB-type compound, formula CIII, formula CV 11-deoxy-PGE-type compound, or their respective 8β,12α-isomers, are transformed to a corresponding formula CVI PG-type, 1,15-lactone wherein the cyclopentane ring structure of the starting material is preserved. Since each of the formula CI to formula CV compounds is monohydroxylated, lactonization proceeds by the general methods described hereinabove without the use of any selective blocking.

With respect to Chart H, a method is provded whereby the formula CXI $PGF_{\alpha}$-type compound is transformed to a formula CXIX $PGF_{\alpha}$-type, 1,11-lactone, formula CXXII PGE-type, 1,11-lactone, or formula CXXIII $PGF_{\beta}$-type, 1,11-lactone.

With respect to Chart H, the transformation of the formula CI compound to the formula CIV compound employs the methods hereinabove described in Chart B for the transformation of the formula XXXI compound to the formula XXXIV compound. Thereafter, the formula CXV compound is prepared from the formula CXIV compound by selective silylation. Accordingly, methods described in Chart C for the transformation of the formula XLI compound to the formula XLII compound are employed.

Thereafter the formula CXV compound is transformed to the formula CXVI compound by transformation of the 9-hydroxy hydrogen to a blocking group according to $R_{10}$. Methods described hereinabove are employed. Thereafter, the formula CXV compound is transformed to the formula CXVI compound by selective hydrolysis of the 11-silyl group. Methods described hereinabove are employed. See, the transformation of the formula XLV compound to the formula XLVI compound in Chart C.

Thereafter, the formula CXVII compound is 1,11-lactonized, thereby forming the formula CXVIII compound. This lactonization proceeds by methods known in the art and described hereinabove.

Thereafter, the formula CXIX $PGF_{\alpha}$-type, 1,11-lactone is prepared from the formula CXVIII compound by hydrolysis of a blocking groups according to $R_{10}$. Methods known in the art and hereinabove described are employed.

Thereafter, the formula CXX compound is prepared from the formula CXIX compound by selective silylation. This selective silylation of the C-15 hydroxyl over the C-9 hydroxyl is accomplished by methods known in the art and described and referenced in Chart C for the transformation of the formula CXLI compound to the formula CXLII compound. Thereafter, the formula CXX compound is oxidized at the C-9 position to the corresponding formula CXXI compound employing methods known in the art for the transformation of $PGF_{\alpha}$-type compounds to corresponding PGE-type compounds. Thereafter, the formula CXXII PGE-type, 1,11-lactone is prepared by hydrolysis of the silyl group, employing methods known in the art.

Finally, the formula CXXIII $PGF_{\beta}$-type, 1,11-lactones are prepared from the formula CXXII PGE-type, 1,11-lactones by ring carbonyl reduction and separation of the 9-epimeric mixture thereby obtained. Accordingly, methods described hereinabove, i.e. the transformation of the formula XLIII compound to the formula XLIV compound of Chart C, are employed.

Chart J provides a method whereby formula CXXXI $8\beta,12\alpha$-$PGF_{\alpha}$-type compound is transformed to a formula CXXXVI $8\beta,12\alpha$-$PGF_{\alpha}$-, $8\beta,12\alpha$-$PGF_{\beta}$-, or $8\beta,12\alpha$-PGE-type, 1,11-lactone.

With respect to Chart J, the formula CXXXI compound is transformed to the formula CXXXII compound by a selective etherification at C-15. Methods described in proceeding charts are employed. See the transformation of the formula XXXI compound to the formula XXXIV compound of Chart B. Thereafter, the formula CXXXII compound is selectively silylated at the C-9 position, thereby preparing the formula CXXXIII compound. This selective silylation proceeds by the method described in the transformation of the formula LXIV compound to the formula LXV compound of Chart D.

Thereafter, the formula CXXXIII compound is transformed to the formula CXXXIV compound by 1,11-lactonization, employing the lactonization procedures described hereinabove. Thereafter the formula CXXXV compound is prepared from the formula CXXXIV compound by selective hydrolysis of the silyl group in the presence of a blocking group according to $R_{10}$. Methods described in Chart C in the transformation of the formula CXLV compound to the formula CXLVI compound are employed.

Thereafter, the formula CXXXV compound is transformed to the formula CXXXVI compound employing methods hereinabove described in the transformation of $PGF_{\alpha}$-type lactones to corresponding PGE-type and $PGF_{\beta}$-type lactones.

Chart K provides a method whereby the formula CXLI compound or its $8\beta,12\alpha$-isomer is transformed to the corresponding formula CXLVIII PG-type 1,11-lactone or its $8\beta,12\alpha$-epimer.

With respect to Chart K the formula CXLI starting material is prepared in the manner of the formula XXXV compound of Chart B when $M_{15}$ is the same as $M_8$. The $8\beta,12\alpha$-compound wherein $M_{15}$ is the same as $M_8$ corresponding to formula CXLI is prepared in the manner of the formula XXXV compound of Chart B employing $8\beta,12\alpha$-$PGF_{\alpha}$-type starting material corresponding to formula XXXI.

When $M_{15}$ is the same as $M_7$ for the formula CXLI compound of Chart K, then the formula CXLI compound is prepared by selective silylation employing the method described in Chart H for the preparation of the formula CXX compound from the formula CXIX compound.

The formula CXLII compound is prepared from the formula CXLI compound by silylation at C-9. Methods known in the art for the introduction of silyl groups are employed. Thereafter, the formula CXLIII compound is prepared from the formula CXLII compound by reduction of the 11-oxo to an 11-hydroxy. This reduction proceeds by methods herein described for the transformation of PGE-type compounds to corresponding PGF-type compounds. Finally, the formula CXLIV compound is prepared from the formula CXLIII compound by separation of the 11-epimeric mixture employing silica gel chromatography.

The formula CXLIV compound is then 1,11-lactonized forming the formula CXLV compound. This is lactonization proceeds by the general methods hereinabove described. Thereafter, the formula CXXXV compound is transformed to CXXXVI compound by hydrolysis of the silyl groups. When $M_{15}$ is the same as $M_8$, this hydrolysis proceeds selectively by methods hereinabove described. See the transformation of the formula CXLV compound to the formula CXLVI compound of Chart C. Otherwise, methods generally known in the art for removal of silyl groups, without hydrolyzing ester linkages, are employed.

Thereafter, the formula CXLVI compound wherein $M_{16}$ is the same as $M_8$ is transformed to the formula CXLVII compound, employing methods hereinabove described for the transformation of $PGF_{\alpha}$-type compounds to PGE-type compounds. Finally, the formula CXLVII compound is transformed to the various formula CXLVIII PG-type, 1,11-lactones employing ring transformations hereinabove described and hydrolyzing the blocking group according to $R_{10}$, following procedures hereinabove described.

Chart L provides a method whereby the formula CLI PGE-type 1,15-lactone, or its $8\beta,12\alpha$-isomer is transformed to a corresponding formula CLVII $9\beta$-PGD- or PGD-type, 1,15-lactone or its $8\beta,12\alpha$-isomer, respectively.

With respect to Chart L the formula CXLII compound is prepared from the formula CXLI compound by silylation. Methods known in the art and hereinabove described are employed. The formula CXLIII is then prepared from the formula CXLII compound by a ring carbonyl reduction, employing methods hereinabove described. The 9-epimeric mixture thusly prepared is then separated by silica gel chromatography, preparing the separated formula CLIII epimers.

The formula CLIV compound is then prepared from the formula CLIII compound by transforming the 9-hydroxy hydrogen to a blocking group according to $R_{10}$. Methods described hereinabove are employed.

Thereafter the silyl groups are selectively hydrolyzed over the blocking groups according to $R_{10}$, following procedures described in Chart B for the transformation of the formula CXLV compound to the formula CXLVI compound. Thereupon, the formula CXLV compound is oxidized at the C-11 position to the corresponding 11-oxo compound. Methods hereinabove described, particularly the transformation of the formula XXXV compound to the formula XXXVI compound of Chart B are employed.

Thereafter, the $9\beta$-PGD- or PGD-type, 1,15-lactones of formula CXLVII are prepared from the formula CXLVI compound by hydrolysis of the blocking groups according to $R_{10}$. Methods known in the art and hereinabove discussed are employed.

Chart M provides a method whereby the formula CLXI $PGF_{\alpha}$-type compound is transformed to a formula CLXVII $9\beta$-PGD-type, 1,9-lactone.

With respect to Chart M the formula CLXI compound is available as formula XXXIV of Chart B. Thereafter, this compound is transformed to the formula CLXII compound by selective silylation of the C-11 hydroxy over the C-9 hydroxy, employing methods described in Chart C (the transformation of the formula XLI compound to the formula XLII compound).

Thereafter, the formula CLXII compound undergoes a 9-epimerization to form the formula CLXIII $PGF_{\beta}$- type compound. This epimerization is accomplished by one of several methods known in the art. For example, the formula CLXII compound is optionally oxidized to a 9-oxo compound, and thereafter the 9-oxo compound reduced to the corresponding 9-hydroxy epimeric mixture. Alternatively, the method of E. J. Corey, et al., J. Chem. Soc., Chemical Communications 658 (1975) is employed.

Thereafter the formula CLXIII compound is 1,9-lactonized to the formula CLXIV compound. Lactonization procedures described hereinabove are employed. Thereafter the formula CLXV compound is prepared from the formula CLXIV compound by selective hydrolysis of the silyl group in the presence of blocking groups according to $R_{10}$. Procedures employed in Chart C for the transformation of the formula LXV compound to the formula LXVI compound are employed. Thereafter, the formula CLXVI compound is prepared from the formula CLXV compound by oxidation of the 11-hydroxy to an 11-oxo. This oxidation proceeds by methods described in Chart B for the transformation of the formula XXXV to the formula XXXVI compound.

Thereafter, formula CXXXVII PGD-type, 1,9-lactone is prepared from the formula CXXXVI compound by hydrolysis of the blocking group according to $R_{10}$ employing methods hereinabove described.

Chart N provides a method whereby the formula CLXXI 8β,9β,12α-PGF-type, 1,9-lactone is transformed to the corresponding 8β,9β,12α-PGD-type, 1,9-lactone of formula CLXXIV.

With respect to Chart N the formula CLXXII compound is prepared from the formula CLXXI compound by selective silylation of the C-15 hydroxy. This selective silylation accomplished by the procedure described in Chart J for the transformation of the formula CLXIX compound to the formula CLXX compound. Thereafter the formula CLXXIII compound is prepared from the formula CLXXII compound by oxidation of the 11-hydroxy to an 11-oxo. This oxidation is accomplished by methods described in Chart B in the transformation of the formula XXXV compound to the formula XXXVI compound.

Thereafter, the formula CLXXIV 8β,9β,12α-PGD-type, 1,9-lactone is then prepared from the formula CLXXIII compound by hydrolysis of the silyl group at C-15. The hydrolysis proceeds by those methods known in the art to remove silyl groups while not affecting ester linkages.

Chart O provides a method whereby the formula CLXXVI 9-deoxy-9,10-didehydro-PGD-type, 1,15-lactone is transformed to a corresponding formula CLXXVIII 9-deoxy-PGD-type, 1,15-lactone. Alternatively, 9,10-didehydro-9-deoxy-8β,12α-PGD-type compounds are employed in place of the formula CLXXVI starting material preparing corresponding 9-deoxy-8β,12α-PGD-type products.

The formula CLXXVII starting material or its 8β,12α-isomer is prepared by dehydration of a corresponding PGD- or 8β,12α-PGD-type, 1,15-lactone. This dehydration proceeds by mild acid catalysis, employing organic acids such as acetic acid, trifluoroacetic acid, citric acid, oxalic acid, or p-toluenesulfonic acid. This dehydration proceeds rapidly at temperatures between ambient temperature at about 40° C. Alternatively, the dehydration is affected by allowing the formula CLXXVI starting material (or its 8β,12α-isomer) to stand on a column of acid washed silicagel.

The reaction sequence of Chart O proceeds by methods known in the art for transforming PGA-type compounds to corresponding 11-deoxy-PGE-type compounds . Accordingly, the formula CLXXVI starting material is subjected to a potassium, sodium, or lithium borohydride reduction as is known in the art. For this purpose, for example, the reaction is carried out at about −20° C., and is ordinarily complete within a few mintues. Thereafter, the formula CLXXVII compound, thusly obtained, is oxidized to the formula CLXXVIII 9-deoxy-PGD-type, 1,15-lactone employing oxidation agents known in the art for this purpose. Thus, for example, the Jones or Collins reagent as described above, are employed.

Chart P provides a method whereby the formula CLXXXIII 11β-PGF $_{\beta}$-type compound (or its 8β,12α-isomer) is transformed to a formula CLXXXVIII 9β-PGD-type, 1,9-lactone (or a corresponding 8β,9β, 12α-PGD-type, 1,9-lactone).

With respect to Chart P the formula CLXXXIII compound is known in the art or prepared by methods known in the art. For example, its preparation proceeds from the formula CLXXXI PGA-type compound by 9,10-epoxidation, reduction of the expoxide to an (11RS)-hydroxy mixture and chromatographic separation of the 11β-hydroxy compound from the epimeric mixture. This reaction sequence, preparing the formula CLXXXII compound, is then followed by a ring carbonyl reduction, yielding the formula CLXXXIII starting material. When the 8β, 12α-isomer of the formula CLXXXIII compound is desired, such compounds are known in the art or prepared by methods known in the art as enantiomers or 15-epi enantiomers of $PGF_{2\alpha}$-type compounds. Methods for epoxidation, reduction of the epoxide, and separation of the epimeric mixture of alcohol so formed are described in Belgium Pat. No. 804,837 (Derwent Farmdoc CPI No. 22865V).

This formula CLXXXIII compound is then cyclo(alkylboronized) to the formula CLXXXIV compound, following the procedure described in Chart B for the preparation of the formula XXXII compound from the formula CXXXI compound. Thereafter, the formula CLXXXIV compound is transformed to the formula CLXXXV compound by the procedure described in Chart B for the preparation of the formula CXXXIV compound from the formula CXXXII compound. This C-15 selectively protected formula CLXXXV compounds is then 1,9-lactonized to a corresponding formula CLXXXVI compound, employing the lactonization procedures described hereinabove. Thereafter, the formula CLXXXVI compound is converted to the formula CLXXXVIII compound employing the method described in Chart B for the preparation of the formula XXXVII compound from the formula XXXV compound.

Chart R provides a method whereby the formula CXCVI 15-methyl-$PGF_{\alpha}$,1,11-lactone is conveniently prepared from the formula CXCI 15-methyl-$PGF_{\alpha}$-type compound.

With regard to Chart R, the formula CXCII compounds is prepared from the formula CXCI compound by selective acylation. This selective acylation is achieved by employing a single equivalent of the acylating agent (e.g. acyl chloride) and terminating the reaction promptly after the selective C-11 protection is effected. General methods described above for the introduction of acyl protecting groups are employed.

Thereafter, the formula CXCIII compound is prepared from the formula CXCII compound by silylation. Silylation procedures known in the art are employed. Thereafter, the formula CXCIV compound is prepared from the formula CXCIII compound by selective removal of the acyl protecting group according to $R_9$. This selective removal of the acyl protecting group is accomplished employing potassium, sodium, or lithium hydroxide in aqueous methanol, as described above.

Thereafter, the formula CXCV compound is prepared from the formula CXCIV compound by 1,11-lactonization. This lactonization proceeds as hereinabove described.Finally, formula CVI compound is prepared from the formula CXV compound by removal of the silyl groups, as hereinabove described.

With the exception of the procedure in Chart R, where the 15-hydroxy hydrogen is replaced on a 15-methyl-PG-type compound, or, in Charts H, J, and K where PG-type, 1,11-lactones are prepared, the introduction of silyl groups or blocking groups according to $R_{10}$ in place of the hydroxy hydrogen at C-15 is not required for the various transformations of the above charts when the 15-methyl compounds are employed. Accordingly, when the 15-hydroxy hydrogen is the only hydroxy hydrogen to be blocked or silylated, then such blocking or silylation may be omitted. Further, when one or both of any secondary hydroxyls at C-9 or C-11 are to be blocked or silylated in addition to the C-15 tertiary hydroxyl, then the transformation effecting the blocking or silylation need only be carried out until any secondary hydroxyls have been so transformed.

However, when the hydroxy hydrogen of a 15-methyl-PG-type compound is replaced with a blocking group according to $R_{10}$, then the subsequent hydrolysis of the blocking group in many cases epimerizes the C-15 hydroxyl. In such cases, epimeric purity of the product then requires separation employing silica gel chromatography, high pressure liquid chromatography, or other techniques known to separate prostaglandin-type diastereomers.

The present invention particularly provides a prostaglandin-type 1,9-lactone of the formula

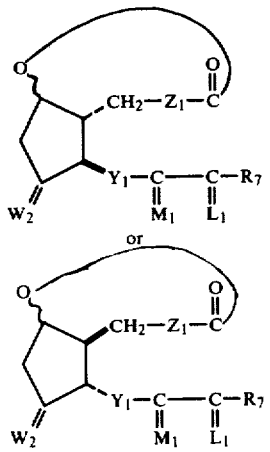

wherein $Z_1$, $W_2$, $Y_1$, $M_1$, $L_1$, and $R_7$ are as defined above.

Each of the various prostaglandin-type, 1,9-lactones of the present invention is useful for each of the corresponding purposes for which the corresponding free acid of each of these lactones is used. In particular, these protaglandin-type, 1,9-lactones are administered by the same routes as the corresponding free acids and for each particular purpose are administered in doses of about 5 to 1000 times the dosage at which the corresponding free acid is admistered by the same route.

Surprisingly and unexpectedly, however, in administering various prostaglandin-type, 1,9-lactones herein the host experiences increased tolerance of drug and fewer undesirable sideeffects associated with each respective route of administration. For example, when the prostaglandin-type, 1,9-lactones of the present invention are administered intravenously, higher infusion rates are successfully employed with reduction or elimination of undesirable local effects associated with administration of the corresponding free acid.

Additionally, when intramuscular administration is employed, the present PG-type, 1,9-lactones provide more consistent release rates from the injection site and in particular a more prolonged duration of release than the corresponding free acid. Accordingly, the present prostaglandin-type, 1,9-lactones exhibit surprisingly and unexpectedly prolonged activity when administered by this route.

The PGD-type, 1,9-lactones and 8$\beta$, 12$\alpha$-PGD-type, 1,9-lactones are accordingly surprisingly and unexpectedly more useful blood pressure lowering agents, gastric antisecretory agents, and platelet aggregation inhibiting agents, than the corresponding free acids. Most particularly these lactones exhibit surprisingly improved stability, both as bulk chemicals and finished pharmaceutical formulations. Further, when administered at therapeutic doses, these lactones exhibit a surprisingly and unexpectedly more sustained duration of action than the corresponding free acids, an improved therapeutic ratio, and a lower incidence of prostaglandin-related gastrointestinal and bronchopulmonary side effects than the correspnding free acids. Accordingly, these compounds are surprisingly and unexpectedly more useful than the corresponding free acids in the treatment of hypertension, gastrointestinal hyperacidity, gastrointestinal ulcers and coagulative disorders of the cardiovascular system.

The $PGF_\alpha$-type, 1,9-lactones; 8$\beta$,12$\alpha$-$PGF_\alpha$-type, 1,9-lactones; 11-deoxy-$PGF_\alpha$-type, 1,9-lactones; 11-deoxy-8$\beta$,12$\alpha$-$PGF_\alpha$-type, 1,9-lactones; $PGF_\beta$-type, 1,9-lactones; 8$\beta$,12$\alpha$-$PGF_\beta$-type, 1,9-lactones; 11-deoxy-$PFG_\beta$-type, 1,9-lactones; and 11-deoxy-8$\beta$,12$\alpha$-$PGF_\beta$-type, 1,9-lactones are accordingly surprisingly and unexpectedly more useful than the corresponding free acids when used as nasal decongestants, oxytocic agents, regulators of the mammalian reproductive cycle, and inhibitors of inflammatory proliferative dermatosis (such as psoriasis), in that these lactones exhibit a prolonged duration of activity. Thus, these lactones are surprisingly and unexpectedly more useful than the corresponding free acids in including menstruation terminating pregnancy, and preventing excessive postpartium bleeding. In addition to the surprisingly and unexpectedly prolonged duration of activity, these compounds at therapeutic doses also exhibit a decreased incidence of prostaglandin-associated gastrorintestinal side effects, particularly nausea, vomiting and diarrhea, and when used as oxytocic agents, or otherwise as regulators of mammalian reproductive cycle, a lower incidence of cardiovascular or pulmonary side effects is evident.

These PGF-, or 11-deoxy- PGF-type, 1,9-lactones or their 8$\beta$,12$\alpha$ -isomers additionally produce hyperthermic or hypothermic responses and accordingly in initiating treatment with these lactones it is especially important to monitor body temperature, adjusting dosages so that the absolute change in body temperature from normal is less than or equal to 1.5° to 2° C. Acccordingly, administration of the lactone is discontinued or the rate of administration decreased in the event excessive body temperature changes appear imminent.

Thus, the various lactones described above are employed for the above described purposes being administered orally, vaginally, topically, internasally, interamniotically, or parenterally and being formulated as tablets, capsules, nosedrops, aerosols, creams, ointments, suppositories or oral-based or water-based solutions or suspensions, as is known in the art for corresponding administration and formulation of corresponding free acids or their alkyl esters.

DESCRIPTION OF THE PREFERRED EMBODIMENTS

The invention can be more fully understood by the following examples and preparations.

All temperatures are in degrees centigrade. IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60-D, and T-60 spectrophotometer on deuterochloroform solutions with tetramethylsilane as an internal standard (downfield).

Mass spectra are recorded on an CEC model 21-110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column. "Brine", herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol, Chem 241, 257 (1966).

Skellysolve B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1

$PGF_{2\alpha}$, 1,9-lactone (Formula XXII: $Z_1$ is cis—CH=CH—$(CH_2)_3$—, $R_8$ is hydroxy, $Y_1$ is trans—CH=CH—, $R_3$ and $R_4$ of the $L_1$ moiety and $R_5$ of the $M_1$ moiety are all hydrogen, and $R_7$ is n-butyl).

Refer to Chart A.

A. A solution of 35 mg. of $PGF_{2\alpha}$, 39 mg. of triphenylphosphine, and 33 mg. of 2,2'-dipyridyl disulfide in 0.5 ml. of dry, oxygen-free benzene is stirred at 25° C. for 18 hr. The resulting mixture is thereafter diluted with 25 ml. of benzene and heated at reflux for 24 hr. Thin layer chromatographic analysis in (15 percent acetone and methylene chloride) indicates a mixture of $PGF_{2\alpha}$, 1,9-lactone and 1,15-lactone in a ratio of about 8 to one. Pure product is then isolated from the reaction mixture employing silica gel chromatographic separation.

B. Formation of $PGF_{2\alpha}$, 1,9-lactone employing an 11,15-bis ether starting material.

1. a solution of 496 mg. of $PGF_{2\alpha}$, 1,11-bis(α-ethoxyethyl ether) in 5 ml.of anhydrous, oxygen free xylene is treated with 330 mg. of 2,2-dipyridyl disulfide and 393 mg. of triphenylphosphine. This mixture is then stirred for 2.5 hr. at 25° C. under an atomosphere of nitrogen. The resulting mixture is then diluted with 250 ml. of dry, oxygen-free xylene and heated at reflux for 18 hr. Followed by removal of xylene under reduced pressure, the residue is diluted with aqueous sodium bicarbonate and extracted with hexane. The combined hexane layers are washed with brine, dried over anhydrous sodium sulfate, and concentrated.

2. The crude product of (1) above is then dissolved in 40 ml. of tetrahydroufran and 30 ml. of water. This mixture is then treated with 6 ml. of 85 percent phosphoric acid and stirred under a nitrogen atmosphere at 40° C. for 2.5 hr. After then removing most of the tetrahydrofuran at reduced pressure, the residue is diluted with ethyl acetate and aqueous sodium bicarbonate and the title product is isolated by extraction with ethyl acetate. The combined organic phases are then washed with aqueous sodium bicarbonate, and brine; dried over magnesium sulfate; and concentrated. Crude product is then chromatographed on 50 g. of neutral silica gel. The column is packed with ethyl acetate and hexane (1:1) and eluted with pure ethyl acetate. Thereupon 500 mg. of pure product are obtained. This material is then rechromatographed on a silica gel column packed in 10 percent acetone and methylene chloride and eluted with 10 to 35 percent acetone in methylene chloride. Thereupon 210 mg. of pure $PGF_{2\alpha}$, 1,9-lactone are obtained. Infrared absorptions are observed at 3460, 3000, 1730, 1705, 1335, 1285, 1230, 1210, 1180, 1150, 1085, 1065, 1025, 970, and 720 $cm.^{-1}$. Mass spectrum shows peaks at 318, 300, 289, 274, 247, 229, 219, and 192.

Following the procedure of Example 1, but employing in each of the various $PGF_{2\alpha}$-type compounds described by formula 1 in place of $PFG_{2\alpha}$, there are obtained each of the various corresponding $PGF_{2\alpha}$, 1,9-lactones.

EXAMPLE 2

$8\beta,12\alpha$-$PGF_{2\alpha}$, 1,9-lactone.

(Formula XXIV: $Z_1$, $R_8$, $Y_1$, $M_1$, $L_1$, and $R_7$ are as defined in Example 1).

Refere to Chart A.

Following the procedure of either Example 1, part A or Example 1, part B, $8\beta,12\alpha$-$PGF_{2\alpha}$or an $8\beta,12\alpha$-$PGF_{2\alpha}$, 11,15-bis ether, respectively, is transformed to the title product.

Following the procedure of Example 2, but employing each of the various $8\beta,12\alpha$-$PGF_{2\alpha}$-type compounds described by formula 1 in place of $8\beta,12\alpha$-$PGF_{2\alpha}$, there are obtained each of the various corresponding $8\beta,12\alpha$-$PGF_{2\alpha}$-type, 1,9-lactones.

EXAMPLE 3

$PFG_{2\beta}$, 1,9-lactone (Formula XXII: $Z_1$, $R_8$, $Y_1$, $M_1$, $L_1$, and $R_7$ are as defined in Example 1).

Refer to Chart A.

Following the procedure of Example 1, part A or Example 1, part B, but using $PGF_{2\beta}$ or a $PFG_{2\beta}$11,15-bis ether there is prepared the title product.

Following the procedure of Example 3, but employing each of the various $PGF_{2\beta}$-type compounds described by formula 1 in place of $PGF_{2\beta}$, there are obtained each of the various corresponding $PGF_{2\beta}$-type, 1,9-lactones.

EXAMPLE 4

$8\beta,12\alpha$-$PGF_{2\beta}$, 1,9-lactone (Formula XXIV: $Z_1$, $R_8$, $Y_1$, $M_1$, $L_1$, and $R_7$ are the same as in Example 1).

Refer to Chart A.

Following the procedure of Example 1, part A, or Example 1, part B, but using $8\beta,12\alpha$-$PGF_{2\beta}$ or an $8\beta,12\alpha$-$PGF_{2\beta}$,11,15-bis ether there is obtained the title product.

Following the procedure of Example 4, but employing each of the various $PGF_{2\beta}$-type compounds described by formula1 in place of $8\beta,12\alpha$-$PFG_{2\beta}$, there are obtained each of the various corresponding $8\beta,12\alpha$-$PGF_{2\beta}$-type, 1,9-lactones.

EXAMPLE 5

11-Deoxy-$PGF_{2\alpha}$, 1,9-lactone (Formula XXII: $Z_1$, $Y_1$, $M_1$, $L_1$, and $R_7$ are as defined in Example 1, and $R_8$ is hydrogen).

Refer to Chart A.

Following the procedure of Example 1, part A or Example 1, part B, but employing 11-deoxy-$PGF_{2\alpha}$or an 11-deoxy-$PGF_{2\alpha}$, 15-ether there is obtained the title product.

Following the procedure of Example 5, but employing each of the various 11-deoxy-$PGF_{2\alpha}$-type compounds described by formula 1 in place of 11-deoxy-$PGF_{2\alpha}$, there are obtained each of the various corresponding 11-deoxy-$PGF_{2\alpha}$-type, 1,19-lactones.

EXAMPLE 6

11-Deoxy-$8\beta,12\alpha$-$PGF_{2\alpha}$, 1,9-lactone (Formula XXIV: $Z_1$, $R_8$, $Y_1$, $M_1$, and $R_7$ are as defined in Example 5).

Refer to Chart A.

Following the procedure of Example 1, part A, or Example 1, part B, but employing 11-deoxy-$8\beta,12\alpha$-$PGF_{2\alpha}$or an 11-deoxy-$8\beta,12\alpha$-$PGF_{2\alpha}$,15-ether, respectively, there is obtained the title product.

Following the procedure of Example 6, but employing each of the various 11-deoxy-$8\beta,12\alpha$-$PGF_{2\alpha}$-type compounds described by formula 1 in place of 11-deoxy-$8\beta,12\alpha$-$PGF_{2\alpha}$, there is obtained each of the various corresponding 11-deoxy-$8\beta,12\alpha$-$PGF_{2\alpha}$-type, 1,9-lactones.

EXAMPLE 7

11-deoxy-$PGF_{2\beta}$, 1,19-lactone (Formula XXII: $Z_1$, $R_8$, $7_1M_1$, $L_1$, and $R_7$ are as defined in Example 5).

Refer to Chart A.

Following the procedure of Example 1, part A or Example 1, part B, but employing 11-deoxy-$PGF_{2\alpha}$or an 11-deoxy-$PGF_{2\beta}$, 15-ether, respectively, there is obtained the title product.

Following the procedure of Example 7, but employing each of the various 11-deoxy-$PGF_{2\beta}$-type compounds described by formula I in place of 11-deoxy-$PGF_{2\beta}$, there is obtained each of the various corresponding 11-deoxy-$PGF_{2\beta}$-type, 1,9-lactones.

EXAMPLE 8

11-deoxy-$8\beta,12\alpha$-$PGF_{2\beta}$, 1,9-lactone

Formula XXIV: $Z_1$, $R_8$, $Y_1$, $M_1$, $L_1$, and $R_7$ are as defined in Example 5).

Refer to Chart A.

Following the procedure of Example 1, part A or Example 1, part B, but employing 11-deoxy-$8\beta,12\alpha$-$PGF_{2\beta}$ or an 11-deoxy-$8\beta,12\alpha$, 15-ether, respectively, there is obtained the title product.

Following the procedure of Example 8, but employing each of the various 11-deoxy-$8\beta,12\alpha$-$PGF_{2\beta}$-type compounds described by formula I in place of 11-deoxy-$8\beta,12\alpha$-$PGF_{2\beta}$, there is obtained each of the various corresponding 11-deoxy-$8\beta,12\alpha$-$PGF_{2\beta}$-type 1,9-lactones.

EXAMPLE 9

$PGD_2$, 1,9-lactone (Formula XXXVII: $Z_1$, $Y_1$, $M_1$, $L_1$, and $R_7$ are as defined in Example 1).

Refer to chart B.

A. $PGF_{2\alpha}$(2 g.) in 15 ml. of methylene chloride is mixed with n-butylboronic acid (688 mg.). This reaction mixture is then heated at reflux with vigorous stirring adding methylene chloride and 5 ml. aliquots to replace amounts allowed to escape by evaporation. After 25 min., 10 ml. of dihydropyran is added to the reaction mixture with 150 mg. of pyridine hydrochloride. After about 20 hr. etherification is complete and methylene chloride is removed under reduced pressure. The residue is then diluted with 30 ml. of methanol and 13 ml. of 3N aqueous potassium hydroxide. The resulting clear yellow solution is then allowed to stand for 2 hr., then treated with 5 ml. of a 30 percent solution of aqueous hydrogen peroxide and 30 ml. of water. Thereafter the methanol is removed under reduced pressure and the aqueous residue diluted with 100 ml. of water and extracted twice with diethyl ether. The aqueous layer is then acidified with 25 ml. of 2N aqueous potassium bisulfate and extracted with ethyl acetate. The combined organic extracts are then washed with brine and dried over sodium sulfate. Removal of the solvent under reduced pressure yields 3.3 g. of an oil which is then chromatographed on 100 g. of acid washed silica gel. Eluting with 75 percent ethyl acetate in hexane, 2.0 g. of pure formula XXXIV $PGF_{2\alpha}$, 15-(tetrahydropyranyl ether) is obtained.

B. A solution of 1.7 g. of the reaction product of part A, 1.52 g. of triphenylphosphine, and 1.28 g. of 2,2'-dipyridyl disulfied in 10 ml. of dry, oxygen-free benzene is stirred at room temperature overnight. Then the solution is diluted with 1 l. of oxygen free benzene and the mixture is refluxed under a nitrogen atmosphere for 23 hr. After cooling to room temperature, the mixture is concentrated to an oil. The crude product thus obtained is chromatographed on a column of 450 g. of silica gel, packed with 30 percent ethyl acetate in hexane. Eluting with 50 to 60 percent ethyl acetate in hexane, 1.23 g. of the formula XXXV 1,9-lactone is obtained. Silica gel $R_f$ is 0.26 in 50 percent ethyl acetate in hexane. Infrared absorptions are observed at 3500, 2980, 2910, 1750, 1580, 1530, 1450, 1420, 1360, 1345, 1320, 1260, 1230, 1200, 1180, 1120, 1080, 1020, 990, 970, 940, 905, 870, and 815 cm.$^{-1}$.

C. A solution of 5.5 g. of the reaction product of part B in acetone is cooled to −30° C. Thereupon 3.6 ml. of the Jones reagent is added and the solution is maintained at −30° C. for 1 hr. Thereafter, 6 ml. of isopropyl alcohol is added and the solution is stirred for another 30 min. at −30° C. The mixture is then poured into 600 ml. of ice water and extracted with diethyl ether and hexane (1:2). This organic extract is then washed three times with brine, dried over magnesium sulfate, and concentrated to an oil (5 g.). This crude oil is then chromatographed on 375 g. of silica gel, packed with 10 percent ethyl acetate in hexane, and eluted with 25 percent ethyl acetate and hexane. Thereupon, 3.4 g. of the formula XXXVI compound are obtained as a colorless oil. Silica gel $R_f$ if 0.50 in ethyl acetate, hexane, and acetic acid (35:14:1). Infrared absorptions are observed at 2980, 2910, 1750, 1450, 1360, 1340, 1260, 1230, 1200, 1180, 1130, 1080, 1020, 990, and 870 cm$^{-1}$.

D. A solution of 0.5 g. of the reaction product of part C in 25 ml. of a mixture of tetrahydrofuran, water, and acetic acid (1:3:6) is warmed to 40° C. for 1 hr. The mixture is then poured into 100 ml. of cold brine and extracted three times with ethyl acetate and hexane (1:1). The combined organic extract is then washed with brine and ice cold saturated sodium bicarbonate, dried over sodium sulfate, and concentrated to yield 0.37 g. of an oil. This sulfate, and concentrated to yield 0.37 g. of an oil. This oil crude oil is then chromatographed on 20 g. of silica gel, packed with 20 percent ethyl acetate and hexane. Eluting with 40 percent ethyl acetate in hexane 0.27 g. of $PGD_2$, 1,9-lactone is obtained as a light yellow oil. Silica gel $R_f$ is 0.37 in 50 percent ethyl acetate in hexane. Infrared absorptions are observed at 3460, 3000, 2960, 2920, 2860, 1740, 1580, 1560, 1450, 1365, 1335, 1265, 1230, 1205, 1175, 1130, 1070, 1050, 1025, 970, and 945 cm.$^{-1}$. Characteristic infrared absorptions are observed 5.40, 4.0, and 0.9 δ. The mass spectrum shows parent peak at 406.2522 and other peaks at 388, 378, 373, and 335.

Following the procedure of Example 9, but employing each of the various PGD-type compounds described by formula I in place of $PGD_2$, there are obtained each of the various corresponding PGD-type, 1,9-lactones.

EXAMPLE 10

8β,12 α-$PGD_2$, 1,9-lactone

Refer to Chart B.

Following the procedure of Example 9, but employing 8β,12α-$PGF_{2\alpha}$ in place of $PGF_{2\alpha}$, there is obtained the title product.

Following the procedure of Example 10, but employing each of the various 8β,12α-PGD-type compounds described by formula I in place of 8β,12α-$PGD_2$, there is obtained each of the various corresponding 8β,12α-PGD-type, 1,9-lactones.

EXAMPLE 11

9β-$PGD_2$, 1,9-lactone (Formula CLXXXVIII: $Z_1$, $Y_1$, $M_1$, $L_1$, and $R_7$ are defined in Example 1).

Refer to Chart P.

A. A solution of 2.5 g. of 11β-$PGF_{2\beta}$ methyl ester and 0.83 g. of n-butylboronic acid in 75 ml. of ethylene chloride is refluxed. As 8 ml. aliquots of methylene chloride are removed by distillation, an additional 8 ml. of methylene chloride is added to the reaction mixture. After cooling to ambient temperature, 15 ml. of dihydropyran in 0.2 g. of pyridine hydrochloride are added. This mixture is then allowed to stir for 12 hr. Thereafter the methylene chloride is evaporated under reduced pressure and a cooled mixture of 10 ml. of 30 percent hydrogen peroxide and 50 ml. of 1N sodium bicarbonate is added. The resulting mixture is then stirred for 45 min. Ethyl acetate is then added and the reaction mixture extracted several times with ethyl acetate. The combined organic extract is then washed with brine, dried over sodium sulfate, and concentrated to an oil. This crude product is then chromatographed on 200 g. of silica gel packed with 50 percent ethyl acetate and Skellysolve B and eluted with 50 to 70 percent ethyl acetate in Skellysolve B. Thereupon, 1.8 g. of the methyl ester of the formula CLXXXV compound is obtained as a colorless oil. Silica gel $R_f$ is 0.33 in 70 percent ethyl acetate in hexane. Infrared absorptions are observed 3500, 2980, 2900, 1740, 1460, 1440, 1320, 1200, 1130, 1110, 1090, 1080, 1020, 980, and 870 cm.$^{-1}$.

B. The methyl ester of part A (0.75 g.) in 30 ml. of 3N sodium hydroxide and methanol (1:1) is stirred for 90 min. Thereupon, the mixture is poured into 50 ml. of ice-cold 2N sodium bisulfate and extracted twice with ethyl acetate. The combined organic extracts are then washed with brine, dried over sodium sulfate, and concentrated to yield 0.70 g. of the formula CLXXXV free acid. Silica gel $R_f$ is 0.36 in the AIX solvent system.

C. The reaction product of part B (1.0 g.), 0.90 g. of triphenylphosphine, in 0.75 g. of 2,2'-dipyridyl disulfide in 15 ml. of oxygen free benzene is allowed to stir at room temperature overnight under a nitrogen atmosphere. Thereafter the mixture is diluted with 200 ml. of oxygen free toluene and the solution is warmed to reflux temperature for 30 hr. After cooling to room temperature, the solvent is evaporated under reduced pressure to yield a yellow oil. This crude yellow oil is then chromatographed on 300 g. of silica gel, packed with 15 percent ethyl acetate and hexane and eluted with 25 percent ethyl acetate and hexane. Thereupon, 0.50 g. of the formula CLXXXVI lactone is obtained as an oil. Silica gel $R_f$ is 0.25 and 0.32 in 25 percent ethyl acetate in hexane. Infrared absorptions are observed at 3550, 3000, 2920, 1750, 1460, 1420, 1350, 1310, 1260, 1235, 1200, 1140, 1115, 1080, 1020, 985, and 870 cm.$^{-1}$.

D. A solution of 0.45 g. of the reaction product of part C and 25 ml. of acetone is cooled to −25° C. Thereupon 0.50 ml. of Jones reagent is added and after 45 min. at −25° to −20° C., 0.5 ml. of isopropanol is added. After an additional 20 min. the mixture is then poured into 100 ml. of ice-cold brine and extracted 3 times with ethyl acetate. The combined ethyl acetate extract is then washed twice with brine, dried over sodium sulfate, and concentrated to yield 0.43 g. of a formula CLXXXVII compound as an oil. Silica gel $R_f$ is 0.50 in 25 percent ethyl acetate in hexane. A solution of this oil and 25 ml. of a mixture of tetrahydrofuran, water, and acetic acid (1:3:6) is warmed to 40° C. for 90 min. Thereupon the solution is poured into 100 ml. of cold brine and extracted with 375 ml. of 30 percent ethyl acetate in hexane. The combined organic extract is then washed with brine, dried over sodium sulfate, and concentrated to an oil. This crude oil is then chromatographed on 40 g. of silica gel packed with 15 percent ethyl acetate and hexane and diluted with 30 percent ethyl acetate and hexane. Thereupon 0.30 g. of purified product is obtained, which yields 165 mg. of colorless needle crystals. Melting point is 54°-55° C. Silica gel $R_f$ is 0.25 in 30 percent ethyl acetate in hexane. Infrared absorptions are observed at 3550, 3000, 2920, 1750, 1460, 1420, 1350, 1320, 1270, 1230, 1150, 1075, 1070, 970, and 975 cm.$^{-1}$. NMR absorptions are observed at 5.50, 5.10, and 4.15 δ. The mass spectrum shows parent peak 334.2173.

Following the procedure of Example 11, but employing each of the various 9β-PGD-type compounds described by formula I in place of 9β-$PGD_2$, there are obtained each of the corresponding 9β-$PGD_1$-type lactones.

EXAMPLE 12

8β,9β,12α-$PGD_2$, 1,9-lactone (Formula CLXXIV: $Z_1$, $Y_1$, $M_1$, $L_1$, and $R_7$ are as defined in Example 1).

Refer to Chart N.

A. A solution of 0.60 g. of 8β,12α-$PGF_{2\beta}$, 1,9-lactone (Example 4) in 70 ml. of dry acetone is cooled to −20° C. Thereupon, 2.8 ml. of trimethylsilyldiethylamine is added. After 30 min., another 2.8 ml. of trimethylsilydiethylamine is added. After 1.5 hr., the mixture is cooled to −70° C. and 150 ml. of cooled (−70° C.) diethyl ether is added. This mixture is then poured into 100 ml. of ice-cold saturated sodium bicarbonate and extracted 3 times with diethylether. The combined etheral extracts are then washed with ice-cold saturated sodium bicarbonate and brine, dried over magnesium sulfate, and concentrated to yield $PGF_{2\beta}$, 1,9-lactone, 15-trimethylsilyl ether (Formula CLXXII).

B. Employing the Collins Reagent the reaction product of part A of this example is oxidized to the corresponding formula CLXXIII compound.

C. Following the procedure of Example 9, part D, the reaction product of part B of this example is hydrolyzed to the title product.

Following the procedure of Example 12, but employing each of the various 8β,9β,12α-PGD-type compounds described by formula I in place of 8β,9β,12α-$PGD_2$, there are obtained each of the various 8β,9β,12α-PGD-type, 1,9-lactones.

EXAMPLE 13

$PGF_{2\alpha}$, 1,11-lactone (Formula CLXVIII: $Z_1$, $Y_1$, $M_1$, $L_1$, and $R_7$ are as defined in Example 1, and $W_1$ is

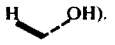

Refer to Chart K.

A. The first method of Chart K:

1. A stirred solution of one g. of $PGD_2$ (0° C.) in 25 ml. of anhydrous pyridine is treated with 3 g. of triphenylsilyl chloride and the resulting mixture then stirred for 6 hr. at 25° C. under a nitrogen atmosphere. This reaction mixture is then recooled to 0° C., diluted with 100 ml. of tetrahydrofuran (at 0° C.) and 40 ml. of water (at about 40° C.). This mixture is then stirred 45 min. at ° C. The resulting mixture is then poured into brine, acidified with 325 ml. of 1N sodium bisulfate, and extracted with ethyl acetate in hexane (1:1). The combined extracts are then washed with brine, dried over sodium sulfate, and concentrated. The crude product, thusly obtained, is chromatographed on 300 g. of silica gel, packed with 10 percent ethyl acetate in hexane and eluted with 10 to 20 percent ethyl acetate in hexane. Thereby, 2.15 g. of the formula CXLII $PGD_2$, 9,15-bis-(triphenylsilyl ether) are obtained. Infrared absorptions are observed 3300, 3100, 2700, 1750, 1720, 1600, 1490, 1430, 1370, 1240, 1115, 1040, 1000, 970, 740, 710, and 700 cm.$^{-1}$. NMR absorptions are observed at 10.75. 7.9–7.2, 5.75–5.05, and 4.75–4.15 δ.

2. To a stirred solution of 4.10 g. of the reaction product of subpart (1) at 0° C. in 250 ml. of methanol is added 3.0 g. of sodium borohydride in 100 mg. portions over a period of 15 min. After stirring an additional 15 min. at 0° C., the reaction mixture is then carefully poured into a rapidly stirred mixture of ice, water, dilute sodium bisulfate, and 50 percent ethyl acetate in hexane. After separation of phases, the aqueous layer is extracted twice with ethyl acetate in hexane (1:1). The combined organic layer is then washed with brine, dried over sodium sulfate, and concentrated under reduced pressure. The crude product is then chromatographed on 450 g. of an acid washed silica gel. The column is packed with 10 percent ethyl acetate in hexane and eluted with 20 percent ethyl acetate in hexane. Thereupon, 2.90 g. of the formula CXLIV $PGF_{2\alpha}$, 9.15-bis-(triphenylsilyl ether) is obtained.

3. A solution of 2.90 g. of the reaction product of subpart (2), 1.10 g. of 2,2'-diphyridylsulfide, and 1.31 g. of triphenylphosphine in 40 ml. of dry oxygen-free xylene is stirred at 25° C. under nitrogen atmosphere for 10 hr. The resulting mixture is then diluted with 800 ml. of xylene and heated at reflux for 24 hr. After cooling, the xylene is removed under reduced pressure and a dark red residue is then chromatographed on 450 g. of neutral silica gel. The column is packed and eluted with benzende. Thereupon, 2.20 g. of the formula CXLV $PGF_{2\alpha}$, 1,11-lactone. 9,15-bis(triphenylsilyl ether) is obtained. Infrared absorptions are observed at 3100, 3050, 1730, 1590, 1480, 1440, 1420, 1325, 1260, 1220, 1180, 1140, 1110, 1000, 970, 905, 900, 875, 740, 710, and 700 cm.$^{-1}$.

4. A stirred mixture of 2.20 g. of the reaction product of subpart (3), 100 ml. of tetrahydrofuran, 80 ml. of water, and 20 ml. of 85 percent phosphoric acid is heated at 45° C. for 2 hr. After concentrating the reaction mixture under reduced pressure, water is added and the product is isolated by extraction with a mixture of ethyl acetate and hexane (3:1). The combined extracts are then washed with aqueous sodium bicarbonate and brine, dried over magnesium sulfate, and evaporated. Crude product is then chromatographed on 125 g. of neutral silica gel, packed with 25 percent ethyl acetae in hexane, and eluted with 40 to 70 percent ethyl acetate in hexane. Thereupon 615 mg. of title product is obtained. Infrared absorptions are observed at 3400, 3000, 2920, 2850, 1730, 1710, 1450, 1355, 1335, 1270, 1225, 1185, 1145, 1100, 1085, 1005, 965, and 705 cm.$^{-1}$. The mass spectrum shows parent peak 480.3073 and other peaks at 465, 409, 390, 375, 319, and 199.

B. The second method of Chart K:

1. Following the procedure of Example 9, part A, $PGF_{2\alpha}$ is transformed to $PGF_{2\alpha}$, 15-(tetrahydropyranyl ether).

2. $PGF_{2\alpha}$, 15-(tetrahydropyranyl ether), 2 g., in acetone (75 ml.) is cooled to −45° C. and thereafter treated with 1.2 ml. of the Jones reagent. The resulting mixture is then stirred for 30 min. at −35 to 45° C. and thereafter treated with 0.5 ml. of isopropanol. Stirring continues an additional 15 min. The resulting mixture is then poured into a mixture of ice, water, and diethyl ether. This mixture is then extracted with diethyl ether and combined ethereal extracts are then washed with brine and dried over sodium sulfate. After filtration, removal of solvent proceeds by rotary evaporation. Crude $PGD_2$, 15-(tetrahydropyranyl ether), 1.8 g., thereby obtained, is chromatographed on 360 g. of acid washed silica gel eluting with 45 percent ethyl acetate in hexane. 800 mg. of pure compound is thereby obtained.

3. Following the procedure of Example 13, part A, subpart A, the reaction product of subpart (2) of this part is silylated at C-9, preparing $PGD_2$, 15-(tetrahydropyranyl ether), 19-(triphenylsilyl ether).

4. Following the procedure of Example 13, part A, subpart 2, the reaction product of subpart 3 above is reduced and chromatographed, preparing a formula CXLIV compound.

5. Following the procedure of Example 13, part A, subpart 3, the reaction product of subpart 4 of this part is lactonized, preparing $PGF_{2\alpha}$, 1,11-lactone, 15-(tetrahydropyrayl ether 9-triphenylsilyl ether).

6. The reaction product of subpart 5 of this part is then dissolved in tetrahydrofuran (25 ml.) and treated with a solution of tetra-n-butylammonium fluoride in tetrahydrofuran. This reaction mixture is then stirred at 65° C. for 2 hr. and thereafter cooled to ambient temperature. The resulting product is then concentrated under reduced pressure, diluted with brine, and extracted with ethyl acetate. The organic extract is then washed with 2M aqueous potassium bisulfate and brine and dried over magnesium sulfate. Concentration under reduced pressure yields $PGF_{2\alpha}$, 1,11-lactone, 15(tetrahydropyranyl ether).

7. Following the procedure of Example 13, part A, subpart 4, the reaction product of subpart 6 of this part is transformed to the title product by hydrolysis.

Following the procedure of Example 13, but employing each of the various $PGF_\alpha$-type compounds described by formula I in place of $PGF_{2\alpha}$, there is obtained each of the various corresponding $PGF_\alpha$-type, 1,11-lactones.

EXAMPLE 14

8β,12α-$PGF_{2\alpha}$,1,11-lactone (Formula CXXXVI: $Z_1$, $Y_1$, $M_1$, $L_1$, and $R_7$ are as defined in Example 1 and $W_1$ is

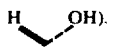

Refer to Charts J and K.

A. Following the procedure of Example 13, part A, employing 8β,12α-$PGD_2$, in place of $PGD_2$, there is obtained the title product.

B. The method of Chart J:

1. Following the procedure of Example 9, part A, 8β,12α-$PGF_{2\alpha}$ is transformed to 8β,12α-$PGF_{2\alpha}$,15-(tetrahydropyranyl ether), formula CXXXII.

2. Following the procedure of Example 12, part A the reaction product of subpart 1 of this part is selectively silylated at C-9.

3. Following the procedure of Example 1, part A, the reaction product of subpart (2) of this part is 1,11-lactonized, preparing a formula CXXXIV compound.

4. Following the procedure of Example 13, part B, subpart 6, the reaction product of subpart 3 or this part is selectively hydrolyzed at the C-9 positive, preparing 8β,12α-$PGF_{2\alpha}$, 1,11-lactone 15-(tetrahydropyranyl ether, a formula CXXXV compound.

5. Following the procedure of Example 13, part B, subpart 7, but employing the reaction product of subpart 4 of this part the title product is prepared.

Following the procedure of Example 14, but employing each of the various 8β,12α-$PGF_\alpha$-type compound described by formula I in place of 8β,12α-$PGF_{2\alpha}$, , there are obtained each of the various corresponding 8β,12α-$PGF_\alpha$-type, 1,11-lactones.

EXAMPLE 15

$PGE_2$, 1,11-lactone (Formula CXXII: $Z_1$, $Y_1$, $M_1$, $L_1$, and $R_7$ are as defined in Example 1).

Refer to Charts H or K.

A. Following the procedure of Example 9, part C, the reaction product of Example 13, part B, subpart 6, is oxidized to the formula CXXI PGE-type, 1,11-lactone.

B. Following the procedure of Example 13, part B, subpart 7, the reaction product of part A above is hydrolyzed to the title compound.

Following the procedure of Example 15, but employing each of the various $PGF_{2\alpha}$-type, 1,11-lactone, 15-(tetrahydropyranyl ethers) corresponding to each of the various $PGF_{2\alpha}$, 1,11-lactones described following Example 13, there are obtained each of the corresponding $PGE_2$, 1,11-lactones.

EXAMPLE 16

8β,12α-$PGE_2$, 1,11-lactone (Formula CXXXVI: $Z_1$, $Y_1$, $M_1$, $L_1$, and $R_7$ are as defined in Example 1, and $W_1$ is

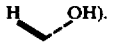

Refer to Charts J and K.

A. Following the procedure of Example 9, part C, the reaction product of Example 14, part B, subpart 4, is transformed to 8β,12α-$PGE_2$, 1,11-lactone, 15-(tetrahydropyranyl ether).

B. Following the procedure of Example 13, part B, subpart 7, the reaction product of part A above is transformed to the title product.

Following the procedure of Example 16, but employing each of the various formula CXXXV $PGF_\alpha$-type, 1,11-lactone, 15-(tetrahydropyranyl ethers) in place of the reaction product of Example 14, part B, subpart 4, there are obtained each of the various corresponding 8β,12α-PGE-type, 1,11-lactones.

EXAMPLE 17

$PGF_{2\beta}$, 1,11-lactone (Formula CXXIII: $Z_1$, $Y_1$, $M_1$, $L_1$, and $R_7$ are as defined in Example 1).

Refer to Charts H and K.

Following the procedure of Example 13, part B, subpart 4, but employing the reaction product of Example 15, there is obtained the title product.

Following the procedure of Example 17, but employing each of the various PGE-type, 1,11-lactones described following Example 15, in place of $PGE_2$, 1,11-lactone, there are obtained each of the various $PGF_\beta$-type, 1,11-lactones.

EXAMPLE 18

$8\beta,12\alpha$-$PGF_{2\beta}$ (Formula CXXXVI: $Z_1$, $Y_1$, $M_1$, $L_1$, and $R_7$ are as defined in Example 1, and $W_1$ is

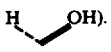

Refer to Charts J and K.

Following the procedure of Example 13, part B, subpart 4, but employing the reaction product of Example 16, there is prepared the title product.

Following the procedure of Example 18, but employing each of the various $8\beta,12\alpha$-PGE-type, 1,11-lactones described following Example 16, in place of $8\beta,12\alpha$-$PGE_2$, there is obtained each of the various corresponding $8\beta,12\alpha$-$PGF_\beta$-type, 1,11-lactones.

EXAMPLE 19

15-Methyl-$PGF_{2\beta}$, 1,11-lactone (Formula CXCVI: $Z_1$, $Y_1$, $L_1$, and $R_7$ are as defined in Example 1, and $R_5$ of the $M_{11}$ moiety is methyl).

Refer to Chart R.

A. 15-Methyl-$PGF_{2\alpha}$ is reacted with one equivalent of p-phenylbenzoyl chloride. The reaction is monitored by silica gel thin layer chromatography and when the acylation at C-11 is complete, the reaction is terminated and the formula CXCII compound recovered.

B. Following the procedure of Example 13, part A, subpart 2, t-butyldimethylsilyl chloride is employed to transform the reaction product of part A above to the formula CXCIII 9,15-bis-(t-butyldimethylsilyl) derivative.

C. The reaction product of part B is deacylated employing potassium hydroxide in aqueous methanol. Pure formula CXCIV compound is thereby recovered.

D. Following the procedure of Example 1A, the reaction product of part C above is 1,11-lactonized, forming a formula CXCV compound.

E. The formula CXCV compound is then hydrolyzed following the procedure of Example 13, part A, subpart 4, to the title product.

Following the procedure of Example 19, but employing each of the various 15-methyl-$PGF_{2\alpha}$-type compounds described by formula XLI in place of 15-methyl-$PGF_{2\alpha}$, there are obtained each of the various corresponding 15-methyl-PGA-type, 1,11-lactones.

EXAMPLE 20

$PGF_{2\alpha}$, 1,15-lactone (the $8\alpha,12\beta$-isomer of Formula LXIV: $Z_1$, $Y_1$, $R_5$, $L_1$, and $R_7$ are defined in Example 1).

Refer to chart D.

A. A solution of 5.5 g. of $PGF_{2\alpha}$ and 1.79 g. of n-butylboronic acid in 150 ml. of methylene chloride is heated at reflux for 15 min. Thereafter about half the methylene chloride is removed by distillation at atmospheric pressure and additional methylene chloride added to restore the volume to 150 ml. This distillation and replacement of methylene chloride is then repeated 3 times, after which all solvent is then removed under reduced pressure. Thereupon, crude formula LXII compound is obtained.

B. The reaction product of pair A is then dissolved in 180 ml. of anhydrous, oxygen-free xylene and treated with 5.128 g. of 2,2'-dipyridyl disulfide, followed by addition of 6.27 g. of triphenylphosphine. After 18 hr. at 25° C. under a nitrogen atmosphere the above solution is diluted with 300 ml. of oxygen free xylene and thereafter added dropwise over a 10 hr. period to 3.2 l. of vigorously stirred refluxing xylene under a nitrogen atmosphere. After the addition is complete, 100 ml. of xylene is distilled off and the solution is heated at reflux for 24 hrs. The reaction mixture is then cooled and the xylene removed under reduced pressure, preparing a formula LXIII compound.

C. The reaction product of part B is then taken up in 500 ml. of tetrahydrofuran and treated with 10 ml. of 30 percent hydrogen peroxide and 100 ml. of saturated aqueous sodium bicarbonate. This mixture is then stirred vigorously for 30 min. at 35° C. and then concentrated under reduced pressure. The residue is then taken up in brine and ethyl acetate and extracted thoroughly with ethyl acetate. The combined organic layer is then washed with 1N auqoues potassium bisulfate, water, aqueous sodium bicarbonate, and brine. After drying over sodium sulfate, removal of the solvent affords a viscous yellow oil which is chromatographed on 500 g. of acid washed silica gel. The column is packed with 25 percent ethyl acetate and hexane and eluted with 50 percent ethyl acetate and hexane. Title product is then crystallized from 40 ml. of diethylether and hexane (1:1), affording 1.559 g. of title product. Melting point is 110°–111° C. Infrared absorptions are observed at 3500, 3370, 3290, 3010, 1700, 1320, 1310, 1290, 1260, 1105, 1080, 1055, 970, and 730 $cm.^{-1}$. NMR absorptions are observed 6.00–5.75, 5.75–4.95, 4.30–3.85, and 2.65 δ. The mass spectrum shows parent peak 480.3102 and other peaks at 465, 436, 409, 390, 380, 364, 238, and 217.

Following the procedure of Example 20, but employing each of the various $PGF_\alpha$-type compounds described by formula 1 in place of $PGF_{2\alpha}$, there are obtained each of the various corresponding $PGF_{60}$-type, 1,15-lactones.

EXAMPLE 21

$8\beta,12\alpha$-$PGF_{2\alpha}$, 1,15-lactones

Refer to Chart D.

Following the procedure of Example 20, but employing $8\beta,12\alpha$-$PGF_{2\alpha}$ in place of $PGF_{2\alpha}$, there is obtained the title product.

Following the procedure of Example 21, but employing each of the various $8\beta,12\alpha$-$PGF_\alpha$-type compounds described by formula 1 in place of $8\beta,12\alpha$-$PGF_{2\alpha}$, there are obtained each of the various corresponding 8β,12α-$PGF_{\alpha}$-type, 1,15-lactones.

EXAMPLE 22

$PGE_2$, 1,15-lactone (Formula L: $Z_1$, $R_8$, $Y_1$, $R_5$, $L_1$, and $R_7$ are as defined in Example 1).

Refer to Chart C.

A. A solution of 1.7 g. of $PGF_{2\alpha}$, 1,15-lactone (formula XLVIII) in 45 ml. of anhydrous acetone is cooled under nitrogen to between −45° and −40° C. This solution is then treated with 4.5 ml. of trimethylsilyldiethylamine. After addition is complete, the mixture is stirred at −45° to −40° C. for 2 hrs. This mixture is then cooled to −78° C., diluted with 150 ml. of precooled diethyl ether, and poured into an ice-brine mixture. After extraction with hexane, the combined organic layers are washed with aqueous sodium bicarbonate and brine, dried over anhydrous sodium sulfate, and concentrated under reduced pressure. Thereby, 1.47 g. of a formula XLIX 11-trimethylsilyl compound is obtained.

B. The Collins reagent is prepared by adding 2.45 g. of dry chromium trioxide to a cold (0° C), stirred solution of 3.99 ml. of anhydrous pyridine in 120 ml. of methylene chloride. The resulting dark resolution is then stirred at 25° C. for 1 hr., then cooled to 0° C. A solution of the reaction product of part A in 6 ml. of methylene chloride is then added in one portion to the rapidly stirred Collins reagent. The ice bath is then removed and the reaction mixture is stirred an additional 20 min. The mixture is then poured into a column containing 150 g. of neutral silica gel. The column is then eluted with ethyl acetate yielding 1.357 g. of $PGE_2$, 1,15-lactone, 11-trimethylsilyl ether.

The reaction product of part B is then dissolved in 150 ml. of methanol, dilute with 60 ml. of aqueous 2.5 percent citric acid, and stirred at 25° C. for 30 min. After removal of about half of the methanol by evaporation at reduced pressure, the remaining solution is diluted with brine and extracted with ethyl acetate. The combined organic extracts are then washed with aqueous sodium bicarbonate and brine, dried over sodium sulfate, and concentrated.

The crude product is then crystallized from diethyl ether and hexane, yielding 6.08 g. of title product.

Following the procedure of Example 22, but employing each of the various $PGF_{\alpha}$-type, 1,15-lactones described following Example 20, in place of $PGF_{2\alpha}$, 1,15-lactone, there are obtained each of the various corresponding PGF-type, 1,15-lactones.

Alternatively, the title compound of Example 22 or each of the various compounds described in the paragraph are obtained directly by lactonization of $PGE_2$ or a PGE-type compound by the procedure described in Example 1, part A.

EXAMPLE 23

8β,12α-$PGE_2$, 1,15-lactone (Formula LXIX: $Z_1$, $Y_1$, $R_5$, $L_1$, and $R_7$ are as defined in Example 1).

Refer to Chart D or E.

A. The method of Chart D:

1. Following the procedure of Example 12, part A,8β,12α-$PGF_{2\alpha}$, 1,15-lactone (Example 20) is selectively silylated at C-9.

2. Following the procedure of Example 9, part A, the reaction product of subpart 1 above is transformed to the corresponding 11-(tetrahydropyranyl ether), a formula LXVI compound.

3. Following the procedure of Example 13, part B, subpart 6, the reaction product of subpart 2 above is selectively hydrolyzed at C-9 (the silyl ether), preparing $PGF_{2\alpha}$, 1,15-lactone, 11-(tetrahydropyranyl ether), a formula CLXVII compound.

4. Following the procedure of Example 9, part C, the reaction product of subpart 3 above is transformed to the corresponding $PGE_2$-type, 1,11-lactone (formula LXVIII).

5. Following the procedure of Example 9, part D, the reaction product of subpart 4 above is hydrolyzed to the title product.

B. Optionally, the title product is prepared by lactonization of 8β,12α-$PGE_2$, following the procedure of Example 1, part A.

Following the procedure of Example 23, but employing each of the various 8β,12α-$PGF_{\alpha}$-type 1,15-lactones described following Example 21 or each of the various 8β,12α-PGE-type compounds described by formula XLI, respectively, in place of 8β,12α-$PGF_{2\alpha}$, 1,15-lactone or 8β,12α-$PGE_2$, respectively, there are obtained each of the various 8β,12α-PGE-type, 1,15-lactones.

EXAMPLE 24

$PGF_{2\beta}$, 1,15-lactone (Formula LXXXV: $Z_1$, $R_8$, $Y_1$, $R_5$, $L_1$, and $R_7$ are as defined in Example 1).

Refer to Chart D or E.

Following the procedure of Example 13, part A, subpart 2, the reaction product of Example 22 is reduced and chromatographed to yield the title product.

Following the procedure of Example 24, but employing each of the various PGE-type 1,15-lactones described following Example 22, in place of $PGE_2$, 1,15-lactone, there are obtained each of the various corresponding $PGF_{\beta}$-type, 1,15-lactones.

EXAMPLE 25

8β,12α-$PGF_{2\beta}$, 1,15-lactone (Formula LXXXVI: $Z_1$, $R_8$, $Y_1$, $R_5$, $L_1$, and $R_7$ are as defined in Example 1).

Refer to Chart E.

Following the procedure described in Example 13, part A, subpart (2), 8β,12α-$PGE_2$, 1,15-lactone is reduced and chromatographed to yield the title product.

Following the procedure of Example 25, but employing each of the various 8β,12α-PGE-type, 1,15-lactone described following Example 23 in place of 8β,12α-$PGE_2$, 1,15-lactone, there are obtained each of the various corresponding 8β,12α-$PGF_{\beta}$-type, 1,15-lactones.

EXAMPLE 26

11-Deoxy-$PGE_2$, 1,15-lactone (Formula CV: $Z_1$, $Y_1$, $M_1$, $L_1$, and $R_7$ are as defined in Example 1).

Refer to Chart G.

Following the procedure of Example 1, part A, 11-deoxy-$PGE_2$ is lactonized to form the title product.

Following the procedure of Example 26, but employing each of the various 11-deoxy-PGE-type compounds described by formula I in place of 11-deoxy-$PGE_2$, there are obtained each of the various corresponding 11-deoxy-PGE-type, 1,15-lactones.

EXAMPLE 27

11-Deoxy-8β, 12α-$PGE_2$.

Refer to Chart G.

Following the procedure of Example 1, part A, 11-deoxy-8β,12α-$PGE_2$ is lactonized to the title product.

Following the procedure of Example 27, but employing each of the various 11-deoxy-8β,12α-PGE-type compounds described by formula I in place of 11-deoxy-8β,12α-$PGE_2$, there are obtained each of the various corresponding 8β,12α-11-deoxy-PGE-type, 1,15-lactones.

EXAMPLE 28

11-Deoxy-$PGF_{2\alpha}$ or 11-deoxy-$PGF_{2\beta}$ (Formula LXXXV: $Z_1$, $Y_1$, $R_5$, $L_1$, and $R_7$ are as defined in Example 1, and $R_8$ is hydrogen).

Refer to Chart E.

Following the procedure of Example 13, part A, subpart 2, 11-deoxy-$PGE_2$, 1,15-lactone is reduced and chromatographed yielding the title products.

Following the procedure of Example 27, but employing each of the various 11-deoxy-PGE-type, 1,15-lactones described following Example 26 in place of 11-deoxy-$PGE_2$, 1,15-lactone, there are obtained each of the various corresponding 11-deoxy-PGE-type, 1,15-lactones.

EXAMPLE 29

11-deoxy-8β,12α-$PGF_{2\alpha}$ or 11-deoxy-8β,12α-$PGF_{2\beta}$ (Formula LXXXVI: $Z_1$, $Y_1$, $R_5$, $L_1$, and $R_7$ are as defined in Example 1 and $R_8$ is hydrogen).

Refer to Chart E.

Following the procedure of Example 13, part A, subpart 2, 11-deoxy-8β,12α-$PGE_2$ is reduced and chromatographed yielding the title products.

Following the procedure of Example 29, but employing each of the various 8β,12α-PGE-type, 1,15-lactones described following Example 27, in place of 8β,12α-$PGE_2$, 1,15-lactone there are obtained each of the various corresponding PGE-type, 1,15-lactones.

EXAMPLE 30

$PGA_2$, 1,15-lactone (Formula XCII: $Z_1$, $Y_1$, $R_5$, $L_1$, and $R_7$ are as defined in Example 1).

Refer to Chart F or G.

A. The method of Chart F:

1. $PGE_2$, 1,15-lactone is dissolved in pyridine, combined with one equivalent of acetic anhydride and allowed to stand at 25° C. for 3 hrs. Thereupon, $PGE_2$, 1,15-lactone, 11-acetate is prepared. The reaction mixture is then cooled in an ice bath treated dropwise over 15 min. with 20 ml. of methanol. The ice bath is then allowed to melt and the temperature allowed to rise to ambient temperature. After an additional 18 hrs., the reaction mixture is then poured into a mixture of ice, diethyl ether, water, and 70 ml. of 2N aqueous potassium bisulfate. This mixture is then extracted thoroughly with diethyl ether and etheral extract washed with water, aqueous sodium bicarbonate and brine. This mixture is then dried over anhydrous sodium sulfate and concentrated under reduced pressure.

2. The crude product of subpart (1) above is then chromatographed on 100 g. of neutral silica gel. The column is packed and diluted with 15 percent ethyl acetate and hexane. Thereupon 46 mg. of title product are obtained. This material crystallizes on standing and recrystallization is effected from diethyl ether and hexane. The melting point is 60°-61.5° C. NMR absorptions are observed at 7.50-7.33 and 6.27 to 6.06. The mass spectrum shows parent peak 316.2074 and other peaks 298, 288, 259, 229, and 198. Infrared absorptions are observed at 3010, 1715, 1705, 1580, 1355, 1345, 1325, 1245, 1170, 1145, 1140, 1035, and 970 $cm.^{-1}$.

B. Alternatively, the title product is prepared from $PGA_2$ by direct lactonization according to Example 1, part A.

Following the procedure of Example 30, but employing each of the various PGE-type, 1,15-lactones described following Example 26 or PGA-type compounds described by formula LXI, respectively, there are obtained each of the various corresponding PGA-type, 1,15-lactones.

EXAMPLE 31

8β,12α-$PGA_2$, 1,15-lactone (Formula XCIV: $Z_1$, $Y_1$, $R_5$, $L_1$, and $R_7$ are as defined in Example 1).

Refer to Chart F or G.

Following the procedure of Example 30, part A, or Example 30, part B, 8β,12α-$PGE_2$, 1,15-lactone or 8β,12α-$PGA_2$, respectively, is transformed to the title product.

Following the procedure of Example 31, but employing each of the various 8β,12α-PGE-type, 1,15-lactones described following Example 27 or PGA-type compounds described by formula I, in place of 8β,12α-$PGF_2$, 1,15-lactone or 8β,12α-$PGA_2$, respectively, there are obtained each of the various corresponding 8β,12α-PGA-type, 1,15-lactones.

EXAMPLE 32

$PGB_2$, 1,15-lactone (Formula CVI: $Z_1$, $Y_1$, $R_5$, $L_1$, and $R_7$ are as defined in Example 1).

Refer to Chart G.

$PGB_2$ (0.334 g.), 5 ml. of dry, oxygen-free xylene, 0.393 g. of triphenylphosphine, and 0.33 g. of 2,2'-dipyridyl sulfide are stirred at room temperature under a nitrogen atmosphere for 6 hrs. The resulting mixture is then diluted with 250 ml. of dry, oxygen-free xylene, and the solution heated at reflux for 16 hr. The resulting mixture is then concentrated under reduced pressure at a bath temperature of 40° C. to remove the xylene. The residue is then chromatographed on a dry pack column of 100 g. of silica gel and 20 ml. of diethyl ether. The column is then eluted with 60 percent diethyl ether and hexane. Thereupon 200 mg. of $PGB_2$, 1,15-lactone are obtained. Silica gel $R_f$ is 0.37 in diethyl ether and hexane (1:1). The mass spectrum shows parent peak 316.2021 and other peaks at 298, 288, 269, and 217. Characteristic NMR absorptions are observed at 5.97-6.80, 5.07-5.70, and 2.83-3.12 δ. UV absorption is observed at 277 mμ ($\epsilon$ = 16,800).

Following the procedure of Example 32, but employing each of the various PGB-type compounds described by formula XLI in place of $PGB_2$, there are obtained each of the various corresponding PGB-type, 1,15-lactones.

EXAMPLE 33

$PGD_2$, 1,15-lactone.

Refer to Chart C.

A. Method employing $PGF_{2\alpha}$, 1,15-lactone as starting material:

1. To a stirred solution at 0° C. of 1.0 g. of $PGF_{2\alpha}$, 1,15-lactone and 3 ml. of anhydrous dimethylformamide is added at 0° C. a solution of 474 mg. of t-butyldimethylsilyl chloride and 428 mg. of imidazole in 3 ml. of dimethylformamide. The resulting mixture is then stirred for 1 hr. at 0° C. under nitrogen, then poured into brine, and extracted with hexane. The combined organic layer is then washed successively with water, cold aqueous sodium bisulfate, water, aqueous sodium bicarbonate, and brine. The organic layer is then dried over sodium sulfate and concentrated under reduced pressure. The crude product is then chromatographed on 140 g. of neutral silica gel. The column is packed with 5 percent ethyl acetate and hexane and diluted with 20 percent ethyl acetate and hexane. Thereupon, 1.10 g. of $PGF_{2\alpha}$,1,15-lactone, 11-(t-butyldimethylsilyl ether) are obtained. Infrared absorptions are observed at 3500, 1730, 1460, 1240, 1125, 1110, 1040, 1005, 975, 880, 840, and 780 cm.$^{-1}$. NMR absorptions are observed at 5.90–4.95, 4.25–3.75, 3.70, and 0.85 δ.

2. A solution of 1.05 g. of the reaction product of part (1) above, 5 ml. of freshly distilled dihydropyran, and 50 mg. of pyridine hydrochloride in 25 ml. of anhydrous methlene chloride are stirred under a nitrogen atmosphere at 25° C. for 18 hrs. The reaction mixture is then poured into a mixture of ice, sodium bicarbonate, and water, and extracted thoroughly with hexane. The organic extracts are then washed with brine, dried over sodium sulfate, and concentrated under reduced pressure to yield a crude product (1.4 g.) which is chromatographed on 140 of neutral silica gel. The column is packed with 5 percent ethyl acetate and hexane and diluted with 10 percent ethyl acetate in hexane. Thereupon 1.16 g. of $PGF_{2\alpha}$, 1,15-lactone, 9-(tetrahydropyranyl ether), 11-(t-butyldimethylsilyl ether) are obtained. Infrared absorptions are observed at 1740, 1460, 1350, 1240, 1140, 1120, 1040, 1020, 990, 975, 860, 840, and 780 cm.$^{-1}$. Infrared absorptions are observed at 5.95–5.0, 4.75–4.50, 4.30–3.25, and 0.88 δ.

3. To a solution of 1.17 g. of the reaction product of subpart (2) above in 5 ml. anhydrous tetrahydrofuran at 25° C. is added under a nitrogen atmosphere 22 ml. of a 0.3M solution of tetra-n-butyl ammonium fluoride in tetrahydrofuran. The reaction mixture is then stirred for 30 min. at 25° C., then poured into a mixture of ice, water, sodium bicarbonate, and hexane. The resulting mixture is then extracted thoroughly with hexane and the organic extracts are then washed with brine, dried over sodium sulfate, and evaporated. The crude product (1.1 g.) is used without further purification. A 75 mg. sample of this crude product, however, is chromatographed on 15 g. of neutral silica gel, packed with 10 percent ethyl acetate in hexane and eluted with 10 percent ethyl acetate in hexane. Accordingly, 16 mg. of pure $PGF_{2\alpha}$, 1,15-lactone, 9-(tetrahydropyranyl ether) are obtained. Infrared absorptions are observed 3500, 1730, 1440, 1340, 1240, 1200, 1160, 1140, 1120, 1080, 1040, 1020, 990, 970, 920, 870, 815, and 735 cm.$^{-1}$. NMR absorptions are observed at 6.0–5.0, 5.75–5.0, 4.35–3.30, and 2.35 δ.

4. A solution of 920 mg. of the reaction product of subpart (3) above in 30 ml. of acetone is cooled to between −20° and −30° C. This cooled mixture is then treated dropwise with 0.8 ml. of the Jones reagent. After 75 min. at −20° to −30° C., 0.5 ml. of isopropyl alcohol is added to destroy excess oxidizing reagent. After an additional 10 min. of stirring at −25° C., the mixture is diluted with 400 ml. of water and extracted thoroughly with a mixture of hexane and ethyl acetate (4:1). The combined organic extracts are then washed successively with water, ice cold aqueous sodium bisulfate, water, aqueous sodium bicarbonate, and brine. The organic extract is then dried over sodium sulfate and concentrated under reduced pressure. This crude (900 mg.) is then chromatographed on 140 g. of neutral silica gel, packed with 5 percent ethyl acetate in hexane and eluted with 20 percent ethyl acetate in hexane. Thereupon, 750 mg. of $PGD_2$, 1,15-lactone, 9-(tetrahydropyranyl ether) are obtained. Infrared absorptions are observed at 1745, 1460, 1440, 1370, 1340, 1240, 1200, 1160, 1140, 1120, 1080, 1040, 1020, 995, 980, 920, 870, 815, and 735 cm.$^{-1}$. NMR absorptions are observed at 5.90–5.0 and 4.80–3.40 δ.

5. A mixture of 700 mg. of the reaction product of subpart (4) above, 33 ml. of tetrahydrofuran, 33 ml. of water, and 66 ml. of acetic acid is heated at 40° C. for 3 hrs. The resulting mixture is then cooled to below room temperature, poured into a mixture of brine and water (1:1), and extracted thoroughly with a mixture of ethyl acetate and hexane (1:1). The combined organic extracts are then washed with aqueous sodium bicarbonate and brine, dried over sodium sulfate and evaporated. Crude product is then crystallized from diethyl ether and hexane mixtures yielding 243 mg. of pure title product. Melting point 93°–94° C. Infrared absorptions are observed at 3470, 3020, 1735, 1725, 1245, 1225, 1160, 1145, 1045, 1025, 960, and 917 cm.$^{-1}$. NMR absorptions are observed at 5.95–5.35, 5.4–4.95, 4.65–4.30, and 2.45 δ. The mass spectrum shows parent peak at 406.2574 and other peaks at 391, 388, 373, 335, 316, 290, and 279.

B. Employing $PGF_{2\alpha}$ as starting material:

1. $PGF_{2\alpha}$ is selectively silylated at C-11 and C-15, preparing the formual XLII compound; etherified at C-9, preparing the formula XLV compound; and selectively desilylated at C-11 and C-15 forming a formula XLVI compound; following the procedures described in Example 33, part A, subparts (1), (2), and (3).

2. The reaction product of subpart (1) above is then 1,15-lactonized following the procedure of Example 1, part A, preparing a formula XLVII compound, $PGF_{2\alpha}$, 1,15-lactone, 9-(tetrahydropyranyl ether).

3. The reaction product of subpart (2) above is oxidized to a ketone at C-11 and hydrolyzed at C-9, following the procedure of Example 33, part A, subparts (4) and (5), thereby preparing the title product.

Following the procedure of Example 33, part A, or Example 33, part B, but employing each of the various $PGF_\alpha$-type, 1,15-lactones described following Example 20, or $PGF_\alpha$-type compounds described by formula I, respectively, in place of $PGF_{2\alpha}$, 1,15-lactone or $PGF_{2\alpha}$, respectively, there are obtained each of the various corresponding PGD-type, 1,15-lactones.

EXAMPLE 34

$8\beta,12\alpha$-$PGD_2$, 1,15-lactone (Formula LXXIII: $Z_1$, $Y_1$, $R_5$, $L_1$, and $R_7$ are as defined in Example 1).

Refer to Chart D.

$8\beta,12\alpha$-$PGF_{2\alpha}$, 1,15-lactone (Example 21) is selectively silylated at C-9, following the procedure of Example 12, part A, preparing a formula LXV compound.

B. This formula LXV compound is then oxidized at C-11, following the procedure of Example 12, part B, thereby preparing a formula LXXII PGD-type 9-silyl ether.

C. Following the procedure of Example 12, part C, the reaction product of part B above is hydrolyzed, thereby preparing the title product.

Following the procedure of Example 34, but employing each of the various $8\beta,12\alpha$-$PGF_{\alpha}$-type, 1,15-lactones described following Example 21 in place of $8\beta,12\alpha$-$PGF_{2\alpha}$, 1,15-lactone, there are obtained each of the various corresponding $8\beta,12\alpha$-$PGF_{\alpha}$-type, 1,15-lactones.

EXAMPLE 35

$9\beta$-$PGD_2$, 1,15-lactone (Formula CLVII: $Z_1$, $Y_1$, $R_5$, $L_1$, and $R_7$ are as defined in Example 1).

Refer to Chart L.

A. Following the procedure of Example 12, part A, $PGE_2$, 1,15-lactone silylated at C-11, preparing a formula CLII compound.

B. Following the procedure of Example 13, part B, subpart 4, the reaction product of part A above is reduced at C-9 and chromatographed yielding a $9\beta$hydroxy formula CLIII compound.

Following the procedure of Example 33, part A, subparts (2)–(5), the reaction product of part B above is etherified at C-9, thereby preparing the formula CLIV compound; selectively hydrolyzed at C-11 (silyl removal), preparing a formula CLV compound; oxidized at C-11, preparing a formula CLVI compound; and hydrolyzed at C-9, thereby prepreparing the title product.

Following the procedure of Example 35, but employing each of the various PGE-type, 1,15-lactones described following Example 22, in place of $PGE_2$, 1,15-lactone, there are obtained each of the various corresponding $9\beta$-PGD-type, 1,15-lactones.

EXAMPLE 36

$8\beta,9\beta,12\alpha$-$PGD_2$,1,15-lactones

Refer to Chart L.

Following the procedure of Example 35, but employing $8\beta,12\alpha$-$PGE_2$, 1,15-lactone (Example 23) in place of $PGE_2$, 1,15-lactone, there is obtained the title product.

Following the procedure of Example 36, but employing each of the various $8\beta,12\alpha$-PGE-type, 1,15-lactones described following Example 23 in place of $8\beta,12\alpha$-$PGE_2$, 1,15-lactone, there are obtained each of the various corresponding $8\beta,9\beta,12\alpha$-PGD-type, 1,15-lactones.

EXAMPLE 37

9-Deoxy-9,10-didehydro-$PGD_2$, 1,15-lactone (Formula XCVI: $Z_1$, $Y_1$, $R_5$, $L_1$, and $R_7$ are as defined in Example 1).

Refer to Chart F.

Following the procedure of Example 30, $PGD_2$, 1,15-lactone is dehydrated, yielding the title compound.

Following the procedure of Example 37, but employing each of the various PGD-type, 1,15-lactones described following Example 33, or each of the various 9,10-didehydro-9-deoxy-PGD-type compounds described by formula I, there are prepared each of the various corresponding 9-deoxy-9,10-didehydro-PGD-type, 1,15-lactones.

EXAMPLE 38

9-Deoxy-9,10-didehydro-$8\beta,12\alpha$-$PGD_2$ (Formula XCVIII: $Z_1$, $Y_1$, $R_5$, $L_1$, and $R_7$ are as defined in Example 1).

Refer to Chart F.

Following the procedure of Example 30 $8\beta,12\alpha$-$PGD_2$, 1,15-lactone is dehydrated, preparing the title compound.

Following the procedure of Example 38, but employing each of the various $8\beta,12\alpha$-PGD-type compounds described following Example 34 or 9-deoxy-9,10-didehydro-$8\beta,12\alpha$-PGD-type compounds described by formula XLI, there are prepared each of the various corresponding 9-deoxy-9,10-didehydro-$8\beta,12\alpha$ -PGE-type, 1,15-lactones.

EXAMPLE 39

9-deoxy-$PGD_2$, 1,15-lactone (Formula CVI: $Z_1$, $Y_1$, $R_5$, $L_1$, and $R_7$ are as defined in Example 1).

Refer to Chart O.

A. To a stirred solution of 9-deoxy-9,10-didehydro-$PGD_2$, 1,15-lactone dissolved in methanol at −25° C. under a nitrogen atmosphere, there is added a solution of sodium borohydride in water and methanol. This mixture is then stirred at −20° C. for 20 min. and thereafter a small quantity of acetic acid is added cautiously. The mixture is concentrated and an additional water is added and the pH of the mixture is thereafter adjusted to 3 by addition of citric acid. The resulting mixture is then extracted with dichloromethane and the combined organic extracts are washed with water and brine, dried, and concentrated to yield the corresponding formula CLXXVII 9-deoxy-$PGF_{2\alpha}$, 1,15-lactone.

B. To a solution of the reaction product of part A dissolved in acetone at −20° C., there is added dropwise with stirring over one min. the Jones reagent. This resulting mixture is then stirred at −20° C. for an additional 20 min. and thereafter a small quantity of isopropanol is added. This mixture is then stirred for about 10 min. at −20° C. Thereafter the mixture is diluted with water and extracted with diethyl ether. Combined organic extracts are washed, dried, and concentrated. The resulting residue is then chromatographed on silica gel, yielding pure title product.

Following the procedure of Example 39, but employing each of the various 9-deoxy-9,10-didehydro-PGD-type, 1,15-lactones described by formula CLXXVI in place of 9-deoxy-9,10-didehydro-$PGD_2$, 1,15-lactone there are obtained each of the various corresponding 9-deoxy-PGD-type, 1,15-lactones.

EXAMPLE 40

9-deoxy-$8\beta,12\alpha$-$PGD_2$, 1,15-lactone (Formula CVI: $Z_1$, $Y_1$, $R_5$, $L_1$, $R_7$ are as defined in Example 1).

Refer to Chart G.

Following the procedure of Example 39, 9-deoxy-9,10-didehydro-$8\beta,12\alpha$-$PGD_2$, 1,15-lactone is thereby transformed to the title product.

Following the procedure of Example 40, but employing each of the various 9-deoxy-9,10-didehydro-$8\beta,12\alpha$-PGD-type, 1,15-lactones described following Example 39, there are obtained each of the various corresponding 9-deoxy-8β,12α-$PGD_2$-type, 1,15-lactones.

EXAMPLE 41 cis-4,5-Didehydro-$PGF_{1\alpha}$, 1,9-lactones (Formula XXII: $Z_1$ is cis—$CH_2$—CH=CH—$(CH_2)_2$, $R_8$, $Y_1$, $M_1$, $L_1$, and $R_7$ are as defined in Example 1).

Refer to Chart A.

cis-4,5-Didehydro-$PGF_{1\alpha}$ (130 mg.) is lactonized following the procedure of Example 1, part A, yielding 40 mg. of title product. Melting point is 83°-85° C. NMR absorptions are observed at 7.80-7.42, 5.68-5.08, 4.28-3.52, and 3.33-0.65 δ.

EXAMPLE 42

15-epi-15-Metyl-13,14-dihydro-$PGF_{2\alpha}$, 1,9-lactone or 15-epi-15-methyl-13,14-dihydro-$PGF_{1\alpha}$, 1,9-lactone 15-Methyl-$PGF_{2\alpha}$, 1,9-lactone (Example 43, 1.17 g.), 234 ml. of ethyl acetate, and 0.7 g. of 5 percent palladium-charcoal catalyst are combined and stirred at 0° C. under a hydrogen atmosphere. After about 2 hrs. hydrogen uptake is terminated, and the filtrate is evaporated and azeotrope with benzene to yield 1.189 g. of an oil. This oil is then chromatographed on silica gel, eluting with 75 percent ethyl acetate in hexane. Thereupon, 0.2 g. of 15-epi-15-methyl-13,14-didehydro-$PGF_{2\alpha}$, 1,9-lactone, and 0.58 g. of 15-epi-15-methyl-13,14-dihydro-$PGF_{2\alpha}$, 1,9-lactone are obtained. For 15-epi-15-methyl-13,14-didehydro-$PGF_{1\alpha}$, 1,9-lactone, lactone, the mass spectrum shows a parent peak at 483.3303 and another peak at 488. NMR absorptions are observed at 5.5-5.03, 4.25-3.60, and 3.00-0.60 δ.

EXAMPLE 43

15-Epi-15-Methyl-$PGF_{2\alpha}$, 1,9-lactone (Formula XXII: $Z_1$, $R_8$, $Y_1$, $L_1$, and $R_7$ are as defined in Example 1, and $M_1$ is

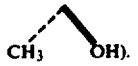

Refer to chart A.

15-Epi-15-Methyl-$PGF_{2\alpha}$ (1.01 g.) 5 ml. of benzene, 1.04 g. of triphenylphosphine, and 0.87 g. of 2,2'-dipyridylsulfide are reacted following the procedure of Example 1, part A. Pure product is recovered from the reaction mixture employing high pressure liquid chromatography, eluting with 100 percent ethyl acetate. Thereby, 1.08 g. of product is obtained which is rechromatographed on 125 g. of silica gel, eluting with diethyl ether. Chromatography is continued until 380 mg. of pure product is obtained. Silica gel $R_f$ is 0.3 in 75 percent ethyl acetate in Skellysolve B. The mass spectrum shows a base peak at 494.3234 and other peaks at 479, 423, 404, 389, 333, 186, and 143. Infrared absorptions are observed at 3420, 2960, 2940, 2860, 1740, 1715, 1450, 1370, 1350, 1225, 1180, 1145, 1125, 1085, 1045, 1030, and 970 $cm.^{-1}$.

Example 44

15-epi-15-methyl-$PGF_{2\beta}$, 1,9-lactone (Formula XXII: $Z_1$,$R_8$,$M_1$, $L_1$, and $R_7$ are as defined in Example 43).

Refer to Chart A.

15-epi-15-Methyl-$PGF_{2\alpha}$ (0.62 g.), 0.67 g. of triphenylphosphine, in 0.65 g. of 2,2'-dipyridylsulfide is lactonized following the procedure of Example 1, part A. A resulting yellow colored solution is then evaporated at 45° C. to yield 2.3 g. of a yellowish-brown oil. This oil is then dissolved in ethyl acetate, washed with 2M sodium bisulfate, saturated sodium bicarbonate, and brine and dried over sodium sulfate to yield 1.8 g. of a light brown oil. This oil is then chromatographed on 200 g. of silica gel packed in 50 percent ethyl acetate and Skellysolve B, eluting with ethyl acetate. Chromatography is repeated employing silica gel packed in 25 percent ethyl acetate in hexane, eluting with 50 percent ethyl acetate in hexane, yielding 130 mg. of title product. Silica gel $R_f$ is 0.42 in 75 percent ethyl acetate in Skellysolve B. The mass spectrum shows parent peak at 494.3249. (TMS serivative)

EXAMPLE 45

15-Methyl-$PGF_{2\alpha}$, 1,9-lactone (Formula XXII: $Z_1$, $R_8$, $Y_1$, $L_1$, and $R_7$ are as defined in Example 43 and $M_1$ is

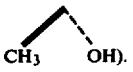

Refer to Chart A.

A solution of 15-methyl-$PGF_{2\alpha}$ (185 mg.) in 2.5 ml. of an anhydrous, oxygen-free xylene containing 2,2'-dipyridyl disulfide (165 mg.) and triphenylphosphine (196 mg.) is stirred under nitrogen for 2.5 hr. at 25° C. The mixture is diluted with 150 ml. of xylene and heated at reflux for 3 hr. TLC (80 percent EtOAc/hexane) shows essentially a single, less polar product. The xylene is removed by evaporation at reduced pressure to afford a residue which is diluted with ice/water/sodium bicarbonate and ethyl acetate and extracted thoroughly with ethyl acetate. The ethyl acetate extract is washed with brine, dired over anhydrous sodium sulfate and concentrated to afford a residue of (15S)-15-methyl $PGF_{2\alpha}$, 1,9-lactone. The residue is purified by chromatography on 50 g. of neutral silica packed with 10 percent acetone/methylene chloride and eluted (5 ml. fractions) with 200 ml. of 10percent acetone/methylene chloride, 1500 ml. of 20 percent acetone/methylene chloride and 1000 ml. of 35 percent acetone/methylene chloride.

Those fractions containing homogeneous product by TLC assay (fractions 135-229) are combined to yield pure 15-methyl-$PGF_{2\alpha}$, 1,9-lactone.

The product exhibits infrared peaks at 3400, 3000, 2960, 2920, 2860, 1740, 1715, 1450, 1370, 1350, 1265, 1225, 1205, 1180, 1145, 1125, 1085, 1030, 970, 935, 905, and 715 $cm^{-1}$ and the mass spectrum shows peaks at m/e 350 (M+), 332 (M-18), 314, 303, 288, 261, 243.

EXAMPLE 46

15-Methyl-17-phenyl-18,19,20-trinor-$PGF_{2\alpha}$, 1,9-lactone (Formula XXII: $Z_1$, $R_8$, $Y_1$, $M_1$, and $L_1$ are as defined in Example 45 and $R_7$ is

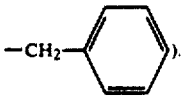

Refer to Chart A.

A solution of 15-methyl-17-phenyl-18,19,20-trinor-$PGF_{2\alpha}$(474 mg.) in 10 ml. of of benzene is treated with triphenylphosphine (464 mg.) and 2,2'-dipyridyl disulfide (390 mg.). The resulting yellow solution is stirred for 2 hrs. at 25° C. under nitrogen, then diluted with 250 of anhydrous, oxygen-free benzene and heated at reflux for 24 hrs. The benzene is removed in vacuo to afford a residue which is chromatographed on 60 g. of neutral silica packed with 10 percent acetone/methylene chloride and eluted with 300 ml. of 10 percent acetone/-methylene chloride followed by 1000 ml. of 20 percent acetone/methylene chloride (fraction size approx. 7 ml.).

Those fractions containing homogeneous product by TLC analysis (fractions 80–95) are combined, affording pure 15-methyl-17-phenyl-18,19,20-trinor-$PGF_{2\alpha}$, 1,9-lactone with infrared peaks at 3400, 3060, 2960, 2940, 2860, 1735, 1710, 1605, 1495, 1450, 1365, 1345, 1265, 1225, 1180, 1145, 1115, 1085, 1030, 975, 750, 720 and 700 $cm.^{-1}$ and NMR peaks at 7.27 (pehnyl; singlet; 5H), 5.8–5.1 (vinyl and C-9H; multiplet; 5H), 4.30–3.75 (C<u>H</u>OH; multiplet; 1H) and 1.40 ppm (15-<u>$CH_3$</u>; singlet; 3H) and mass spectrum peaks at M+ 528.3112 (calc'd. for $C_{30}H_{48}Si_2O_4$: 528.3091); as well as m/e 513, 438, 423, 333, 91.

EXAMPLE 47

2,2-Difluoro-15-methyl-$PGF_{2\alpha}$, 1,9-lactone (Formula XXII: $Z_1$ is cis—CH=CH—$(CH_2)_2$—$CF_2$—, $R_8$, $Y_1$, $M_1$, $L_1$, and $R_7$ are as defined in Example 45).

Refer to Chart A.

A solution of 2,2-difluoro-P15-methyl-$PGF_{2\alpha}$ methyl ester (150 mg.) in 5 ml. of methanol at 0° is treated with 4 ml. of 3N aqueous potassium hydroxide and stirred under nitrogen at 0° for 30 min. The reaction mixture is acidified with cold aqueous potassium bisulfate and extracted thoroughly with ethyl acetate. The extract is washed with brine, dried over sodium sulfate and concentrated to afford a residue of 2,2-difluoro-15-methyl-$PGF_{2\alpha}$.

The residue is immediately dissolved in 10 ml. of anhydrous, oxygen-free benzene, treated with triphenylphospine (141 mg.) and 2,2'-dipyridyl disulfide (118 mg.), and stirred at room temperature for 20 min. when TLC (AIX) analysis indicates that, in addition to the pyridinethiol ester formation, lactonization had already occurred as well. The solvent is removed under vacuum to yield a residue containing 2,2-difluoro-15-methyl-$PGF_{2\alpha}$, 1,9-lactone.

The residue is purified by chromatography on 60 g. of neutral silica packed with 30 percent aceton/methylene chloride and eluted with 40 percent acetone/methylene chloride (approx. 6 ml. fractions).

Those fractions which are homogeneous by TLC analysis (fractions 49-56) are combined to afford pure (15S) 2,2-difluoro-15-methyl-$PGF_{2\alpha}$, 1,9-lactone with NMR preaks at 5.90–5.10 (vinyl and C-9H; multiplet, 5H), 4.10–3.65 (C<u>H</u>OH; multiplet; 1H) and 1.26 ppm ($CH_3$; signlet; 3H).

The means spectrum establishes molecular weight as m/e 530.3078 for the trimethylsily ether (calc'd. for $C_{27}H_{48}Si_2ORF_2$: 530.3059).

EXAMPLE 48 cis-4,5-Didehydro-$PGF_{1\alpha}$, 1,15-lactone (the 8β,12α-siomer of Formula LXIV: $Z_1$ is cis—$CH_2$—CH=CH—$(CH_2)_2$—, $R_8$, $Y_1$, $R_5$, $L_1$, and $R_7$ are as defined in Example 1).

Refer to Chart A.

A. cis-4,5-Didehydro-$PGF_{1\alpha}$ (200 mg. of n-butylboronic acid in 10 ml. of dichloromethane are reacted according to the procedure of Example 20, part A yielding 340 mg. of an oil.

B. The oil is then dissolved in 6.5 ml. of oxygen-free xylene and 190 mg. of 2,2'-dipyridyl sulfide followed by addition of 223 mg. of triphenylphosphine. Thereafter, the reaction proceeds as is described in Example 20, parts B and C. Chromatography yields 80 mg. of pure product. Silica gel $R_f$is 0.35 and ethyl acetate. The mass spectrum shows base peak at 480.3069 and other peaks at 480, 465, 390, 364, 300, and 217. NMR absorptions are observed at 6.25–4.83, 4.30–3.80, and 2.90–0.65 δ.

EXAMPLE 49

13,14-Didehydro-$PGF_{1\alpha}$, 1,15-lactone (the 8β,12α-isomer of Formula LXIV: $Z_1$ is —$(CH_2)_5$—, $Y_1$ is —C≡C—, $R_8$, $M_1$, $L_1$, and $R_7$ are as defined in Example 1).

Refer to Chart D.

Following the procedure of Example 48, 880 mg. of 13,14-Didehydro-$PGF_{1\alpha}$ is transformed to 80 mg. of the title product. Melting point is 75°–76° C. Infrared absorptions are observed at 3500, 2950, 2250, 1740, 1455, 1370, 1235, 1040, 735 $cm.^{-1}$. NMR absorptions are observed at 5.58–5.20, 4.40–3.90, 3.53–0.60 δ.

EXAMPLE 51

13,14-Didehydro-$PGF_{2\alpha}$, 1,15-lactone (the 8α,12β-isomer of Formula LXIV: $Y_1$ is —C≡C—, $Z_1$, $R_5$, $L_1$, and $R_7$ are as defined in Example 1).

Refer to Chart D.

Following the procedure of Example 48, but employing 240 mg. of 13,14-didehydro-$PGF_{2\alpha}$, there is obtained 80 mg. of title product. $R_f$is 0.4 in diethyl ether. Infrared absorptions are observed at 3300, 2940, 1735, 1330, 1240, 1140, 1115, 1100, and 1040 $cm.^{-1}$. NMR absorptions are observed at 5.75–5.22, 4.38–4.03, and 2.93–0.72 δ.

EXAMPLE 51

17-Phenyl-18,19,20-trinor-$PGF_{2\alpha}$, 1,15-lactone (the 8α,12β-isomer of Formula LXIV: $Z_1$, $Y_1$, $R_5$, and $L_1$ are as defined in Example 1, and $R_7$ is

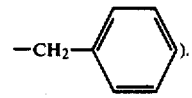

Refer to Chart D.

A. A solution of 17-phenyl-18,19,20-trinor-$PGF_{2\alpha}$, 776 mg.) and 1-butaneboronic acid (225 mg.) in 25 ml. of methylene chloride is heated at reflux. After 15 min. the methylene chloride is allowed to distill off slowly. Fresh methylene chloride is added when the total volume is reduced to about one-half of the original volume. After 90 minutes, all of the methylene chloride is removed in vacuo to afford cyclic boronate of the starting prostaglandin.

B. The cyclic boronate is dissolved in 5 ml. of anhydrous, oxygen-free xylene and is treated with 2,2'-dipyridyl disulfide (660 mg.) and triphenylphosphine (786 mg.). After 4 hours at 25° the reaction mixture is diluted with 500 ml. of anhydrous, oxygen-free xylene and is heated at reflux for 18 hr. The xylene is removed in vacuo to give a residue. The residue is taken up in 50 ml. of tetrahydrofuran containing 1 ml. of 30 percent aqueous hydrogen peroxide (11.6 mmoles) and treated at 25° C. with a solution of sodium bicarbonate (1.68 g.) in 10 ml. of water. This mixture is stirred vigorously for 30 min., then concentrated under reduced pressure to give a residue. The residue is taken up in brine/ethyl acetate and extracted thoroughly with ethyl acetate. The combined extracts are washed with aqueous sodium bisulfate, water, aqueous sodium bicarbonate and brine, then dried over sodium sulfate and concentrated to afford a residue of crude 17-phenyl-18,19,20-trinor-$PGF_{2\alpha}$, 1,15-lactone.

The crude lactone is purified by chromatography on 400 g. of neutral silica packed and eluted (22 ml. fractions) with ethyl acetate. The fractions which contained the product, based on TLC, are yielding purified 17-phenyl-18,19,20-trinor-$PGF_{2\alpha}$, 1,15-lactone. The lactone crystallized upon trituration and after two recrystallizations from ethyl acetate/hexane exhibits m.p. 116°-117° C.

The infrared spectrum exhibits peaks at 3460, 3400 sh, 3020, 1705, 1650, 1605, 1495, 1325, 1300, 1265, 1150, 1100, 1040, 1020, 1000, 970, and 700 cm.$^{-1}$ and the mass spectrum shows fragments at m/e 370 (M-18), 352, 334, 308, 298, 261, 243, 225. (No M+ peak is apparent).

EXAMPLE 52

17-Phenyl-18,19,20-trinor-$PGE_2$, 1,15-lactone (Formula LXXXII: $Z_1$, $R_8$, $Y_1$, $R_5$, and $L_1$ are as defined in Example 1, and $R_7$ is

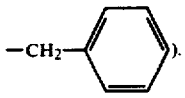

Refer to Chart E.

A solution of 17-phenyl-18,19,20-trinor-$PGE_2$ (735 mg.), 2,2'-dipyridyldisulfide (628 mg.) and triphenylphosphine (748 mg.) in 10 ml. of anhydrous, oxygen-free xylene is stirred at 25° C. in an atmosphere of nitrogen for 2 hr. The mixture is then diluted with 400 ml. of anhydrous, oxygen-free xylene, heated at reflux for 2.5 hrs., and evaporated under vacuum at 30° C. to give a residue. The residue is chromatographed on 100 g. of neutral silica, packed and eluted (8 ml. fractions) with 80 percent ether/hexane. The fractions containing homogeneous product by TLC are combined to afford purified 17-phenyl-18,19,20-trinor-$PGE_2$, 1,15-lactone. Two recrystallizations from ether/hexane afford pure product, m.p. 81°-83° C. The infrared spectrum exhibits peaks at 3440, 3000, 1725, 1605, 1500, 1330, 1240, 1160, 1145, 1085, 1045, 975, 745, 725 and 700 cm.$^{-1}$ and the mass spectrum shows fragments at m/e 368 (M-18), 350, 332, 297, 296, 277, 264, 259, 241 (no M+ apparent).

EXAMPLE 53

16-Phenoxy-17,18,19,20-tetranor-$PGF_{2\alpha}$, 1,5-lactone (Formula XXII: $Z_1$, $R_8$, $Y_1$, $R_5$, and $L_1$ are as defined in Example 1 and $R_7$ is

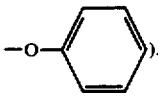

Refer to Chart A.

Following the procedure of Example 1, part A, but substituting 16-phenoxy-17,18,19,20-tetranor-$PGF_{2\alpha}$ for $PGF_{2\alpha}$ there is produced a crude product of 16-phenoxy-17,18,19,20-tetranor-$PGF_{2\alpha}$, 1,15-lactone as a viscous yellow oil.

The crude product is purified by chromatography over neutral silica packed in 50 percent ethyl acetate/-hexane and eluted with 50 percent ethyl acetate/hexane followed by 70 percent ethyl acetate hexane. Those fractions containing homogeneous product as determined by TLC are combined to afford crystalline 16-phenoxy-17,18,19,20-tetranor-$PGF_{2\alpha}$, 1,15-lactone. The lactone thus obtained is recrystallized from ethyl acetate/hexane to afford pure product, m.p. 185°-186° C. The mass spectrum of the trimethylsilyl derivative exhibits a peak at M+ 516.2738 (theory for $C_{28}H_{44}Si_2O_5$: 516.2727) and fragments at m/e 501, 426, 423, 409, 400, 333, 307, 217 and 181.

EXAMPLE 54

$PGF_{1\alpha}$, 1,15-lactone or 15-epi-$PGF_{1\alpha}$, 1,15-lactone (Formula XXII: $Z_1$ is —$(CH_2)_5$—, $R_5$, $Y_1$, $M_1$, $L_1$, and $R_7$ are as defined in Example 1).

Refer to Chart A.

Following the procedure of Example 1, part A, but substituting $PGF_{1\alpha}$ for $PGF_{2\alpha}$ there is obtained a crude product containing $PGF_{1\alpha}$, 1,15-lactone as a viscous yellow oil.

The crude product is purified by chromatography on 700 g. of neutral silica, packed and eluted with 50 percent ethyl acetate/hexane. The first 2 liters of eluate are discarded, after which 100 ml. fractions are collected.

A minor product eluted first from the column (fractions 14-19) which is homogeneous by TLC was combined to give 15-epi-$PGF_{1\alpha}$, 1,15-lactone [(15R)-$PGF_{2\alpha}$, 1,15-lactone]. The infrared spectrum exhibits peaks at 3450, 1730, 1585, 1250, 1100, 970 and 735 cm.$^{-1}$ and the NMR spectrum shows peaks ($\delta_{TMS}^{CDCl_3}$) at 5.85-5.05 (vinyl and C-15; multiplet; 3H; 4.25-3.85 (C<u>H</u>OH; multiplet; 2H) and 3.30 ppm (singlet, shifts downfield when sample is cooled; O<u>H</u>; 2H).

The major product, eluted later from the column (fractions 21-28), was combined to afford purified $PGF_{1\alpha}$, 1,15-lactone. The purified $PGF_{1\alpha}$, 1,15-lactone cyrstallizes upon trituration with ether, and recrystallization (ethyl acetate/hexane) affords a pure sample, m.p. 105°-106° C. The infrared spectrum exhibits peaks at umax 3520, 3480, 3380, 1710, 1300, 1290, 1265, 1250, 1235, 1160, 1110, 1075, 1055, 1000, and 965 cm.$^{-1}$. The NMR spectrum shows peaks at 6.0-5.75 (vinyl; multiplet; 2H;, 5.60-5.00 (C-15H; multiplet; 1H), 4.25-3.80 (C<u>H</u>OH; multiplet; 2H) and 3.08 ppm (O<u>H</u>; singlet, shifts downfield on cooling; 2H), and the mass spectrum shows fragments at 338 (M+), 320, 302, 266, 249, 231.

EXAMPLE 55

$PGE_1$, 1,15-lactone (Formula L: $Z_1$ is $-(CH_2)_5-$, $R_8$, $Y_1$, $R_5$, $L_1$, and $R_7$ are as defined in Example 1).

Refer to Chart C.

Following the procedure of Example 22, but substituting $PGF_{1\alpha}$, 1,15-lactone for $PGF_{2\alpha}$, 1,15-lactone, there is produced a crude product containing $PGE_1$, 1,15-lactone. Chromatography of the crude $PGE_1$, 1,15-lactone over neutral silica packed in 20 percent ethyl acetate/hexane affords pure $PGE_1$, 1,15-lactone, m.p. 87°–88° C.

The infrared spectrum exhibits peaks at 3390, 3320 sh, 1745, 1720, 1335, 1255, 1235, 1195, 1180, 1160, 1100, 1075, and 980 cm.$^{-1}$; the NMR spectrum exhibits peaks ($\delta_{TMS}^{CDCl_3}$) at 6.1–5.85 (vinyl; multiplet; 2H), 5.45–5.05 (C-15H; multiplet; 1H), and 4.40–3.85 ppm (C-11H; multiplet; 1H); and the mass spectrum of the trimethylsilyl ether showed M+ 408.2694 : (theory for $C_{23}H_{40}SiO_4$ = 408.2606) as well as peaks at m/e 393, 390, 380, 375, 365, 364, 318, 264, 150, and 99.

EXAMPLE 64

15-Methyl-$PGF_{2\alpha}$, 1,15-lactone (Formula XLIV: $Z_1$, $Y_1$, $L_1$, and $R_7$ are as defined in Example 1, and $R_5$ is methyl).

Refer to Chart B.

15-Methyl-$PGF_{2\alpha}$(1.97 g.) is transformed by the procedure of Example 20, part A, to a corresponding cycloboronate.

B. The reaction product of part A is then reacted with 40 ml. of xylene, 2.10 g. of tripehnylphosphine, and 1.67 g. of 2,2'-dipyridyl disulfide, with stirring for 4 hr. at room temperature, thereby preparing the pyridine thiol ester of the reaction product of part A.

C. The reaction product of part B (about 40 ml.) is then divided into two equal volume aliquots which are separately lactonized as follows:

About one-half of the reaction product of part B (20 ml.) is then combined with 1 l. of oxygen-free xylene and heated at reflux for 7 hr. The resulting mixture is then cooled to room temperature and the xylene evaporated under reduced pressure.

D. The reaction product of part C is then treated with 100 ml. of tetrahydrofuran, 2 ml. of hydrogen peroxide, and 20 ml. of saturated sodium bicarbonate. This mixture is then vigorously stirred at room temperature for 30 min., diluted with 50 ml. of water, and dried under reduced pressure. The residue is then diluted with brine, extracted with ethyl acetate, and the organic layer washed with brine, dried over magnesium sulfate, and evaporated under reduced pressure, yielding a 3.2 g. residue. This residue is then chromatographed on 150 g. of silica gel, packed with 50 percent ethyl acetate in hexane, eluting with 50 to 100 percent ethyl acetate in hexane and thereafter with 20 percent methanol in ethyl acetate. Fractions containing pure title product are combined, yielding 8.5 mg. The mass spectrum of the bis TMS derivative shows parent peak at 494.3234 and other peaks at 479, 450, 423, 404, 378, 367, 314, 351, and 217.

Following the procedure of the above examples there are obtained each of the various PG-type lactones described in the following Tables from each of the respective corresponding free acids.

In interpreting these Tables, each formula listed in the Table represents a prostaglandin-type lactone whose complete name is given by combining the name provided in the respective legends below the formula with the prefix found in the "Name" column in the tabular section of the Tables for each example.

Table A

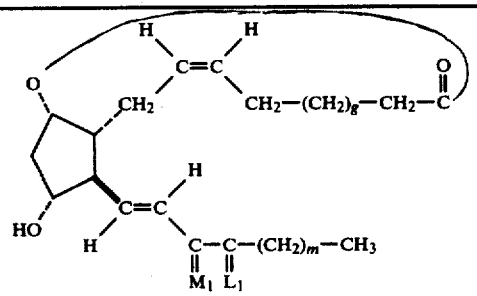

$PGF_{2\alpha}$-type, 1,9-lactones

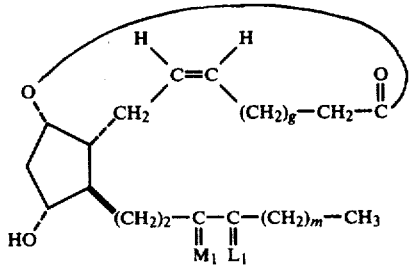

13,14-dihydro-$PGF_{2\alpha}$-type, 1,9-lactones

Table A-continued
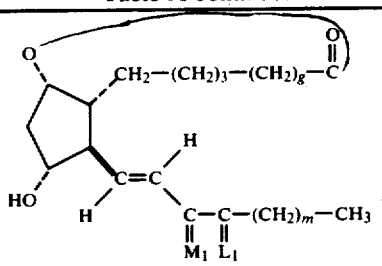
PGF$_{1\alpha}$-type, 1,9-lactones
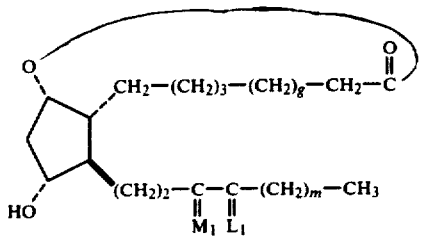
13,14-dihydro-PGF$_{1\alpha}$-type, 1,9-lactones
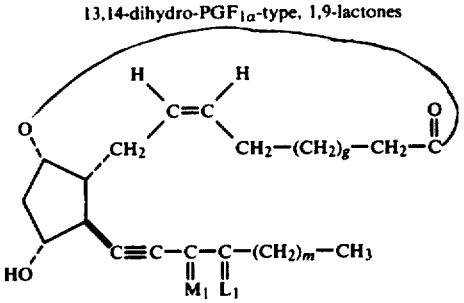
13,14-didehydro-PGF$_{2\alpha}$-type, 1,9-lactones
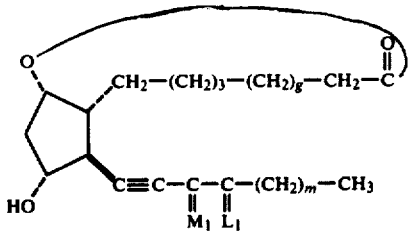
13,14-didehydro-PGF$_{1\alpha}$-type, 1,9-lactones
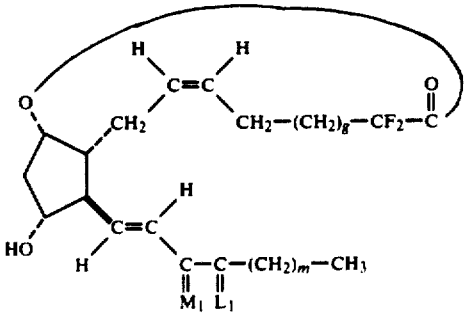
2,2-difluoro-PGF$_{2\alpha}$-type, 1,9-lactones Table A-continued
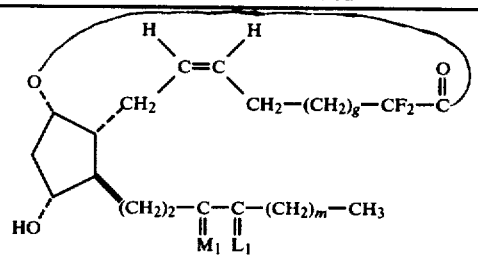
2,2-difluoro-13,14-dihydro-PGF$_{2\alpha}$-type, 1,9-lactones
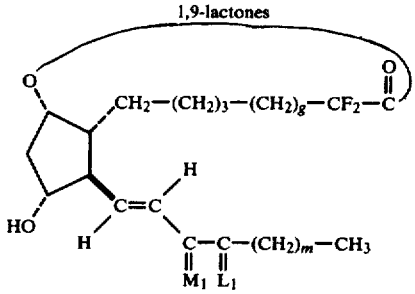
2,2-difluoro-PGF$_{1\alpha}$-type, 1,9-lactones
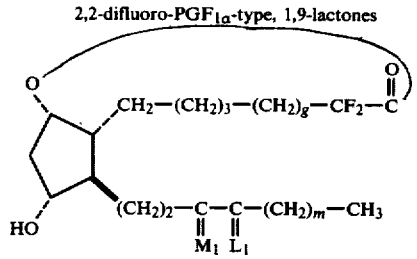
2,2-difluoro-13,14-dihydro-PGF$_{1\alpha}$-type, 1,9-lactones
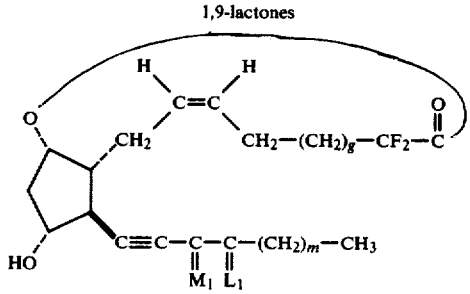
13,14-didehydro-2,2-difluoro-PGF$_{2\alpha}$-type, 1,9-lactones
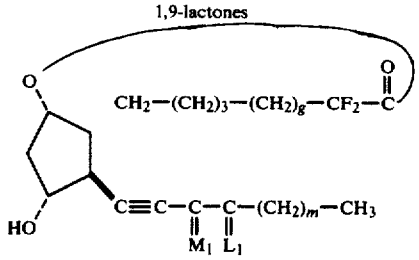
13,14-didehydro-2,2-difluoro-PGF$_{1\alpha}$-type, 1,9-lactones Table A-continued
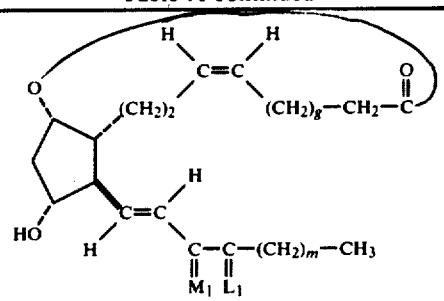
cis-4,5-didehydro-PGF$_{1\alpha}$-type, 1,9-lactones
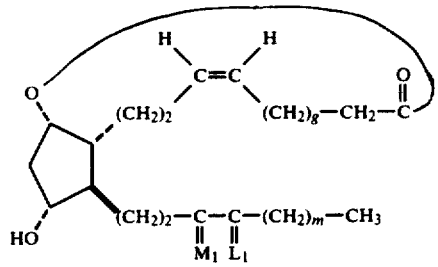
cis-4,5-didehydro-13,14-dihydro-PGF$_{1\alpha}$-type, 1,9-lactones
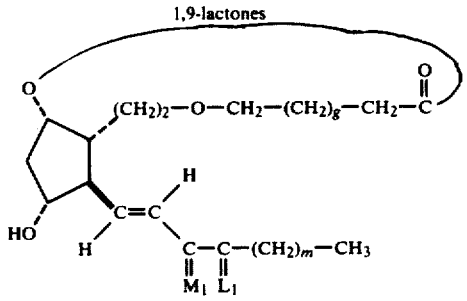
5-oxa-PGF$_{1\alpha}$-type, 1,9-lactones
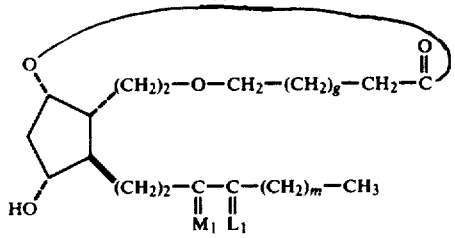
5-oxa-13,14-dihydro-PGF$_{1\alpha}$-type, 1,9-lactones
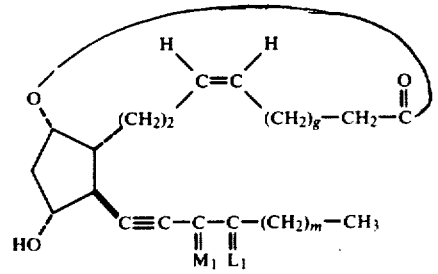
13,14-didehydro-cis-4,5-didehydro-PGF$_{1\alpha}$-type, 1,9-lactones Table A-continued
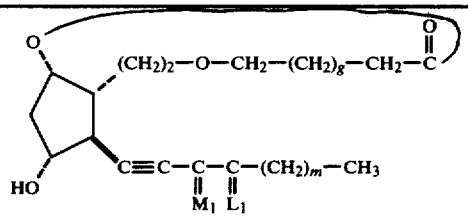
13,14-didehydro-5-oxa-PGF$_{1\alpha}$-type, 1,9-lactones
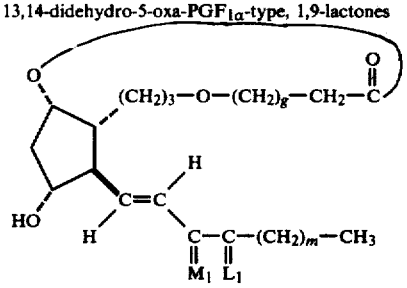
4-oxa-PGF$_{1\alpha}$-type, 1,9-lactones
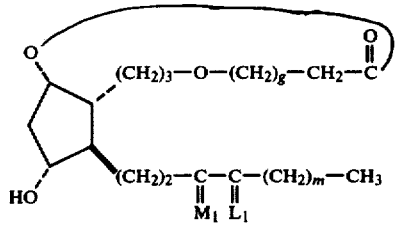
4-oxa-13,14-dihydro-PGF$_{1\alpha}$-type, 1,9-lactones
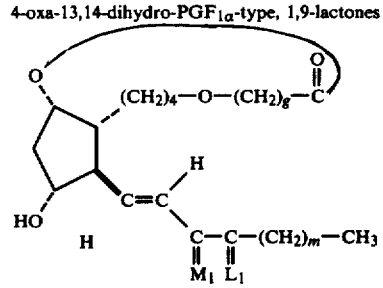
3-oxa-PGF$_{1\alpha}$-type, 1,9-lactones
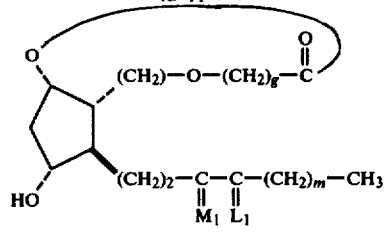
3-oxa-13,14-dihydro-PGF$_{1\alpha}$-type, 1,9-lactones
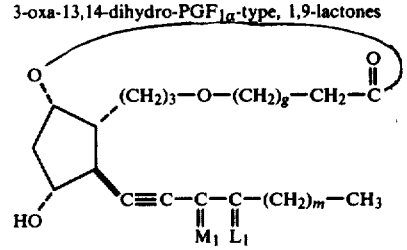
13,14-didehydro-4-oxa-PGF$_{1\alpha}$-type, 1,9-lactones Table A-continued
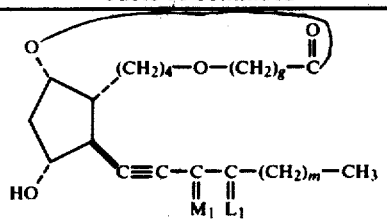
13,14-didehydro-3-oxa-PGF$_{1\alpha}$-type, 1,9-lactones
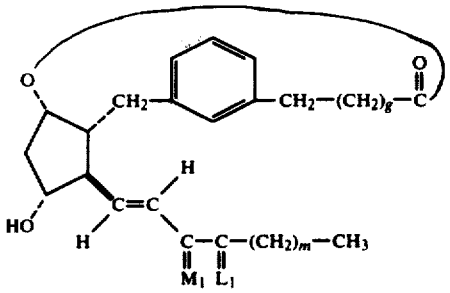
3,7-inter-m-phenylene-4,5,6-trinor-PGF$_{1\alpha}$-type, 1,9-lactones
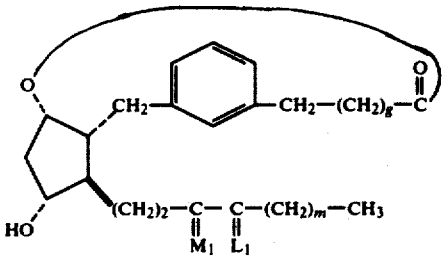
3,7-inter-m-phenylene-4,5,6-trinor-13,14-dihydro-PGF$_{1\alpha}$-type, 1,9-lactones
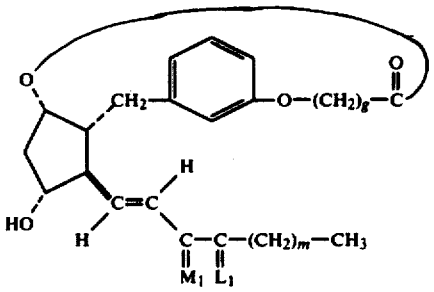
3,7-inter-m-phenylene-3-oxa-4,5,6-trinor-PGF$_{1\alpha}$-type, 1,9-lactones
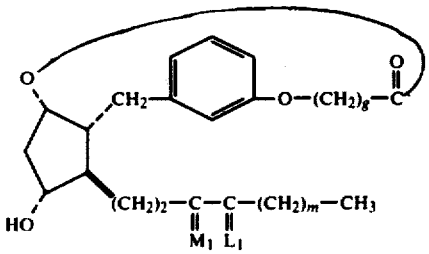
3,7-inter-m-phenylene-3-oxa-4,5,6-trinor-13,14-dihydro-PGF$_{1\alpha}$-type, 1,9-lactones Table A-continued

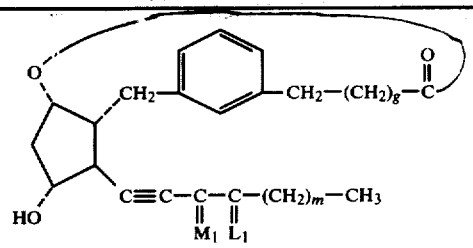

13,14-didehydro-3,7-inter-m-phenylene-4,5,6-trinor-$PGF_{1\alpha}$-type, 1,9-lactones

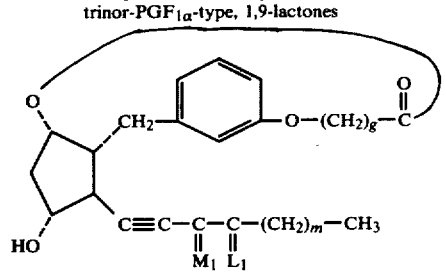

13,14-didehydro-3,7-inter-m-phenylene-3-oxa-4,5,6-trinor-$PGF_{1\alpha}$-type, 1,9-lactones

| | | | $L_1$ | | $M_1$ | | |
|---|---|---|---|---|---|---|---|
| Example | g | m | $R_3$ | $R_4$ | $R_5$ | ~OH | Name |
| A-1 | 1 | 3 | methyl | hydrogen | hydrogen | α | 16-methyl |
| A-2 | 1 | 3 | methyl | hydrogen | methyl | α | 15,16-dimethyl |
| A-3 | 1 | 3 | methyl | hydrogen | hydrogen | β | 15-epi-16-methyl |
| A-4 | 1 | 3 | methyl | methyl | hydrogen | α | 16,16-dimethyl |
| A-5 | 1 | 3 | methyl | methyl | methyl | α | 15,16,16-trimethyl |
| A-6 | 1 | 3 | methyl | methyl | hydrogen | β | 15-epi-16,16-dimethyl |
| A-7 | 1 | 3 | fluoro | hydrogen | hydrogen | α | 16-fluoro |
| A-8 | 1 | 3 | fluoro | hydrogen | methyl | α | 15-methyl-16-fluoro |
| A-9 | 1 | 3 | fluoro | hydrogen | hydrogen | β | 15-epi-16-fluoro |
| A-10 | 1 | 3 | fluoro | fluoro | hydrogen | α | 16,16-dufluoro |
| A-11 | 1 | 3 | fluoro | fluoro | methyl | α | 15-methyl-16,16-difluoro |
| A-12 | 1 | 3 | fluoro | fluoro | hydrogen | β | 15-epi-16,16-difluoro |
| A-13 | 1 | 3 | hydrogen | hydrogen | hydrogen | α | (title compound) |
| A-14 | 1 | 3 | hydrogen | hydrogen | hydrogen | β | 15-epi |
| A-15 | 3 | 3 | hydrogen | hydrogen | hydrogen | α | 2a,2b-dihomo |
| A-16 | 3 | 3 | methyl | methyl | hydrogen | α | 2a,2b-dihomo-16,16-dimethyl |
| A-17 | 3 | 3 | methyl | methyl | methyl | α | 2a,2b-dihomo-15,16,16-trimethyl |
| A-18 | 3 | 3 | fluoro | fluoro | hydrogen | α | 2a,2b-dihomo-16,16-difluoro |
| A-19 | 3 | 3 | fluoro | fluoro | methyl | α | 2a,2b-dihomo-15-methyl-16,16-difluoro |

Table B

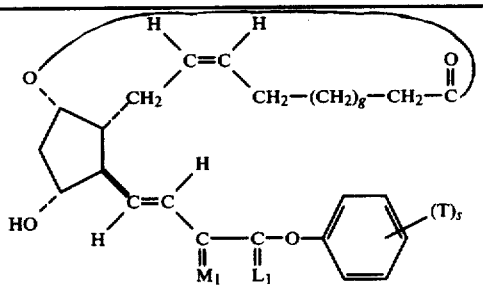

$PGF_{2\alpha}$-type, 1,9-lactones

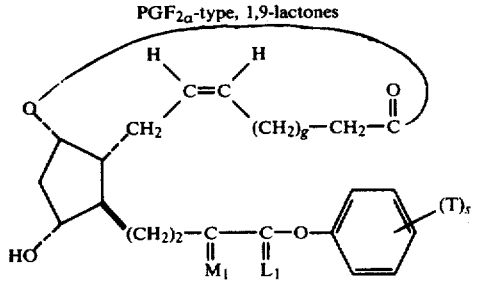

Table B-continued
13,14-dihydro-$PGF_{2\alpha}$-type, 1,9-lactones
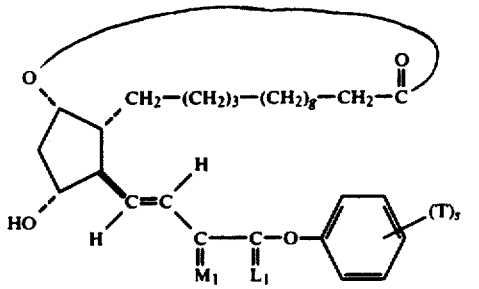
$PGF_{1\alpha}$-type, 1,9-lactones
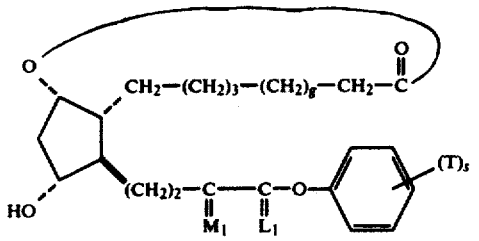
13,14-dihydro-$PGF_{1\alpha}$-type, 1,9-lactones
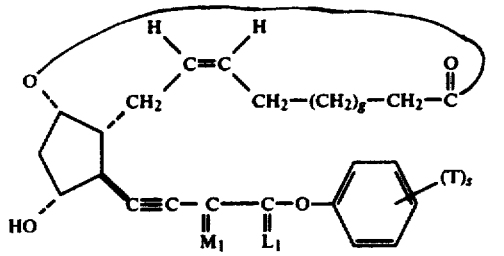
13,14-didehydro-$PGF_{2\alpha}$-type, 1,9-lactones
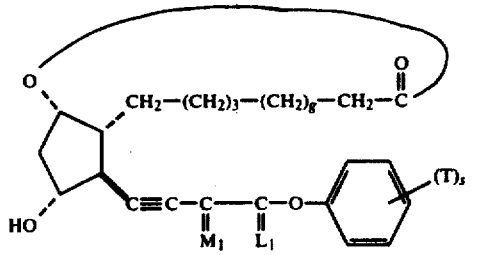
13,14-didehydro-$PGF_{1\alpha}$-type, 1,9-lactones
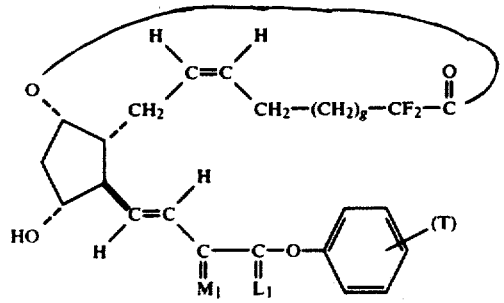
2,2-difluoro-$PGF_{2\alpha}$-type, 1,9-lactones Table B-continued
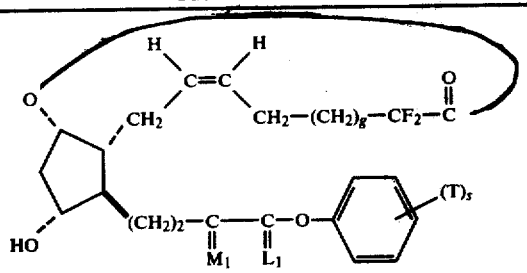
2,2-difluoro-13,14-dihydro-PGF$_{2\alpha}$-type, 1,9-lactones
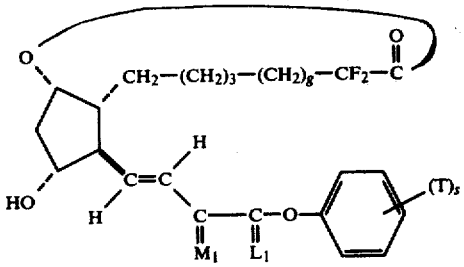
2,2-difluoro-PGF$_{1\alpha}$-type, 1,15-lactones
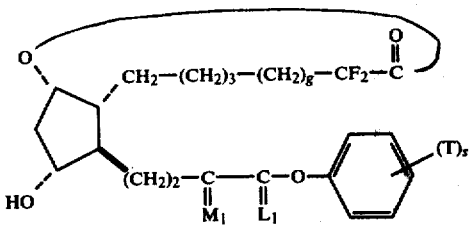
2,2-difluoro-13,14-dihydro-PGF$_{1\alpha}$-type, 1,9-lactones
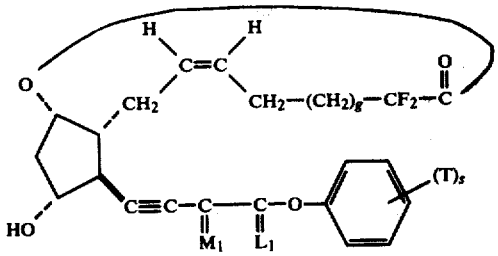
13,14-didehydro-2,2-difluoro-PGF$_{2\alpha}$-type, 1,9-lactones
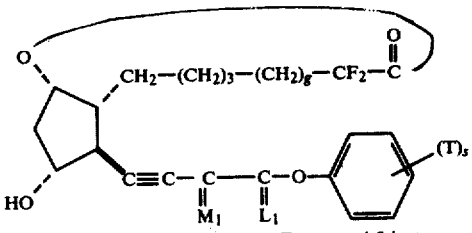
13,14-didehydro-2,2-difluoro-PGF$_{1\alpha}$-type, 1,9-lactones
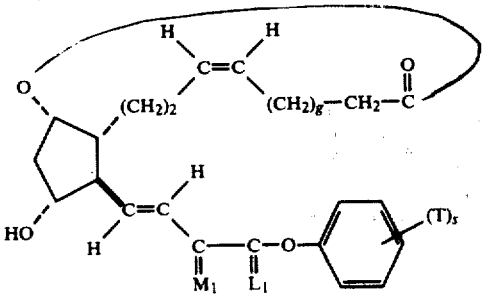
cis-4,5-didehydro-PGF$_{1\alpha}$-type, 1,9-lactones Table B-continued
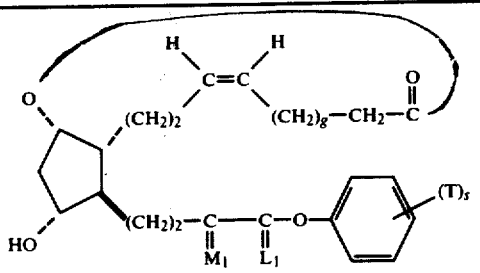
cis-4,5-didehydro-13,14-dihydro-PGF$_{1\alpha}$-type, 1,9-lactones
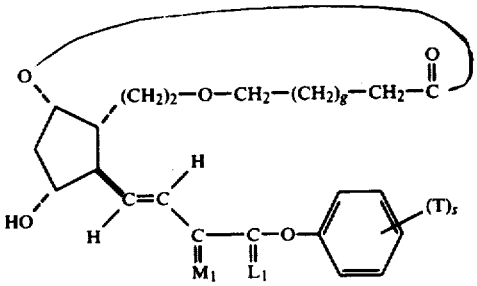
5-oxa-PGF$_{1\alpha}$-type, 1,9-lactones
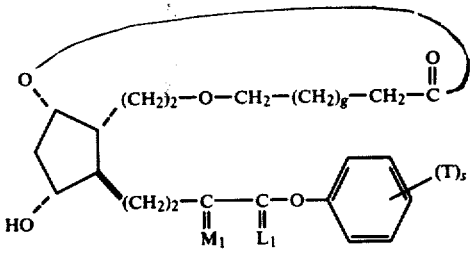
5-oxa-13,14-dihydro-PGF$_{1\alpha}$-type, 1,9-lactones
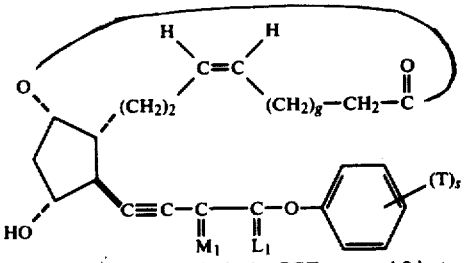
13,14-didehydro-cis-4,5-didehydro-PGF$_{1\alpha}$-type, 1,9-lactones
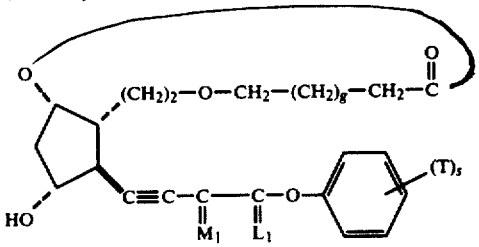
13,14-didehydro-5-oxa-PGF$_{1\alpha}$-type, 1,9-lactones
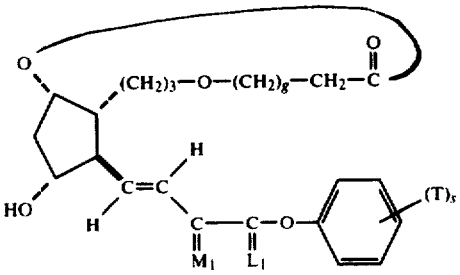
4-oxa-PGF$_{1\alpha}$-type, 1,9-lactones Table B-continued
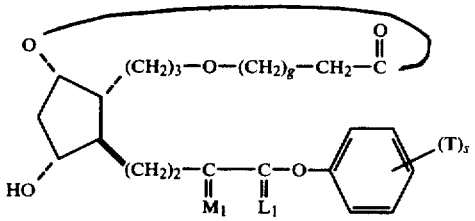
4-oxa-13,14-dihydro-PGF$_{1\alpha}$-type, 1,9-lactones
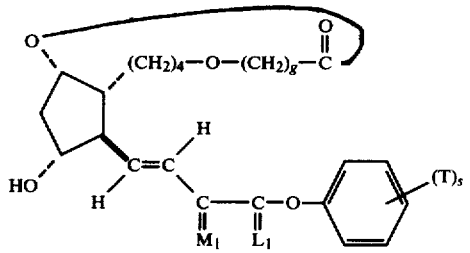
3-oxa-PGF$_{1\alpha}$-type, 1,9-lactones
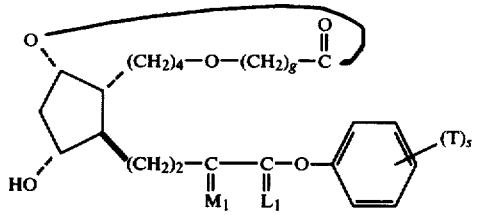
3-oxa-13,14-dihydro-PGF$_{1\alpha}$-type, 1,9-lactones
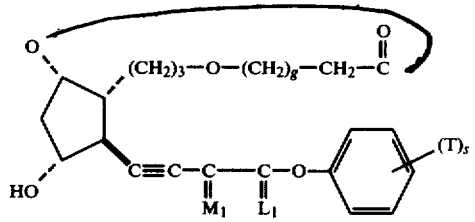
13,14-didehydro-4-oxa-PGF$_{1\alpha}$-type, 1,9-lactones
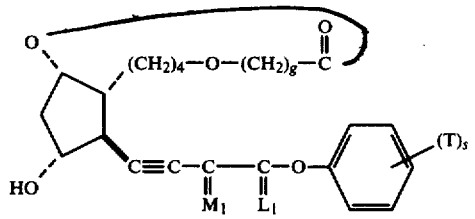
13,14-didehydro-3-oxa-PGF$_{1\alpha}$-type, 1,9-lactones
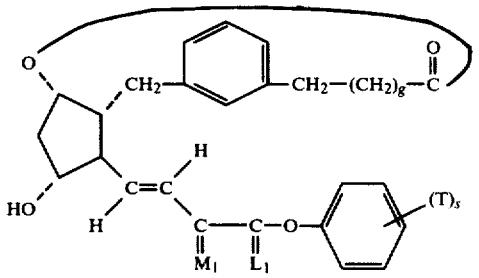
3,7-inter-m-phenylene-4,5,6-trinor-PGF$_{1\alpha}$-type, 1,9-lactones Table B-continued

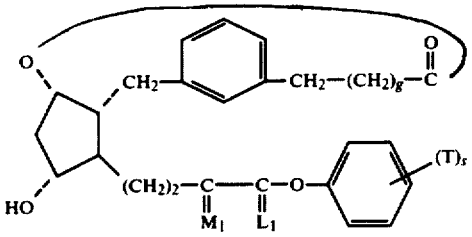

3,7-inter-m-phenylene-4,5,6-trinor-13,14-dihydro-PGF$_{1\alpha}$-type, 1,9-lactones

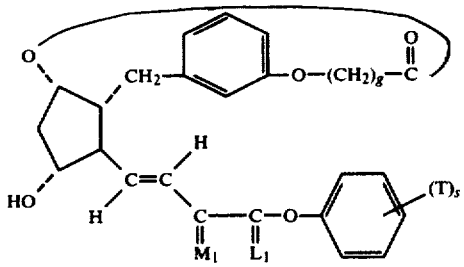

3,7-inter-m-phenylene-3-oxa-4,5,6-trinor-PGF$_{1\alpha}$-type, 1,9-lactones

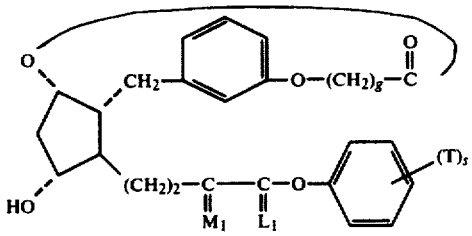

3,7-inter-m-phenylene-3-oxa-4,5,6-trinor-13,14-dihydro-PGF$_{1\alpha}$-type, 1,9-lactones

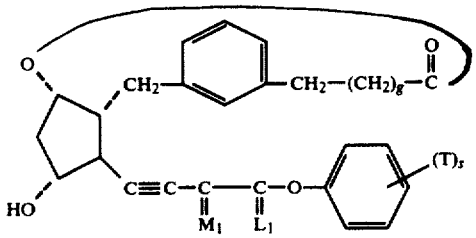

13,14-didehydro-3,7-inter-m-phenylene-4,5,6-trinor-PGF$_{1\alpha}$-type, 1,9-lactones

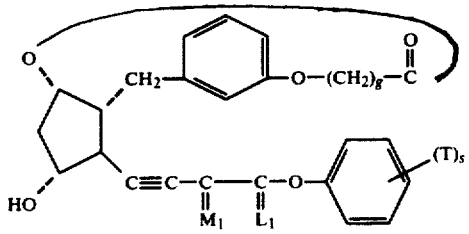

13,14-didehydro-3,7-inter-m-phenylene-3-oxa-4,5,6-trinor-PGF$_{1\alpha}$-type, 1,9-lactones

| | | | | L$_1$ | | M$_1$ | | |
|---|---|---|---|---|---|---|---|---|
| Example | g | s | T | R$_3$ | R$_4$ | R$_5$ | ~OH | Name |
| B-1 | 1 | 0 | | hydrogen | hydrogen | hydrogen | α | 16-phenoxy-17,18,19,20-tetranor |
| B-2 | 1 | 1 | p-fluoro | hydrogen | hydrogen | hydrogen | α | 16-(p-fluorophenoxy)-17,18,19,20-tetranor |
| B-3 | 1 | 1 | m-chloro | hydrogen | hydrogen | hydrogen | α | 16-(m-chlorophenoxy)-17,18,19,20-tetranor |

Table B-continued

| | | | | | | | | |
|---|---|---|---|---|---|---|---|---|
| B-4 | 1 | 1 | m-trifluoro-methyl | hydrogen | hydrogen | hydrogen | α | 16-(m-trifluoromethylphenoxy)-17,18,19,20-tetranor |
| B-5 | 1 | 0 | | hydrogen | hydrogen | methyl | α | 15-methyl-16-phenoxy-17,18,19,20-tetranor |
| B-6 | 1 | 1 | p-fluoro | hydrogen | hydrogen | methyl | α | 15-methyl-16-(p-fluorophenoxy)-17,18,19,20-tetranor |
| B-7 | 1 | 1 | m-chloro | hydrogen | hydrogen | methyl | α | 15-methyl-16-(m-chlorophenoxy)-17,18,19,20-tetranor |
| B-8 | 1 | 1 | m-trifluoro-methyl | hydrogen | hydrogen | methyl | α | 15-methyl-16-(m-trifluoromethyl-phenoxy)-17,18,19,20-tetranor |
| B-9 | 1 | 0 | | hydrogen | hydrogen | hydrogen | β | 15-epi-16-phenoxy-17,18,19,20-tetranor |
| B-10 | 1 | 1 | p-fluoro | hydrogen | hydrogen | hydrogen | β | 15-epi-16-(p-fluorophenoxy)-17,18,19,20-tetranor |
| B-11 | 1 | 1 | m-chloro | hydrogen | hydrogen | hydrogen | β | 15-epi-16-(m-chlorophenoxy)-17,18,19,20-tetranor |
| B-12 | 1 | 1 | m-trifluoro-methyl | hydrogen | hydrogen | hydrogen | β | 15-epi-16-(m-trifluoromethylphen-oxy)-17,18,19,20-tetranor |
| B-13 | 1 | 0 | | methyl | methyl | hydrogen | α | 16-methyl-16-phenoxy-18,19,20-trinor |
| B-14 | 1 | 1 | p-fluoro | methyl | methyl | hydrogen | α | 16-methyl-16-(p-fluorophenoxy)-18,19,20-trinor |
| B-15 | 1 | 1 | m-chloro | methyl | methyl | hydrogen | α | 16-methyl-16-(m-chlorophenoxy)-18,19,20-trinor |
| B-16 | 1 | 1 | m-trifluoro-methyl | methyl | methyl | hydrogen | α | 16-methyl-16-(m-trifluoromethyl-phenoxy)-18,19,20-trinor |
| B-17 | 1 | 0 | | methyl | methyl | methyl | α | 15,16-dimethyl-16-phenoxy-18,19,20-trinor |
| B-18 | 1 | 1 | p-fluoro | methyl | methyl | methyl | α | 15,16-dimethyl-16-(p-fluorophen-oxy)-18,19,20-trinor |
| B-19 | 1 | 1 | m-chloro | methyl | methyl | methyl | α | 15,16-dimethyl-16-(m-chlorophenoxy)-18,19,20-trinor |
| B-20 | 1 | 1 | m-trifluoro-methyl | methyl | methyl | methyl | α | 15,16-dimethyl-16-(m-trifluoro-methylphenoxy)-18,19,20-trinor |
| B-21 | 1 | 0 | | methyl | methyl | hydrogen | β | 16-methyl-16-phenoxy-18,19,20-trinor |
| B-22 | 1 | 1 | p-fluoro | methyl | methyl | hydrogen | α | 15-epi-16-methyl-16-(p-fluorophen-oxy)-18,19,20-trinor |
| B-23 | 1 | 1 | m-chloro | methyl | methyl | hydrogen | β | 15-epi-16-methyl-16-(m-chlorophen-oxy)-18,19,20-trinor |
| B-24 | 1 | 1 | m-trifluoro-methyl | methyl | methyl | hydrogen | β | 15-epi-16-methyl-16-(m-trifluoro-methylphenoxy)-18,19,20-trinor |
| B-25 | 3 | 0 | | hydrogen | hydrogen | hydrogen | α | 2a,2b-dihomo-16-phenoxy-17,18,19,20-tetranor |
| B-26 | 3 | 1 | p-fluoro | hydrogen | hydrogen | hydrogen | α | 2a,2b-dihomo-16-(p-fluorophenoxy)-17,18,19,20-tetranor |
| B-27 | 3 | 1 | m-chloro | hydrogen | hydrogen | hydrogen | α | 2a,2b-dihomo-16-(m-chlorophenoxy)-17,18,19,20-tetranor |
| B-28 | 3 | 1 | m-trifluoro-methyl | hydrogen | hydrogen | hydrogen | α | 2a,2b-dihomo-16-(m-trifluoromethyl-phenoxy)-17,18,19,20-tetranor |
| B-29 | 3 | 0 | | hydrogen | hydrogen | methyl | α | 2a,2b-dihomo-15-methyl-16-phenoxy-17,18,19,20-tetranor |
| B-30 | 3 | 1 | p-fluoro | hydrogen | hydrogen | methyl | α | 2a,2b-dihomo-15-methyl-16-(p-fluoro-phenoxy)-17,18,19,20-tetranor |
| B-31 | 3 | 1 | m-chloro | hydrogen | hydrogen | methyl | α | 2a,2b-dihomo-15-methyl-16-(m-chloro-phenoxy)-17,18,19,20-tetranor |
| B-32 | 3 | 1 | m-trifluoro-methyl | hydrogen | hydrogen | methyl | α | 2a,2b-dihomo-15-methyl-16-(m-tri-fluoromethylphenoxy)-17,18,19,20-tetranor |

Table C

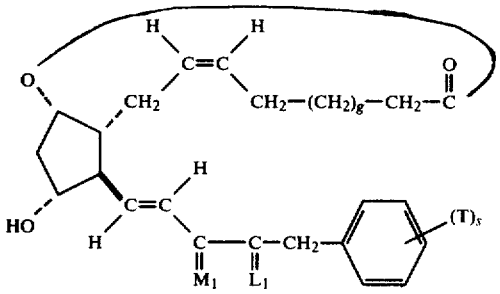

18,19,20-trinor-PGF$_{2\alpha}$-type, 1,9-lactones

Table C-continued
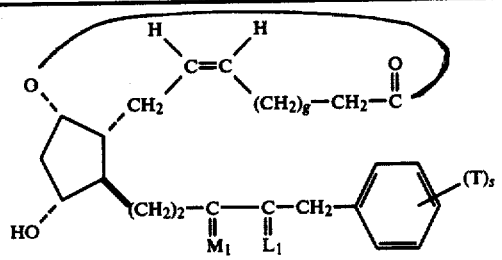
18,19,20-trinor-13,14-dihydro-PGF$_{2\alpha}$-type,
1,9-lactones
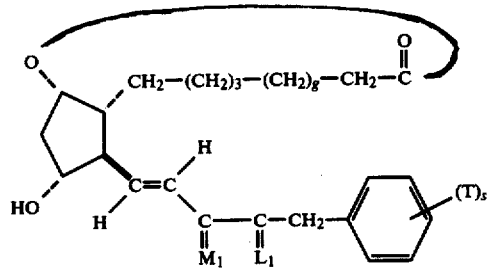
18,19,20-trinor-PGF$_{1\alpha}$-type,
1,9-lactones
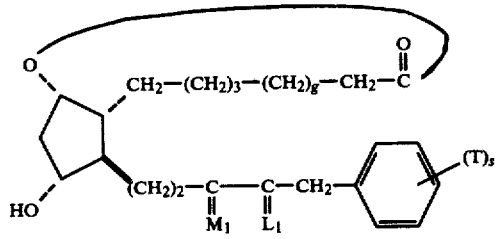
18,19,20-trinor-13,14-dihydro-PGF$_{1\alpha}$-type,
1,9-lactones
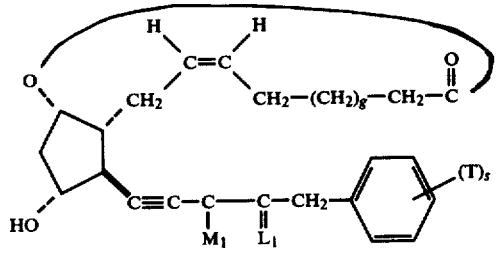
13,14-didehydro-18,19,20-trinor-PGF$_{2\alpha}$-type,
1,9-lactones
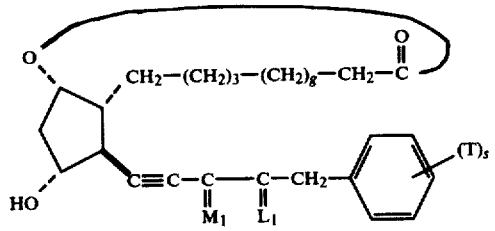
13,14-didehydro-18,19,20-trinor-PGF$_{1\alpha}$-type,
1,9-lactones Table C-continued
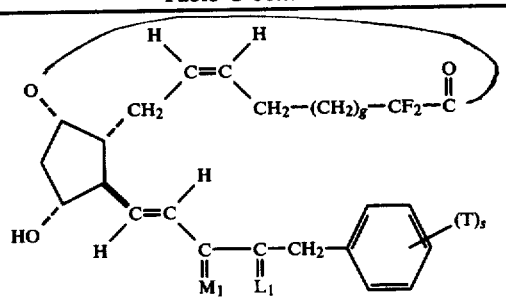
18,19,20-trinor-2,2-difluoro-$PGF_{2\alpha}$-type, 1,9-lactones
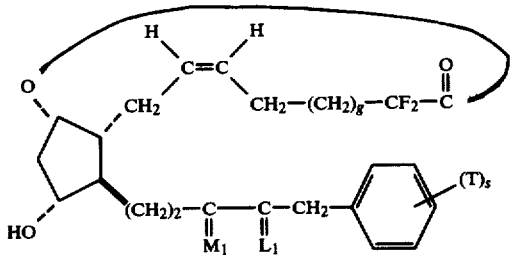
18,19,20-trinor-2,2-difluoro-13,14-dihydro-$PGF_{2\alpha}$-type, 1,9-lactones
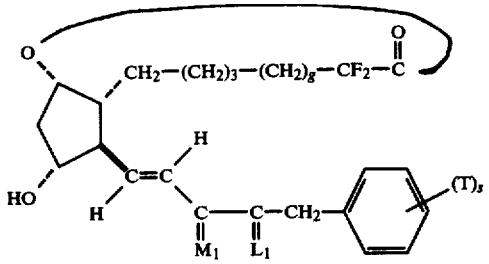
18,19,20-trinor-2,2-difluoro-$PGF_{1\alpha}$-type, 1,9-lactones
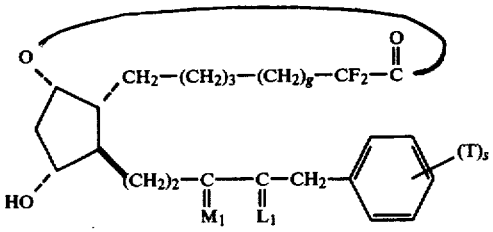
18,19,20-trinor-2,2-difluoro-13,14-dihydro-$PGF_{1\alpha}$-type, 1,9-lactones
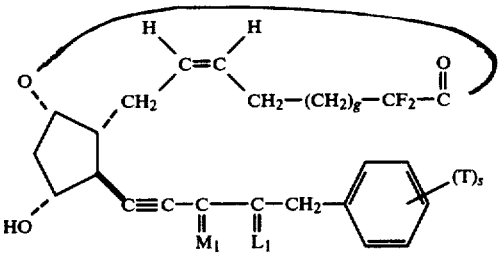
13,14-didehydro-18,19,20-trinor-2,2-difluoro-$PGF_{2\alpha}$-type, 1,9-lactones Table C-continued
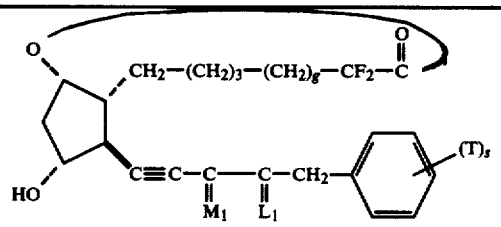
13,14-didehydro-18,19,20-trinor-2,2-difluoro-$PGF_{1\alpha}$-type, 1,9-lactones
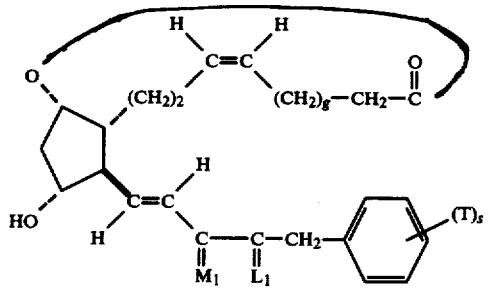
18,19,20-trinor-cis-4,5-didehydro-$PGF_{1\alpha}$-type, 1,9-lactones
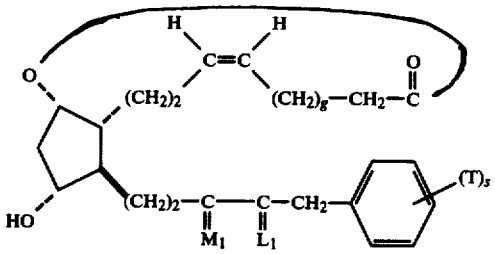
18,19,20-trinor-cis-4,5-didehydro-13,14-dihydro-$PGF_{1\alpha}$-type, 1,9-lactones
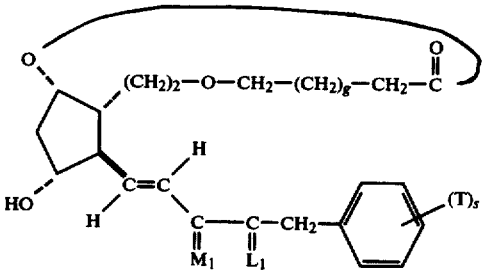
18,19,20-trinor-5-oxa-$PGF_{1\alpha}$-type, 1,9-lactones
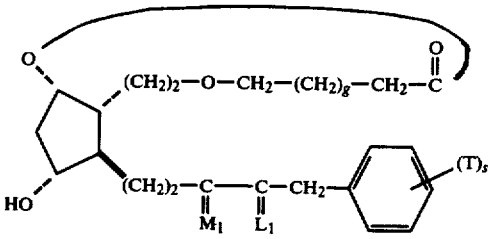
18,19,20-trinor-5-oxa-13,14-dihydro-$PGF_{1\alpha}$-type, 1,9-lactones Table C-continued
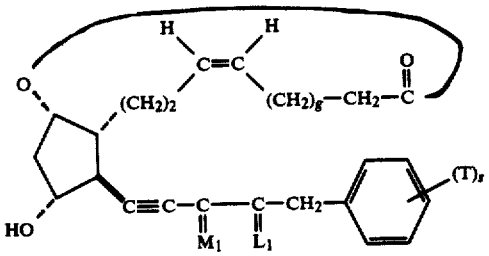
13,14-didehydro-18,19,20-trinor-cis-4,5-didehydro-PGF$_{1\alpha}$-type, 1,9-lactones
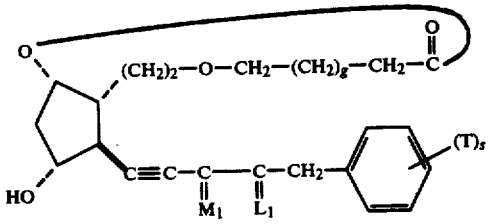
13,14-didehydro-18,19,20-trinor-5-oxa-PGF$_{1\alpha}$-type, 1,9-lactones
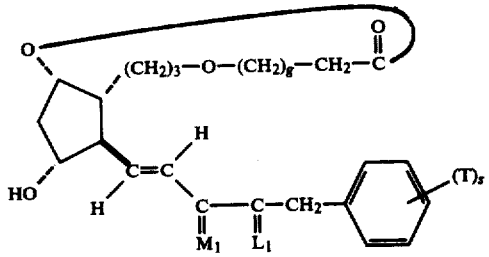
18,19,20-trinor-4-oxa-PGF$_{1\alpha}$-type, 1,9-lactones
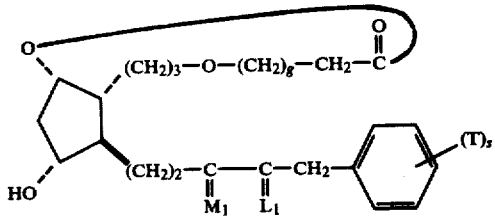
18,19,20-trinor-4-oxa-13,14-dihydro-PGF$_{1\alpha}$-type, 1,9-lactones
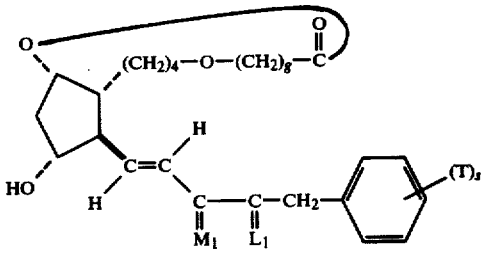
18,19,20-trinor-3-oxa-PGF$_{1\alpha}$-type, 1,9-lactones
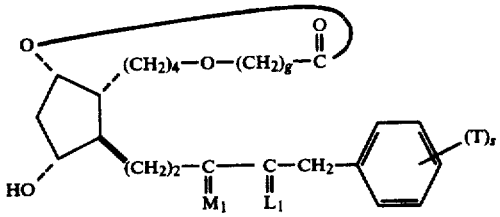
18,19,20-trinor-3-oxa-13,14-dihydro-PGF$_{1\alpha}$-type, 1,9-lactones Table C-continued
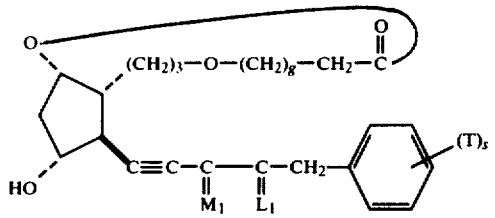
13,14-didehydro-18,19,20-trinor-4-oxa-PGF$_{1\alpha}$-type, 1,9-lactones
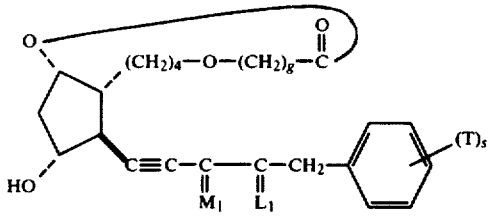
13,14-didehydro-18,19,20-trinor-3-oxa-PGF$_{1\alpha}$-type, 1,9-lactones
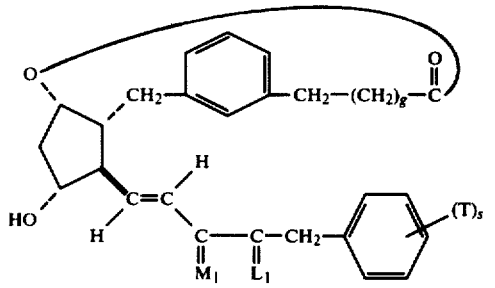
3,7-inter-m-phenylene-4,5,6,18,19,20-hexanor-PGF$_{1\alpha}$-type, 1,9-lactones
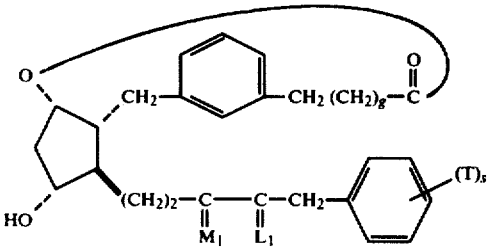
3,7-inter-m-phenylene-4,5,6,18,19,20-hexanor-13,14-dihydro-PGF$_{1\alpha}$-type, 1,9-lactones
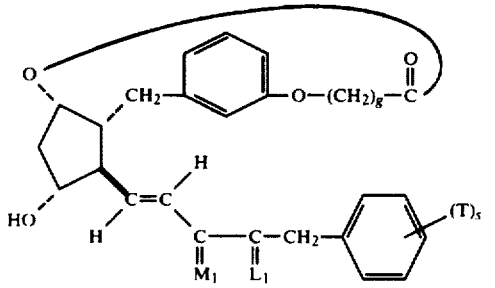
3,7-inter-m-phenylene-3-oxa-4,5,6,18,19,20-hexanor-PGF$_{1\alpha}$-type, 1,9-lactones Table C-continued

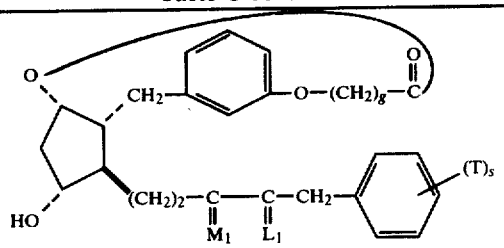

3,7-inter-m-phenylene-3-oxa-4,5,6,18,19,20-hexanor-13,14-dihydro-PGF$_{1\alpha}$-type, 1,9-lactones

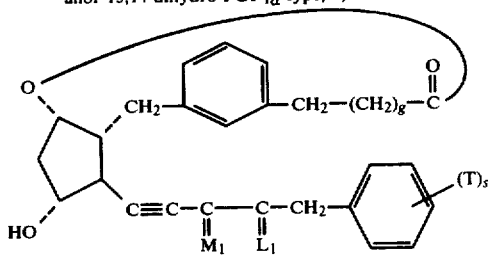

13,14-didehydro-3,7-inter-m-phenylene-4,5,6,18,19,20-hexanor-PGF$_{1\alpha}$-type, 1,9-lactones

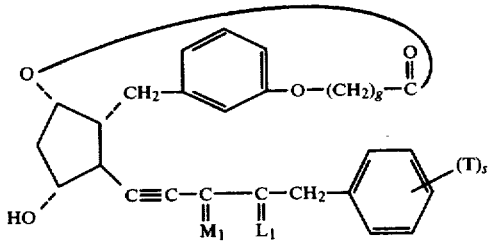

13,14-didehydro-3,7-inter-m-phenylene-3-oxa-4,5,6,18,19,20-hexanor-PGF$_{1\alpha}$-type, 1,9-lactones

| | | | | $L_1$ | $M_1$ | | | |
|---|---|---|---|---|---|---|---|---|
| Example | g | s | T | $R_3$ | $R_4$ | $R_5$ | ~OH | Name |
| C-1 | 1 | 0 | | hydrogen | hydrogen | hydrogen | α | 17-phenyl |
| C-2 | 1 | 1 | p-fluoro | hydrogen | hydrogen | hydrogen | α | 17-(p-fluorophenyl) |
| C-3 | 1 | 1 | m-chloro | hydrogen | hydrogen | hydrogen | α | 17-(m-chlorophenyl) |
| C-4 | 1 | 1 | m-trifluoro-methyl | hydrogen | hydrogen | hydrogen | α | 17-(m-trifluoromethylphenyl) |
| C-5 | 1 | 0 | | hydrogen | hydrogen | methyl | α | 15-methyl-17-phenyl |
| C-6 | 1 | 1 | p-fluoro | hydrogen | hydrogen | methyl | α | 15-methyl-17-(p-fluorophenyl) |
| C-7 | 1 | 1 | m-chloro | hydrogen | hydrogen | methyl | α | 15-methyl-17-(m-chlorophenyl) |
| C-8 | 1 | 1 | m-trifluoro-methyl | hydrogen | hydrogen | methyl | α | 15-methyl-17-(m-trifluoromethyl-phenyl) |
| C-9 | 1 | 0 | | hydrogen | hydrogen | hydrogen | β | 15-epi-17-phenyl |
| C-10 | 1 | 1 | p-fluoro | hydrogen | hydrogen | hydrogen | β | 15-epi-17-(p-fluorophenyl) |
| C-11 | 1 | 1 | m-chloro | hydrogen | hydrogen | hydrogen | β | 15-epi-17-(m-chlorophenyl) |
| C-12 | 1 | 1 | m-trifluoro-methyl | hydrogen | hydrogen | hydrogen | β | 15-epi-17-(m-trifluoromethyl-phenyl) |
| C-13 | 1 | 0 | | methyl | methyl | hydrogen | α | 16,16-dimethyl-17-phenyl |
| C-14 | 1 | 1 | p-fluoro | methyl | methyl | hydrogen | α | 16,16-dimethyl-17-(p-fluorophenyl) |
| C-15 | 1 | 1 | m-chloro | methyl | methyl | hydrogen | α | 16,16-dimethyl-17-(m-chlorophenyl) |
| C-16 | 1 | 1 | m-trifluoro-methyl | methyl | methyl | hydrogen | α | 16,16-dimethyl-17-(m-trifluoro-methylphenyl) |
| C-17 | 1 | 0 | | methyl | methyl | methyl | α | 15,16,16-trimethyl-17-phenyl |
| C-18 | 1 | 1 | p-fluoro | methyl | methyl | methyl | α | 15,16,16-trimethyl-17-(p-fluoro-phenyl) |
| C-19 | 1 | 1 | m-chloro | methyl | methyl | methyl | α | 15,16,16-trimethyl-17-(m-chloro-phenyl) |
| C-20 | 1 | 1 | m-trifluoro-methyl | methyl | methyl | methyl | α | 15,16,16-trimethyl-17-(m-trifluoro-methylphenyl) |
| C-21 | 1 | 0 | | methyl | methyl | hydrogen | β | 15-epi-16,16-dimethyl-17-phenyl |
| C-22 | 1 | 1 | p-fluoro | methyl | methyl | hydrogen | β | 15-epi-16,16-dimethyl-17-(p-fluoro-phenyl) |
| C-23 | 1 | 1 | m-chloro | methyl | methyl | hydrogen | β | 15-epi-16,16-dimethyl-17-(m-chloro-phenyl) |
| C-24 | 1 | 1 | m-trifluoro-methyl | methyl | methyl | hydrogen | β | 15-epi-16,16-dimethyl-17-(m-tri-fluoromethylphenyl) |
| C-25 | 3 | 0 | | hydrogen | hydrogen | hydrogen | α | 2a,2b-dihomo-17-phenyl |

Table C-continued

| | | | | | | | | |
|---|---|---|---|---|---|---|---|---|
| C-26 | 3 | 1 | p-fluoro | hydrogen | hydrogen | hydrogen | α | 2a,2b-dihomo-17-(p-fluorophenyl) |
| C-27 | 3 | 1 | m-chloro | hydrogen | hydrogen | hydrogen | α | 2a,2b-dihomo-17-(m-chlorophenyl) |
| C-28 | 3 | 1 | m-trifluoro-methyl | hydrogen | hydrogen | hydrogen | α | 2a,2b-dihomo-17-(m-trifluoromethyl-phenyl) |
| C-29 | 3 | 0 | | hydrogen | hydrogen | methyl | α | 2a,2b-dihomo-15-methyl-17-phenyl |
| C-30 | 3 | 1 | p-fluoro | hydrogen | hydrogen | methyl | α | 2a,2b-dihomo-15-methyl-17-(p-fluorophenyl) |
| C-31 | 3 | 1 | m-chloro | hydrogen | hydrogen | methyl | α | 2a,2b-dihomo-15-methyl-17-(m-chlorophenyl) |
| C-32 | 3 | 1 | m-trifluoro-methyl | hydrogen | hydrogen | methyl | α | 2a,2b-dihomo-15-methyl-17-(m-tri-fluoromethylphenyl) |
| C-33 | 1 | 0 | | fluoro | fluoro | hydrogen | α | 16,16-difluoro-17-phenyl |
| C-34 | 1 | 1 | p-fluoro | fluoro | fluoro | hydrogen | α | 16,16-difluoro-17-(p-fluorophenyl) |
| C-35 | 1 | 1 | m-chloro | fluoro | fluoro | hydrogen | α | 16,16-difluoro-17-(m-chlorophenyl) |
| C-36 | 1 | 1 | m-trifluoro-methyl | fluoro | fluoro | hydrogen | α | 16,16-difluoro-17-(m-trifluoro-methylphenyl) |
| C-37 | 1 | 0 | | fluoro | fluoro | methyl | α | 15-methyl-16,16-difluoro-17-phenyl |
| C-38 | 1 | 1 | p-fluoro | fluoro | fluoro | methyl | α | 15-methyl-16,16-difluoro-17-(p-fluorophenyl) |
| C-39 | 1 | 1 | m-chloro | fluoro | fluoro | methyl | α | 15-methyl-16,16-difluoro-17-(m-chlorophenyl |
| C-40 | 1 | 1 | m-trifluoro-methyl | fluoro | fluoro | methyl | α | 15-methyl-16,16-difluoro-17-(m-trifluoromethylphenyl) |
| C-41 | 1 | 0 | | fluoro | fluoro | hydrogen | α | 16,16-difluoro-17-phenyl |
| C-42 | 1 | 1 | p-fluoro | fluoro | fluoro | hydrogen | α | 16,16-difluoro-17-(p-fluorophenyl) |
| C-43 | 1 | 1 | m-chloro | fluoro | fluoro | hydrogen | β | 15-epi-16,16-difluoro-17-(m-chloro-phenyl |
| C-44 | 1 | 1 | m-trifluoro-methyl | fluoro | fluoro | hydrogen | β | 15-epi-16,16-difluoro-17-(m-tri-fluoromethylphenyl) |

Table D

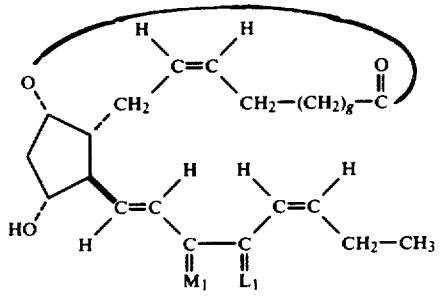

$PGF_{3\alpha}$-type, 1,9-lactones

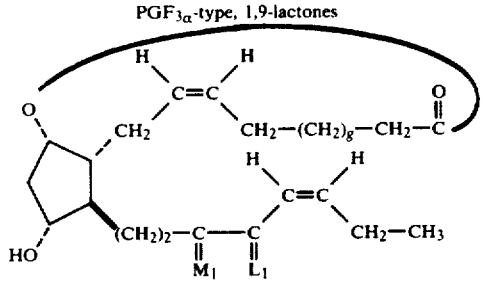

13,14-dihydro-$PGF_{3\alpha}$-type, 1,9-lactones

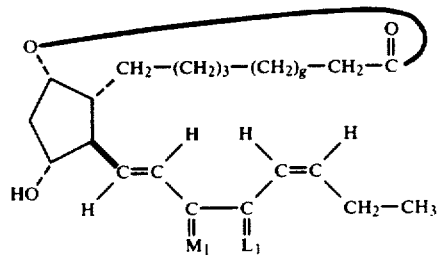

5,6-dihydro-$PGF_{3\alpha}$-type, 1,9-lactones

Table D-continued
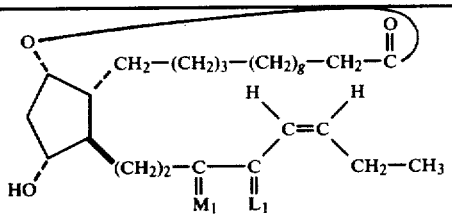
5,6,13,14-tetrahydro-PGF$_{3\alpha}$-type, 1,9-lactones
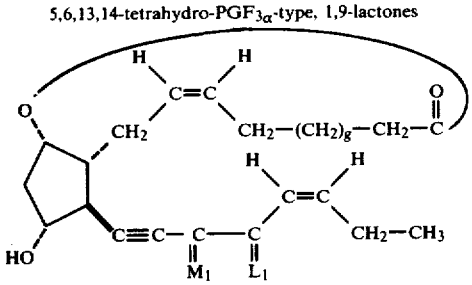
13,14-didehydro-PGF$_{3\alpha}$-type, 1,9-lactones
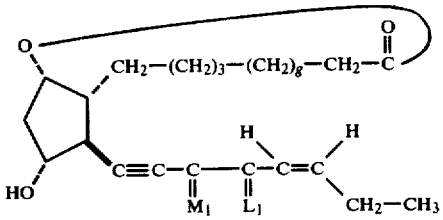
13,14-didehydro-5,6-dihydro-PGF$_{3\alpha}$-type, 1,9-lactones
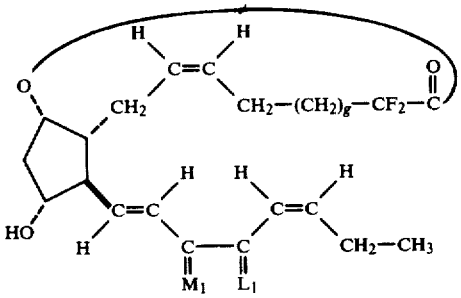
2,2-difluoro-PGF$_{3\alpha}$-type, 1,9-lactones
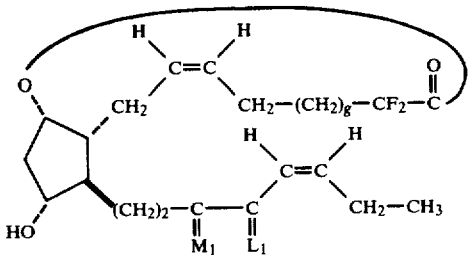
2,2-difluoro-13,14-dihydro-PGF$_{3\alpha}$-type, 1,9-lactones
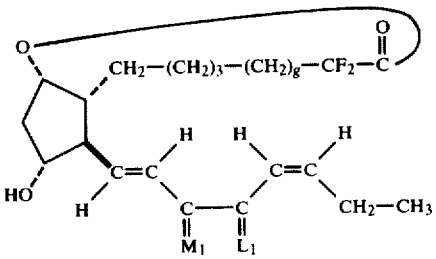
2,2-difluoro-5,6-dihydro-PGF$_{3\alpha}$-type, 1,9-lactones Table D-continued
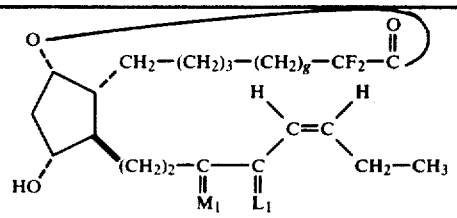
2,2-difluoro-5,6,13,14-tetrahydro-PGF$_{3\alpha}$ -type, 1,9-lactones
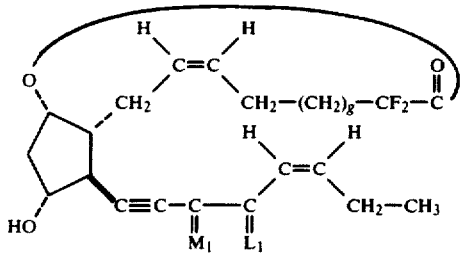
13,14-didehydro-2,2-difluoro-PGF$_{3\alpha}$-types 1,9-lactones
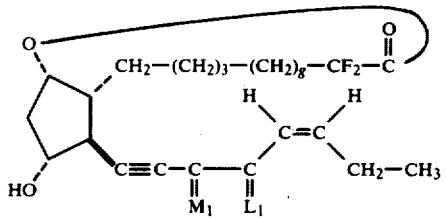
13,14-didehydro-2,2-difluoro-5,6-dihydro-PGF$_{3\alpha}$-type, 1,9-lactones
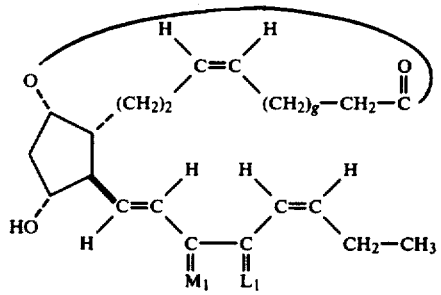
cis,cis-4,5,17,18-tetradehydro-PGF$_{1\alpha}$-type, 1,9-lactones
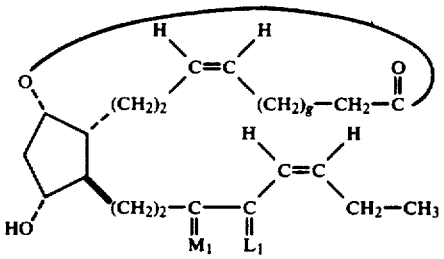
cis,cis-4,5,17,18-tetradehydro-13,14-dihydro-PGF$_{1\alpha}$-type, 1,9-lactones
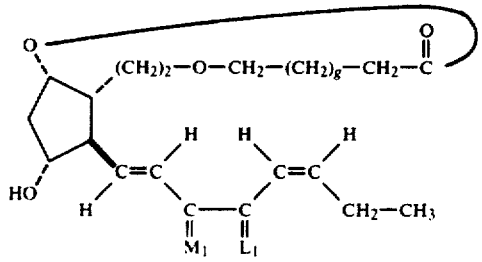

Table D-continued 5-oxa-cis-17,18-didehydro-PGF$_{1\alpha}$-type, 1,9-lactones

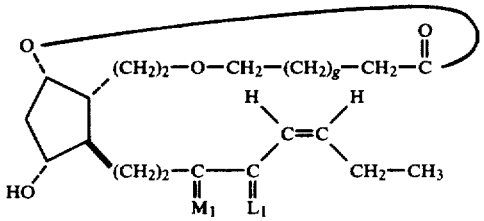

5-oxa-13,14-dihydro-cis-17,18-didehydro-PGF$_{1\alpha}$-type, 1,9-lactones

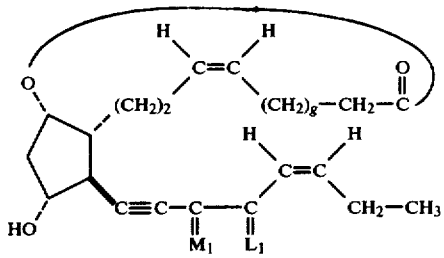

13,14-didehydro-cis,cis-4,5,17,18-tetradehydro-PGF$_{1\alpha}$-type, 1,9-lactones

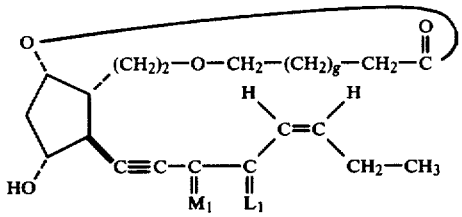

13,14-didehydro-5-oxa-cis-17,18-didehydro-PGF$_{1\alpha}$-type, 1,9-lactones

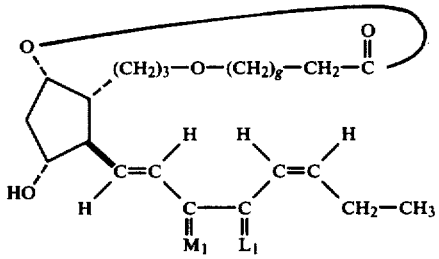

4-oxa-cis-17,18-didehydro-PGF$_{1\alpha}$-type, 1,9-lactones

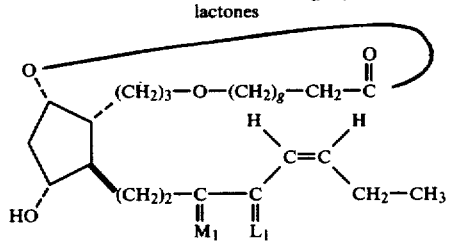

4-oxa-13,14-dihydro-17,18-didehydro-PGF$_{1\alpha}$-type, 1,9-lactones

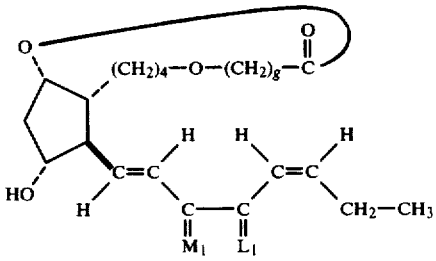

3-oxa-cis-17,18-didehydro-PGF$_{1\alpha}$-type, 1,9-lactones

Table D-continued
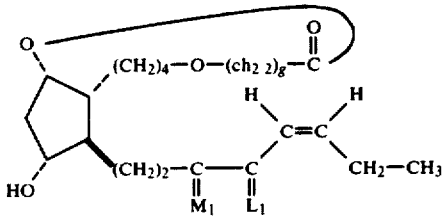
3-oxa-13,14-dihydro-cis-17,18-didehydro-PGF$_{1\alpha}$-type, 1,9-lactones
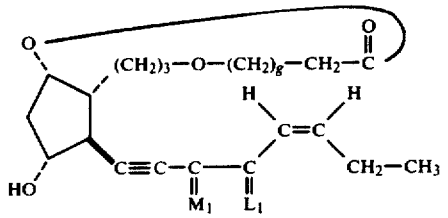
13,14-didehydro-4-oxa-cis-17,18-didehydro-PGF$_{1\alpha}$-type, 1,9-lactones
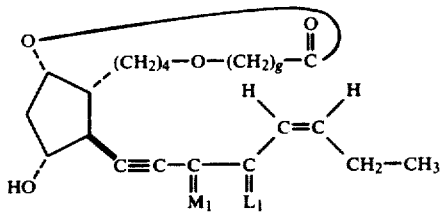
13,14-didehydro-3-oxa-cis-17,18-didehydro-PGF$_{1\alpha}$-type, 1,9-lactones
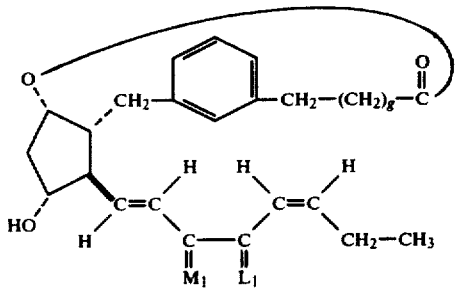
3,7-inter-m-phenylene-4,5,6-trinor-cis-17,18-didehydro-PGF$_{1\alpha}$-type, 1,9-lactones
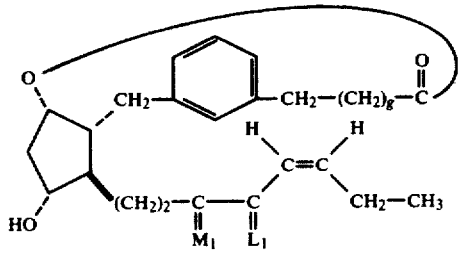
3,7-inter-m-phenylene-4,5,6-trinor-13,14-dihydro-cis-17,18-didehydro-PGF$_{1\alpha}$-type, 1,9-lactones
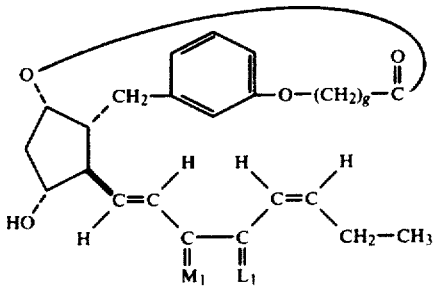

Table D-continued 3,7-inter-m-phenylene-3-oxa-4,5,6-trinor-cis-17,18-didehydro-PGF$_{1\alpha}$-type, 1,9-lactones

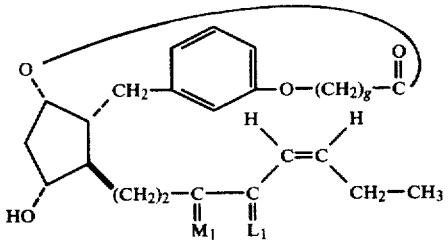

3,7-inter-m-phenylene-3-oxa-4,5,6-trinor-13,14-dihydro-cis-17,18-didehydro-PGF$_{1\alpha}$-type, 1,9-lactones

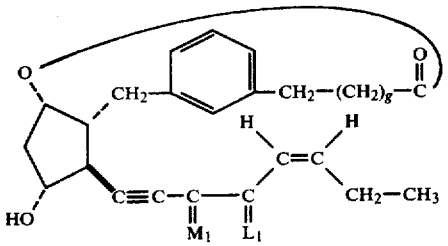

13,14-didehydro-3,7-inter-m-phenylene-4,5,6-trinor-cis-17,18-didehydro-PGF$_{1\alpha}$-type, 1,9-lactones

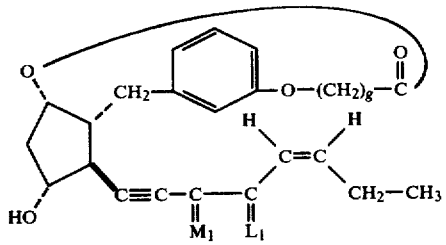

13,14-didehydro-3,7-inter-m-phenylene-3-oxa-4,5,6-trinor-cis-17,18-didehydro-PGF$_{1\alpha}$-type, 1,9-lactones

| | | $L_1$ | $M_1$ | | | |
|---|---|---|---|---|---|---|
| Example | g | $R_3$ | $R_4$ | $R_5$ | ~OH | Name |
| D-1 | 1 | methyl | hydrogen | hydrogen | α | 16-methyl |
| D-2 | 1 | methyl | hydrogen | methyl | α | 15,16-dimethyl |
| D-3 | 1 | methyl | hydrogen | hydrogen | β | 15-epi-16-methyl |
| D-4 | 1 | methyl | methyl | hydrogen | α | 16,16-dimethyl |
| D-5 | 1 | methyl | methyl | methyl | α | 15,16,16-trimethyl |
| D-6 | 1 | methyl | methyl | hydrogen | α | 16,16-dimethyl |
| D-7 | 1 | fluoro | hydrogen | hydrogen | β | 15-epi-16-fluoro |
| D-8 | 1 | fluoro | hydrogen | methyl | α | 15-methyl-16-fluoro |
| D-9 | 1 | fluoro | hydrogen | hydrogen | β | 15-epi-16-fluoro |
| D-10 | 1 | fluoro | fluoro | hydrogen | α | 16,16-difluoro |
| D-11 | 1 | fluoro | fluoro | methyl | α | 15-methyl-16,16-difluoro |
| D-12 | 1 | fluoro | fluoro | hydrogen | β | 15-epi-16,16-difluoro |
| D-13 | 1 | hydrogen | hydrogen | hydrogen | α | (title compound) |
| D-14 | 1 | hydrogen | hydrogen | methyl | α | 15-methyl |
| D-15 | 3 | hydrogen | hydrogen | hydrogen | α | 2a,2b-dihomo |
| D-16 | 3 | hydrogen | hydrogen | methyl | α | 2a,2b-dihomo-15-methyl |
| D-17 | 3 | methyl | methyl | hydrogen | α | 2a,2b-dihomo-16,16-dimethyl |
| D-18 | 3 | methyl | methyl | methyl | α | 2a,2b-dihomo-15,16,16-trimethyl |
| D-19 | 3 | fluoro | fluoro | hydrogen | α | 2a,2b-dihomo-16,16-difluoro |
| D-20 | 3 | fluoro | fluoro | methyl | α | 2a,2b-dihomo-15-methyl-16,16-difluoro |

Table E
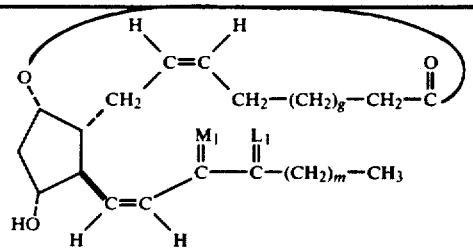
cis-13-$PGF_{2\alpha}$-type, 1,9-lactones
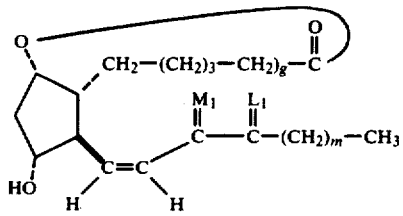
cis-13-$PGF_{1\alpha}$-type, 1,9-lactones
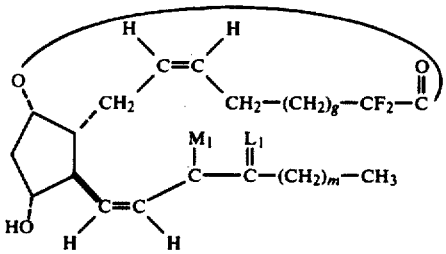
2,2-difluoro-cis-13-$PGF_{2\alpha}$-type, 1,9-lactones
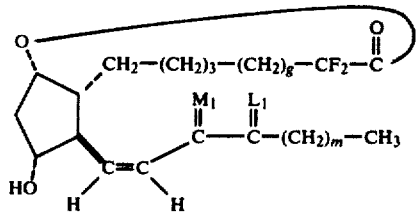
2,2-difluoro-cis-13-$PGF_{1\alpha}$-type, 1,9-lactones
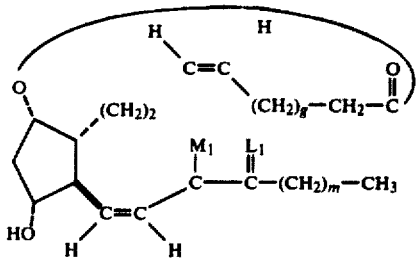
cis-4,5-didehydro-cis-13-$PGF_{1\alpha}$-type, 1,9-lactones
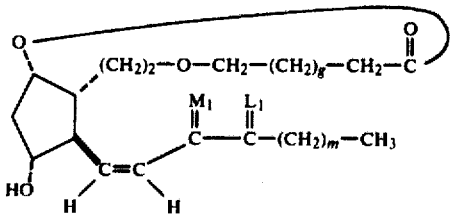
5-oxa-cis-13-$PGF_{1\alpha}$-type, 1,9-lactones Table E-continued

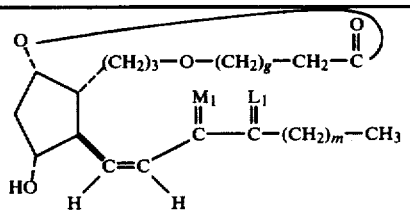

5-oxa-cis-13-PGF$_{1\alpha}$-type, 1,9-lactones

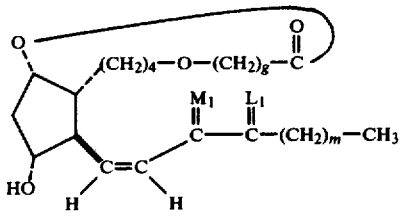

3-oxa-cis-13-PGF$_{1\alpha}$-type, 1,9-lactones

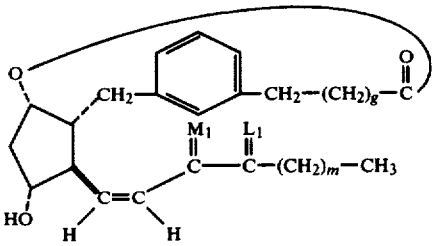

3,7-inter-m-phenylene-4,5,6-trinor-cis-13-PGF$_{1\alpha}$-type, 1,9-lactones

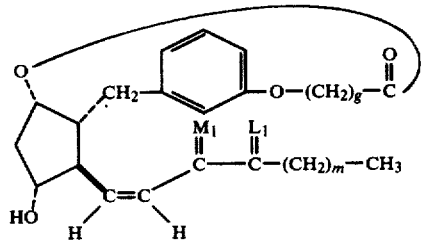

3,7-inter-m-phenylene-3-oxa-4,5,6-trinor-cis-13-PGD$_1$-type, 1,9-lactones

| | | | $L_1$ | | | | |
|---|---|---|---|---|---|---|---|
| Example | g | m | $R_3$ | $R_4$ | $R_5$ | ~O | Name |
| E-1 | 1 | 3 | methyl | hydrogen | hydrogen | α | 15-epi-16-methyl |
| E-2 | 1 | 3 | methyl | hydrogen | methyl | α | 15-epi-15,16-dimethyl |
| E-3 | 1 | 3 | methyl | hydrogen | hydrogen | β | 16-methyl |
| E-4 | 1 | 3 | methyl | methyl | hydrogen | α | 15-epi-16,16-dimethyl |
| E-5 | 1 | 3 | methyl | methyl | methyl | α | 15-epi-15,16,16-trimethyl |
| E-6 | 1 | 3 | methyl | methyl | hydrogen | β | 16,16-dimethyl |
| E-7 | 1 | 3 | fluoro | hydrogen | hydrogen | α | 15-epi-16-fluoro |
| E-8 | 1 | 3 | fluoro | hydrogen | methyl | α | 15-epi-15-methyl-16-fluoro |
| E-9 | 1 | 3 | fluoro | hydrogen | hydrogen | α | 15-epi-16-fluoro |
| E-10 | 1 | 3 | fluoro | fluoro | hydrogen | α | 15-epi-16,16-difluoro |
| E-11 | 1 | 3 | fluoro | fluoro | methyl | α | 15-epi-15-methyl-16,16-difluoro |
| E-12 | 1 | 3 | fluoro | fluoro | methyl | β | 15-methyl-16,16-difluoro |
| E-13 | 1 | 3 | hydrogen | hydrogen | hydrogen | α | 15-epi |
| E-14 | 3 | 3 | hydrogen | hydrogen | hydrogen | α | 15-epi-21,2b-dihomo |
| E-15 | 3 | 3 | methyl | methyl | hydrogen | α | 15-epi-2a,2b-dihomo-16,16-dimethyl |
| E-16 | 3 | 3 | methyl | methyl | methyl | α | 15-epi-2a,2b-dihomo-15,16,16-trimethyl |
| E-17 | 3 | 3 | fluoro | fluoro | hydrogen | α | 15-epi-2a,2b-dihomo-16,16-difluoro |
| E-18 | 3 | 3 | fluoro | fluoro | methyl | α | 15-epi-2a,2b-dihomo-15-methyl-16,16-difluoro |

Table F
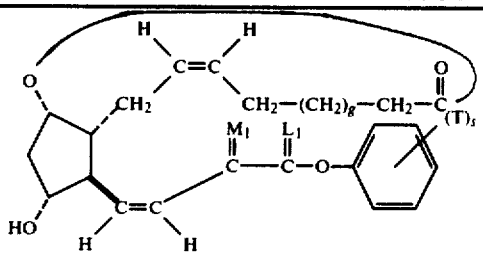
cis-13-PGF$_{2\alpha}$-type, 1,9-lactones
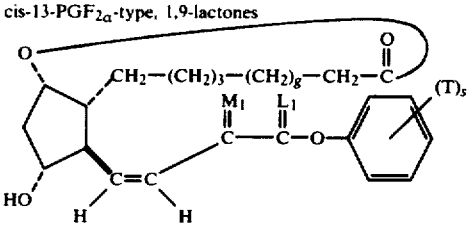
cis-13-PGF$_{1\alpha}$-type, 1,9-lactones
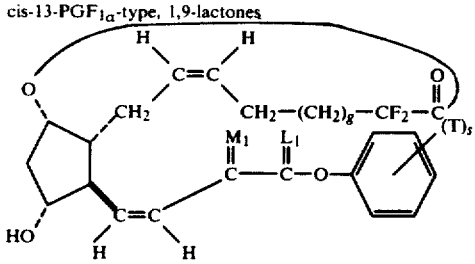
2,2-difluoro-cis-13-PGF$_{2\alpha}$-type, 1,9-lactones
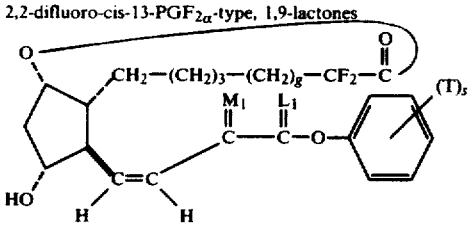
2,2-difluoro-cis-13-PGF$_{1\alpha}$-type, 1,9-lactones
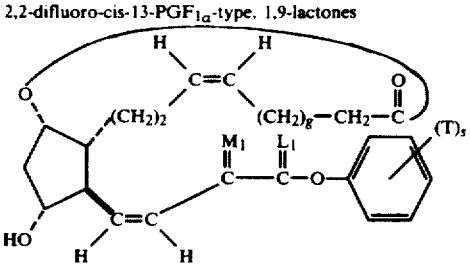
cis-4,5-didehydro-cis-13-PGF$_{1\alpha}$-type, 1,9-lactones
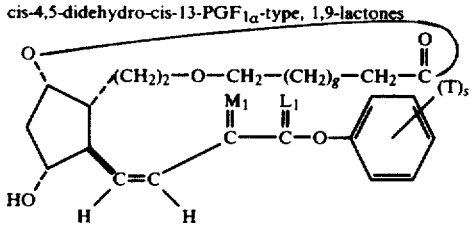
5-oxa-cis-13-PGF$_{1\alpha}$-type, 1,9-lactones
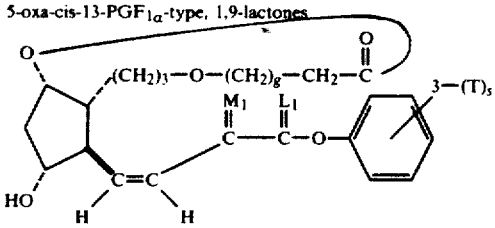
4-oxa-cis-13-PGF$_{1\alpha}$-type, 1,9-lactones Table F-continued

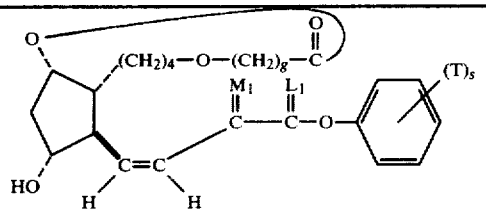

3-oxa-cis-13-PGF$_{1\alpha}$-type, 1,9-lactones

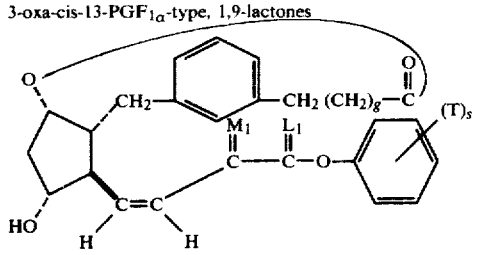

3,7-inter-m-phenylene-4,5,6-trinor-cis-13-PGF$_{1\alpha}$-type, 1,9-lactones

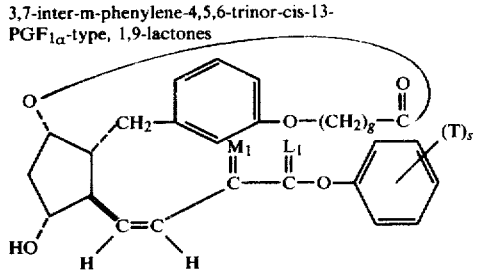

3,7-inter-m-phenylene-3-oxa-4,5,6-trinor-cis-13-PGF$_{1\alpha}$-type, 1,9-lactones

| Example | g | s | T | $R_3$ | $R_4$ | $R_5$ | $L_1$ ~O | Name |
|---|---|---|---|---|---|---|---|---|
| F-1 | 1 | 0 | | hydrogen | hydrogen | hydrogen | α | 15-epi-16-phenoxy-17,18,19,20-tetranor |
| F-2 | 1 | 1 | p-fluoro | hydrogen | hydrogen | hydrogen | α | 15-epi-16-(p-fluorophenoxy)-17,18,19,20-tetranor |
| F-3 | 1 | 1 | m-chloro | hydrogen | hydrogen | hydrogen | α | 15-epi-16-(m-chlorophenoxy)-17,18,19,20-tetranor |
| F-4 | 1 | 1 | m-trifluoromethyl | hydrogen | hydrogen | hydrogen | α | 15-epi-16-(m-trifluoromethylphenoxy)-17,18,19,20-tetranor |
| F-5 | 1 | 0 | | hydrogen | hydrogen | methyl | α | 15-epi-15-methyl-16-phenoxy-17,18,19,20-tetranor |
| F-6 | 1 | 1 | p-fluoro | hydrogen | hydrogen | methyl | α | 15-epi-15-methyl-16-(p-fluorophenoxy)-17,18,19,20-tetranor |
| F-7 | 1 | 1 | m-chloro | hydrogen | hydrogen | methyl | α | 15-epi-15-methyl-16-(m-chlorophenoxy)-17,18,19,20-tetranor |
| F-8 | 1 | 1 | m-trifluoromethyl | hydrogen | hydrogen | methyl | α | 15-epi-15-methyl-16-(m-trifluoromethylphenoxy)-17,18,19,20-tetranor |
| F-9 | 1 | 0 | | hydrogen | hydrogen | hydrogen | β | 16-phenoxy-17,18,19,20-tetranor |
| F-10 | 1 | 1 | p-fluoro | hydrogen | hydrogen | hydrogen | β | 16-(p-fluorophenoxy)-17,18,19,20-tetranor |
| F-11 | 1 | 1 | m-chloro | hydrogen | hydrogen | hydrogen | β | 16-(m-chlorophenoxy)-17,18,19,20-tetranor |
| F-12 | 1 | 1 | m-trifluoromethyl | hydrogen | hydrogen | hydrogen | β | 16-(m-trifluoromethylphenoxy)-17,18,19,20-tetranor |
| F-13 | 1 | 0 | | methyl | methyl | hydrogen | α | 15-epi-16-methyl-16-phenoxy-18,19,20-trinor |
| F-14 | 1 | 1 | p-fluoro | methyl | methyl | hydrogen | α | 15-epi-16-methyl-16-(p-fluorophenoxy)-18,19,20-trinor |
| F-15 | 1 | 1 | m-chloro | methyl | methyl | hydrogen | α | 15-epi-16-methyl-16-(m-chlorophenoxy)-18,19,20-trinor |
| F-16 | 1 | 1 | m-trifluoromethyl | methyl | methyl | hydrogen | α | 15-epi-16-methyl-16-(m-trifluoromethylphenoxy)-18,19,20-trinor |
| F-17 | 1 | 0 | | methyl | methyl | methyl | α | 15-epi-15,16-dimethyl-16-phenoxy-18,19,20-trinor |
| F-18 | 1 | 1 | p-fluoro | methyl | methyl | methyl | α | 15-epi-15,16-dimethyl-16-(p-fluorophenoxy)-18,19,20-trinor |
| F-19 | 1 | 1 | m-chloro | methyl | methyl | methyl | α | 15-epi-15,16-dimethyl-16-(m-chlorophenoxy)-18,19,20-trinor |
| F-20 | 1 | 1 | m-trifluoromethyl | methyl | methyl | methyl | α | 15-epi-15,16-dimethyl-16-(m-trifluoromethylphenoxy)-18,19,20-trinor |
| F-21 | 1 | 0 | | methyl | methyl | hydrogen | β | 16-methyl-16-phenoxy-18,19,20-trinor |
| F-22 | 1 | 1 | p-fluoro | methyl | methyl | hydrogen | β | 16-methyl-16-(p-fluorophenoxy)- |

Table F-continued

| | | | | | | | | |
|---|---|---|---|---|---|---|---|---|
| | | | | | | | | 18,19,20-trinor |
| F-23 | 1 | 1 | m-chloro | methyl | methyl | hydrogen | β | 16-methyl-16-(m-chlorophenoxy)-18,19,20-trinor |
| F-24 | 1 | 1 | m-trifluoro-methyl | methyl | methyl | hydrogen | β | 16-methyl-16-(m-trifluoromethyl-phenoxy)-18,19,20-trinor |
| F-25 | 3 | 0 | | hydrogen | hydrogen | hydrogen | α | 15-epi-2a,2b-dihomo-16-phenoxy-17,18,19,20-tetranor |
| F-26 | 3 | 1 | p-fluoro | hydrogen | hydrogen | hydrogen | α | 15-epi-2a,2b,-dihomo-16-(p-fluoro-phenoxy)-17,18,19,20-tetranor |
| F-27 | 3 | 1 | m-chloro | hydrogen | hydrogen | hydrogen | α | 15-epi-2a,2b-dihomo-16-(m-chloro-phenoxy)-17,18,19,20-tetranor |
| F-28 | 3 | 1 | m-trifluoro-methyl | hydrogen | hydrogen | hydrogen | α | 15-epi-2a,2b,-dihomo-16-(m-trifluoro-methylphenoxy)-17,18,19,20-tetranor |
| F-29 | 3 | 0 | | hydrogen | hydrogen | methyl | α | 15-epi-2a,2b-dihomo-15-methyl-16-phenoxy-17,18,19,20-tetranor |
| F-30 | 3 | 1 | p-fluoro | hydrogen | hydrogen | methyl | α | 15-epi-2a,2b-dihomo-15-methyl-16-(p-fluorophenoxy)-18,19,20-tetranor |
| F-31 | 3 | 1 | m-chloro | hydrogen | hydrogen | methyl | α | 15-epi-2a,2b-dihomo-15-methyl-16-(m-chlorophenoxy)-17,18,19,20-tetranor |
| F-32 | 3 | 1 | m-trifluoro-methyl | hydrogen | hydrogen | methyl | α | 15-epi-2a,2b-dihomo-15-methyl-16-(m-trifluoromethylphenoxy)-17,18,19,20-tetranor |

TABLE G

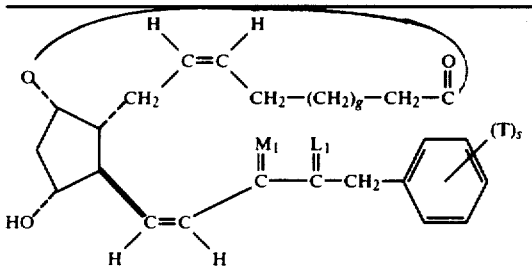

18,19,20-trinor-cis-13-PGF$_{2\alpha}$-type, 1,9-lactones

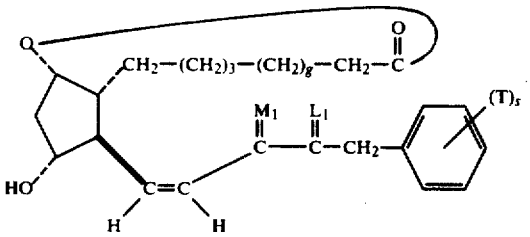

18,19,20-trinor-cis-13-PGF$_{1\alpha}$-type, 1,9-lactones

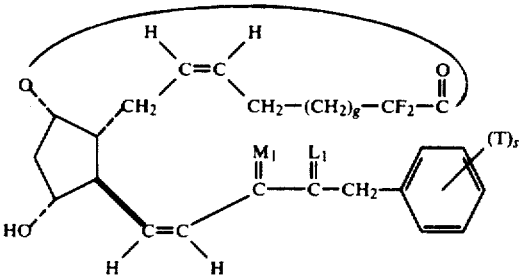

18,19,20-trinor-2,2-difluoro-cis-13-PGF$_{2\alpha}$-type, 1,9-lactones

TABLE G-continued
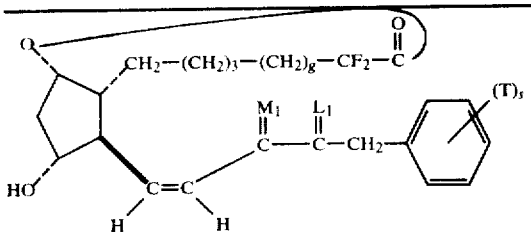
18,19,20-trinor-2,2-difluoro-cis-13-PGF$_{1\alpha}$-type, 1,9-lactones
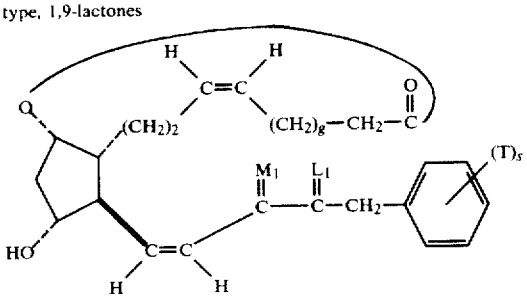
18,19,20-trinor-cis-4,5-didehydro-cis-13-PGF$_{1\alpha}$-type, 1,9-lactones
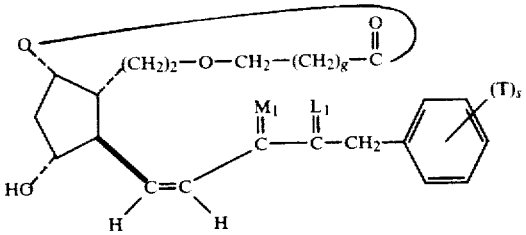
18,19,20-trinor-5-oxa-cis-13-PGF$_{1\alpha}$-type, 1,9-lactones
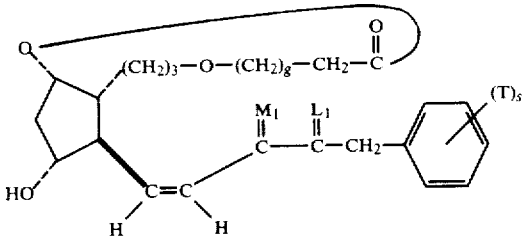
18,19,20-trinor-4-oxa-cis-PGF$_{1\alpha}$-type, 1,9-lactones
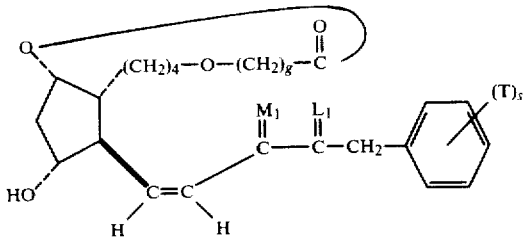

TABLE G-continued 18,19,20-trinor-3-oxa-cis-13-PGF$_{1\alpha}$-type, 1,9-lactones

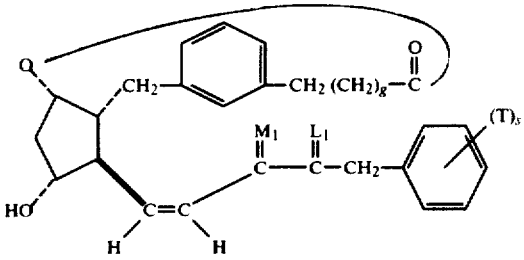

3,7-inter-m-phenylene-4,5,6,18,19,20-hexanor-cis-13-PGF$_{1\alpha}$-type, 1,9-lactones

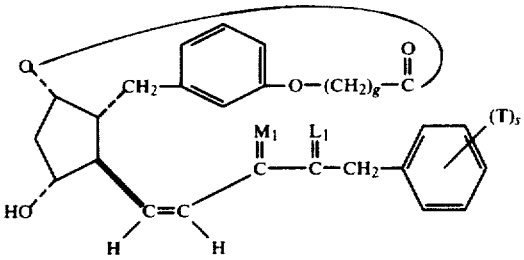

3,7-inter-m-phenylene-3-oxa-4,5,6,18,19,20-hexanor-cis-13-PGF$_{1\alpha}$-type, 1,9-lactones

| | | | | $L_1$ | | $M_1$ | | |
|---|---|---|---|---|---|---|---|---|
| Example | g | s | T | $R_3$ | $R_4$ | $R_5$ | ~OH | Name |
| G-1 | 1 | 0 | | hydrogen | hydrogen | hydrogen | α | 15-epi-17-phenyl |
| G-2 | 1 | 1 | p-fluoro | hydrogen | hydrogen | hydrogen | α | 15-epi-17-(p-fluorophenyl) |
| G-3 | 1 | 1 | m-chloro | hydrogen | hydrogen | hydrogen | α | 15-epi-17-(m-chlorophenyl) |
| G-4 | 1 | 1 | m-trifluoro-methyl | hydrogen | hydrogen | hydrogen | α | 15-epi-17-(m-trifluoromethylphenyl) |
| G-5 | 1 | 0 | | hydrogen | hydrogen | methyl | α | 15-epi-15-methyl-17-phenyl |
| G-6 | 1 | 1 | p-fluoro | hydrogen | hydrogen | methyl | α | 15-epi-15-methyl-17-(p-fluorophenyl) |
| G-7 | 1 | 1 | m-chloro | hydrogen | hydrogen | methyl | α | 15-epi-15-methyl-17-(m-chlorophenyl) |
| G-8 | 1 | 1 | m-trifluoro-methyl | hydrogen | hydrogen | methyl | α | 15-epi-15-methyl-17-(m-trifluoro-methylphenyl) |
| G-9 | 1 | 0 | | hydrogen | hydrogen | hydrogen | β | 17-phenyl |
| G-10 | 1 | 1 | p-fluoro | hydrogen | hydrogen | hydrogen | β | 17-(p-fluorophenyl) |
| G-11 | 1 | 1 | m-chloro | hydrogen | hydrogen | hydrogen | β | 17-(m-chlorophenyl) |
| G-12 | 1 | 1 | m-trifluoro-methyl | hydrogen | hydrogen | hydrogen | β | 17-(m-trifluoromethylphenyl) |
| G-13 | 1 | 0 | | methyl | methyl | hydrogen | α | 15-epi-16,16-dimethyl-17-phenyl |
| G-14 | 1 | 1 | p-fluoro | methyl | methyl | hydrogen | α | 15-epi-16,16-dimethyl-17-(p-fluoro-phenyl) |
| G-15 | 1 | 1 | m-chloro | methyl | methyl | hydrogen | α | 15-epi-16,16-dimethyl-17-(m-chloro-phenyl) |
| G-16 | 1 | 1 | m-trifluoro-methyl | methyl | methyl | hydrogen | α | 15-epi-16,16-dimethyl-17-(m-tri-fluoromethylphenyl) |
| G-17 | 1 | 0 | | methyl | methyl | methyl | α | 15-epi-15,16-trimethyl-17-phenyl |
| G-18 | 1 | 1 | p-fluoro | methyl | methyl | methyl | α | 15-epi-15,16,16-trimethyl-17-(p-fluorophenyl) |
| G-19 | 1 | 1 | m-chloro | methyl | methyl | methyl | α | 15-epi-15,16,16-trimethyl-17-(m-chlorophenyl) |
| G-20 | 1 | 1 | m-trifluoro-methyl | methyl | methyl | methyl | α | 15-epi-15,16,16-trimethyl-(m-tri-fluoromethylphenyl) |
| G-21 | 1 | 0 | | methyl | methyl | hydrogen | β | 16,16-dimethyl-17-phenyl |
| G-22 | 1 | 1 | p-fluoro | methyl | methyl | hydrogen | β | 16,16-dimethyl-17-(p-fluorophenyl) |
| G-23 | 1 | 1 | m-chloro | methyl | methyl | hydrogen | β | 16,16-dimethyl-17-(m-chlorophenyl) |
| G-24 | 1 | 1 | m-trifluoro-methyl | methyl | methyl | hydrogen | β | 16,16-dimethyl-17-(m-trifluoro-methylphenyl) |
| G-25 | 3 | 0 | | hydrogen | hydrogen | hydrogen | α | 15-epi-2a,2b,-dihomo-17-phenyl |
| G-26 | 3 | 1 | p-fluoro | hydrogen | hydrogen | hydrogen | α | 15-epi-2a,2b,-dihomo-17-(p-fluoro-phenyl) |
| G-27 | 3 | 1 | m-chloro | hydrogen | hydrogen | hydrogen | α | 15-epi-2a,2b,-dihomo-17-(m-chloro-phenyl) |
| G-28 | 3 | 1 | m-trifluoro- | hydrogen | hydrogen | hydrogen | α | 15-epi-2a,2b,-dihomo-17-(m-tri- |

TABLE G-continued

| | | | | | | | | |
|---|---|---|---|---|---|---|---|---|
| | | | methyl | | | | | fluoromethylphenyl) |
| G-29 | 3 | 0 | | hydrogen | hydrogen | methyl | α | 15-epi-2a,2b-dihomo-15-methyl-17-phenyl |
| G-30 | 3 | 1 | p-fluoro | hydrogen | hydrogen | methyl | α | 15-epi-2a,2b-dihomo-15-methyl-17-(p-fluorophenyl) |
| G-31 | 3 | 1 | m-chloro | hydrogen | hydrogen | methyl | α | 15-epi-2a,2b-dihomo-15-methyl-17-(m-chlorophenyl) |
| G-32 | 3 | 1 | m-trifluoro-methyl | hydrogen | hydrogen | methyl | α | 15-epi-2a,2b-dihomo-15-methyl-17-(m-trifluoromethylphenyl) |
| G-33 | 1 | 0 | | fluoro | fluoro | hydrogen | α | 15-epi-16,16-difluoro-17-phenyl |
| G-34 | 1 | 1 | p-fluoro | fluoro | fluoro | hydrogen | α | 15-epi-16,16-difluoro-17-(p-fluoro-phenyl) |
| G-35 | 1 | 1 | m-chloro | fluoro | fluoro | hydrogen | α | 15-epi-16,16-difluoro-17-(m-chloro-phenyl) |
| G-36 | 1 | 1 | m-trifluoro-methyl | flouro | fluoro | hydrogen | α | 15-epi-16,16-diflouro-17-(m-tri-fluoromethylphenyl) |
| G-37 | 1 | 0 | | fluoro | fluoro | methyl | α | 15-epi-15-methyl-16,16-difluoro-17-phenyl |
| G-38 | 1 | 1 | p-fluoro | fluoro | fluoro | methyl | α | 15-epi-15-methyl-16,16-difluoro-17-(p-fluorophenyl) |
| G-39 | 1 | 1 | m-chloro | fluoro | fluoro | methyl | α | 15-epi-15-methyl-16,16-difluoro-17-(m-chlorophenyl) |
| G-40 | 1 | 1 | m-trifluoro-methyl | fluoro | fluoro | methyl | α | 15-epi-15-methyl-16,16-difluoro-17-(m-trifluoromethylphenyl) |
| G-41 | 1 | 0 | | fluoro | fluoro | hydrogen | β | 16,16-difluoro-17-phenyl |
| G-42 | 1 | 1 | p-fluoro | fluoro | fluoro | hydrogen | β | 16,16-difluoro-17-(p-fluorophenyl) |
| G-43 | 1 | 1 | m-chloro | fluoro | fluoro | hydrogen | β | 16,16-difluoro-17-(m-chlorophenyl) |
| G-44 | 1 | 1 | m-trifluoro-methyl | fluoro | fluoro | hydrogen | β | 16,16-difluoro-17-(m-fluoromethyl-phenyl) |

Table H

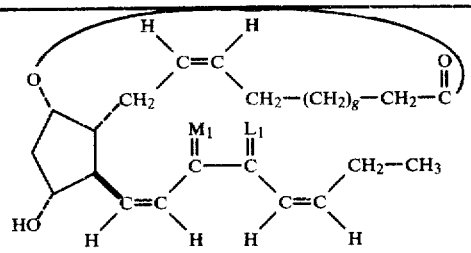

cis-13-PGF$_{3\alpha}$-type, 1,9-lactones

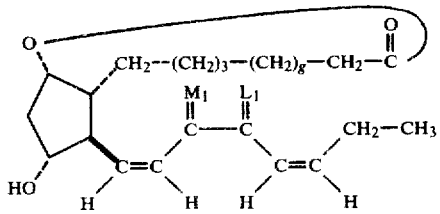

cis-13-5,6-dihydro-PGF$_{3\alpha}$-type, 1,9-lactones

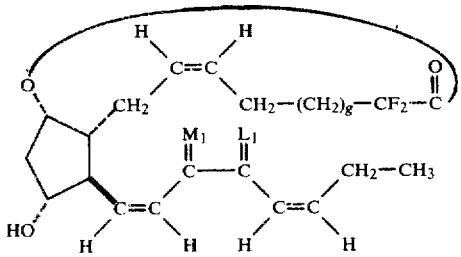

2,2-difluoro-cis-13-PGF$_{3\alpha}$-type, 1,9-lactones

Table H-continued
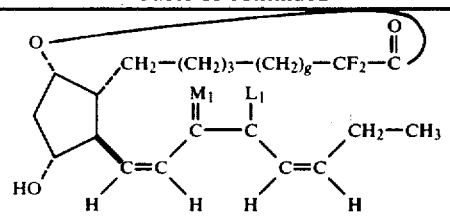
2,2-difluoro-cis-13-5,6-dihydro-PGF$_{3\alpha}$-type, 1,9-lactones
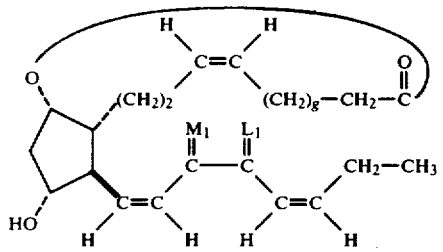
cis,cis-4,5,17,18-tetradehydro-cis-13-PGF$_{1\alpha}$-type, 1,9-lactones
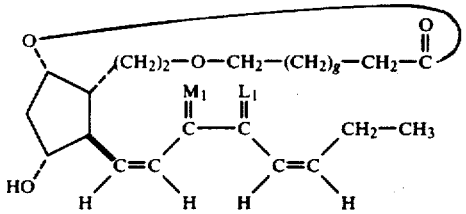
5-oxa-cis-13-cis-17,18-didehydro-PGF$_{1\alpha}$-type, 1,9-lactones
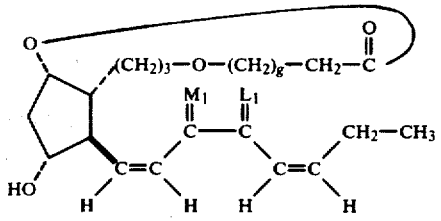
4-oxa-cis-13-cis-17,18-didehydro-PGF$_{1\alpha}$-type 1,9-lactones
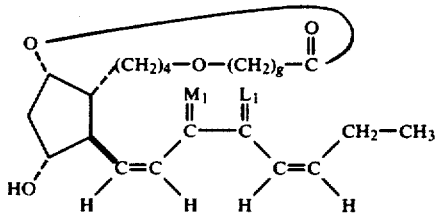
3-oxa-cis-13-cis-17,18-didehydro-PGF$_{1\alpha}$-type, 1,9-lactones
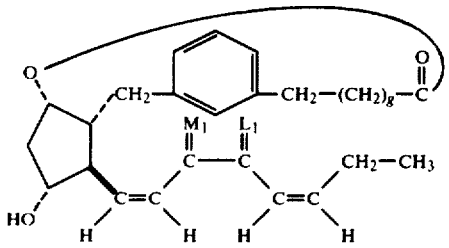
3,7-inter-m-phenylene-4,5,6-trinor-cis-13-cis- Table H-continued 17,18-didehydro-PGF$_{1\alpha}$-type, 1,9-lactones

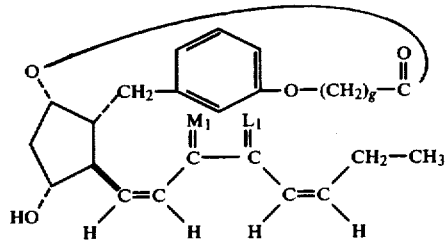

3,7-inter-m-phenylene-3-oxa-4,5,6-trinor-cis-13-cis-17,18-didehydro-PGF$_{1\alpha}$-type, 1,9-lactones

| Example | g | $R_3$ | $L_1$ $R_4$ | $R_5$ | ~OH | Name |
|---|---|---|---|---|---|---|
| H-1 | 1 | methyl | hydrogen | hydrogen | α | 15-epi-16-methyl |
| H-2 | 1 | methyl | hydrogen | methyl | β | 15,16-dimethyl |
| H-3 | 1 | methyl | hydrogen | hydrogen | β | 16-methyl |
| H-4 | 1 | methyl | methyl | hydrogen | α | 15-epi-16,16-dimethyl |
| H-5 | 1 | methyl | methyl | methyl | α | 15-epi-15,16,16-trimethyl |
| H-6 | 1 | methyl | methyl | hydrogen | β | 16,16-dimethyl |
| H-7 | 1 | fluoro | hydrogen | hydrogen | α | 15-epi-16-fluoro |
| H-8 | 1 | fluoro | hydrogen | methyl | α | 15-epi-15-methyl-16-fluoro |
| H-9 | 1 | fluoro | hydrogen | hydrogen | β | 16-fluoro |
| H-10 | 1 | fluoro | fluoro | hydrogen | α | 15-epi-16,16-difluoro |
| H-11 | 1 | fluoro | fluoro | methyl | α | 15-epi-15-methyl-16,16-difluoro |
| H-12 | 1 | fluoro | fluoro | hydrogen | β | 16,16-difluoro |
| H-13 | 1 | hydrogen | hydrogen | hydrogen | α | 15-epi |
| H-14 | 1 | hydrogen | hydrogen | methyl | α | 15-epi-15-methyl |
| H-15 | 3 | hydrogen | hydrogen | hydrogen | α | 15-epi-2a,2b-dihomo |
| H-16 | 3 | hydrogen | hydrogen | methyl | α | 15-epi-2a,2b-dihomo-15-methyl |
| H-17 | 3 | methyl | methyl | hydrogen | α | 15-epi-2a,2b-dihomo-16,16-dimethyl |
| H-18 | 3 | methyl | methyl | methyl | α | 15-epi-2a,2b-dihomo-15,16,16-trimethyl |
| H-19 | 3 | fluoro | fluoro | hydrogen | α | 15-epi-2a,2b-dihomo-16,16-difluoro |
| H-20 | 3 | fluoro | fluoro | methyl | α | 15-epi-2a,2b-dihomo-15-methyl-16,16-difluoro |

APPENDIX

This appendix describes the preparation of the various prostaglandin analogs of formula 1.

With respect to Charts S and T herein, the symbols have the same definition herein as in Charts A–R, except that the following additional sysbols are employed:

$Y_5$ is trans—CH=CH—, cis—CH=CH—, —$CH_2CH_2$—, or —CH=CH—(Hal), wherein Hal bromo or chloro.

$R_{16}$ is hydrogen or —$OR_9$, wherein $R_9$ is an acyl protecting group.

$R_{18}$ is hydrogen or —$OR_{10}$, wherein $R_{10}$ is a blocking group.

$R_{26}$ is alkyl, cycloalkyl, aralkyl, phenyl, or phenyl substituted with halogen or alkyl. $M_5$ is

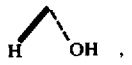

Chart S

-continued

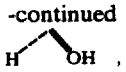

or a mixture of

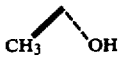

and

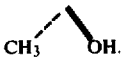

$M_6$ is

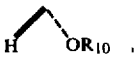

-continued
CCI
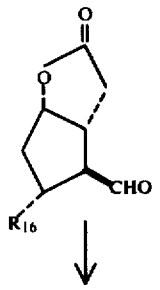
CCII
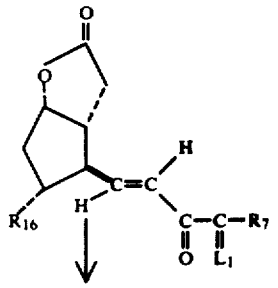
CCIII
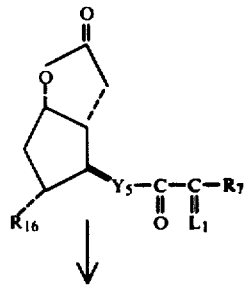
CCIV
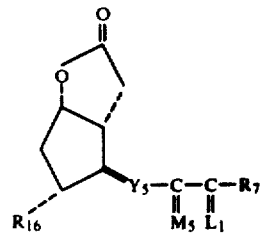
CCV
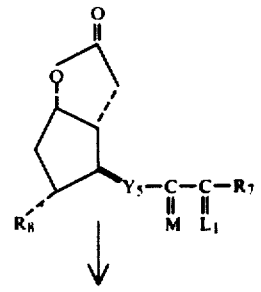

-continued
CCVI
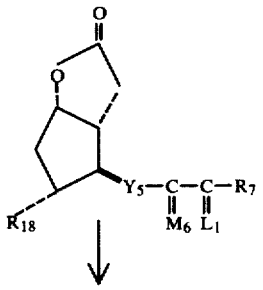
CCVII
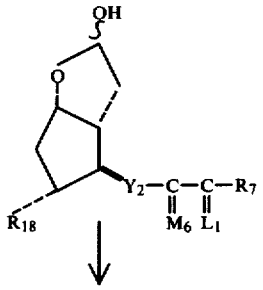
CCVIII
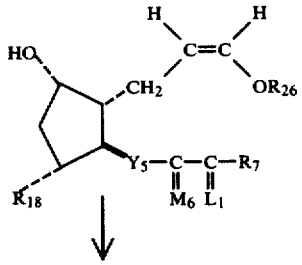
CCIX
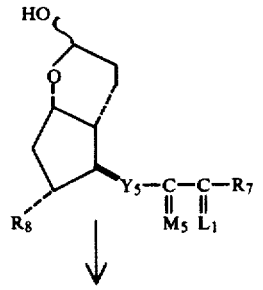
CCX
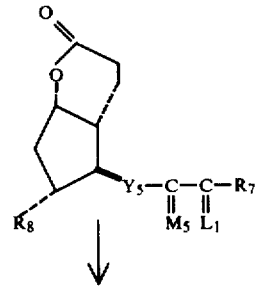

-continued
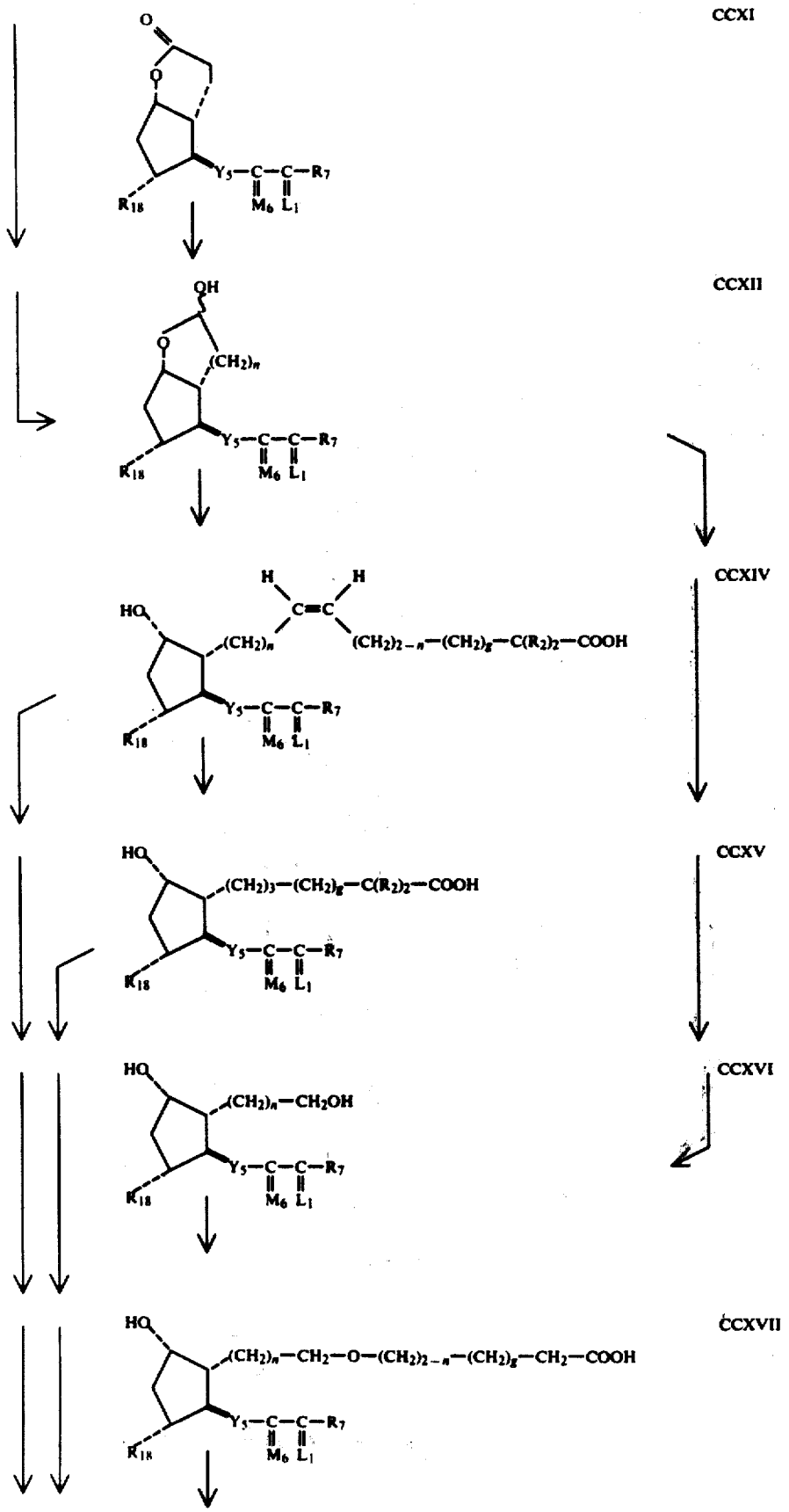

-continued
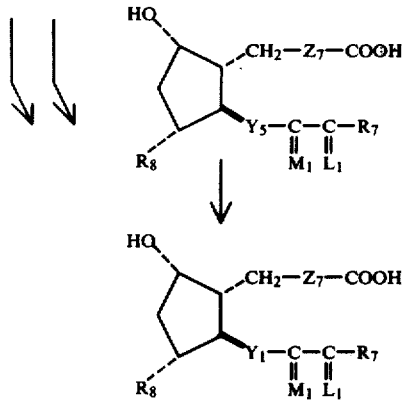
CCXVIII
CCIX
Chart T
CCXXI
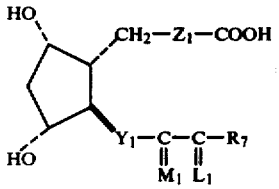
CCXXII
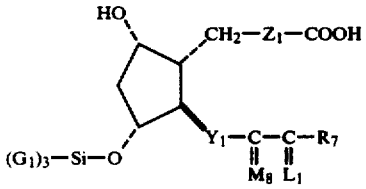
CCXXIII
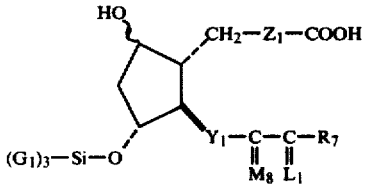
CCXXIV
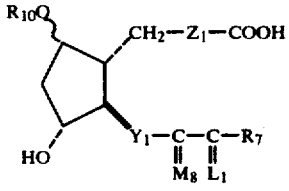
CCXXV
Chart T-continued
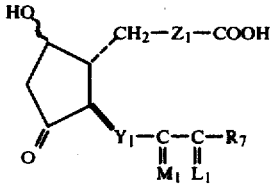
CCXXVI
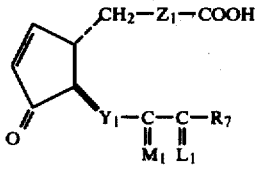
CCXXVII
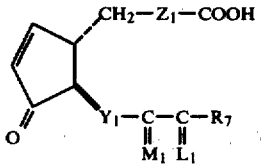
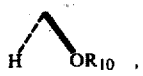
or a mixture of
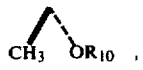
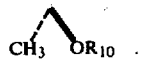
$Z_7$ is the same as $Z_1$, except that $Z_7$ does not include

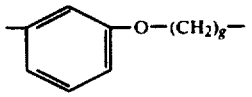

or

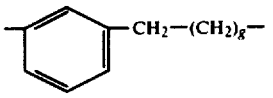

The integer n is one or 2.

Chart S provides a method whereby the formula CCI compound is transformed to the formula CCXIX compound. The formula CCI starting material is known in the art. For compounds wherein $R_{16}$ is —$OR_9$, see Netherlands Pat. No. 7,305,817, (Derwent Farmdoc CPI No. 69717U). For those compounds wherein $R_{16}$ is hydrogen see Netherlands Pat. No. 7,309,856, (Dewent Farmdoc CPI No. 10095V). The transformation of the formula CCI compound to the formula CCII compound proceeds by methods known in the art. For example, formula CCII compounds wherein $L_1$ includes fluoro substitution are described at Netherlands Pat. No. 7,305,817, (Derwent Farmdoc CPI No. 69717U); compounds wherein $L_1$ includes methyl substitution are described in U.S. Pat. No. 3,903,131; compounds wherein $R_7$ includes phenyl substituted compounds are described in Belgian Pat. No. 804,873 (Derwent Farmdoc CPI No. 22865V); and compounds wherein $R_7$ includes phenoxy substitution are described in Netherlands Pat. No. 7,306,462 (Derwent Farmdoc CPI No. 732,79U). The formula CCIII compound is prepared from the formula CCII compound by manipulation of the C-13 C-14 double bond. For example, this bond is hydrogenated by employing catatlyic methods employing (e.g. palladium-on-charcoal) under a hydrogen atmosphere. Further, the formula CCIII cis-13 compound is prepared from the formula CCII trans-13 compound by photoisomerization. For this purpose techniques generally known in the art are employed. For example, the formula CCII compound is exposed to radiation of about 3500 Angstroms until a equilibrium mixture of trans and cis isomers capable of chromatographic separation is obtained. Finally, when a formula CCIII 14-halo compound is to be prepared, the formula CCII compound is dihalogenated, thereby preparing its 13,14-dihalo derivative, followed by dehydrohalogenation with base. Again, methods generally known in the art for preparing such vicinal dihalides (e.g. reaction with the molecular halogen) and dehydrohalogenation are employed. Thereafter, the reaction sequence which transforms the formula CCIII compound to the formula CCVII compound is known in the art. See, for example, Belgian Pat. No. 817,846, (Derwent Farmdoc CPI No. 09124W) and Netherlands Pat. No. 7,305,817, (Derwent Farmdoc CPI No. 69717U).

The reaction sequence of Chart S wherein the formula CCVII compound is transformed to the formula CCIX compound is likewise known in the art. See, Netherlands Pat. No. 7,305,434, (Derwent Farmdoc CPI No. 69665U).

The formula CCX compound is then prepared from the formula CCIX compound by oxidation of the formula CCIX lactol to a lactone. This transformation is carried out using for example silver oxide as an oxidizing agent followed by treatment with pyridine hydrochloride. The formula CCX lactone is then converted to the formula CCXI ether by transformation of any free hydroxy moieties to blocking groups according to $R_{10}$, following the procedures hereinabove described for such transformations. Thereafter, the formula CCXII compound, (wherein $n$ is 2) is prepared from the formula CCXI compound by reduction of the lactone to a lactol as in the transformation of the formula CCVI compound to the formula CCVII compound. This formula CCXII lactol is then transformed successively to the formula CCXIV and formula CCXV compound by methods again known in the art and described in Netherlands Pat. No. 7,305,817, (Derwent Farmdoc CPI No. 698717U). Alternatively, the formula CCXII compound is transformed to the formula CCXVI compound and thereafter the formula CXXVII compound by methods described in U.S. Pat. No. 3,864,387. Thereafter, the formula CCXVIII compound is prepared by hydrolysis of any blocking groups according to $R_{10}$, as described in previous charts.

Finally, the formula CXVIII compound is transformed to the corresponding formula CCXIX compound when $Y_5$ is —CH=C(Hal)— by dehydrohalogenation. Procedures generally known in the art are employed.

Following the procedure of Chart S and $PGF_\alpha$-or 11-deoxy-$PGF_\alpha$-type products therein, or their $R_{10}$-containing precursors therein are transformed to corresponding PGE or 11-deoxy-PGE, $PGF_\beta$, or 11-deoxy-$PGF_\beta$, PGA, or PGB-type compounds following the procedures described in Netherlands Pat. No. 7,305,817, (Derwent Farmdoc CPI No 69717U).

In preparing 8β,12α-isomers of products described in the preceding paragraph or in Chart S, the procedures of Chart S in the preceding paragraph are employed, except that in place of the formula CCI bicyclic lactone aldehyde there is employed the following compound:

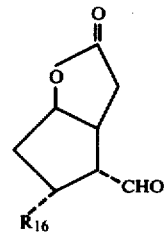

This epimeric bicyclic lactone aldehyde is described in Belgian Pat. No. 804,873, (Derwent Farmdoc CPI No. 22865V), and Netherlands Pat. No. 7,309,856 (Derwent Farmdoc CPI No. 10095V). Accordingly, the 8β,12α-$PGF_\beta$ or 11-deoxy-$PGF_\beta$-type product corresponding to formula CCIX is prepared. By the method referenced in the preceding paragraph this compound is likewise transformed to the corresponding PGE- or 11-deoxy-PGE-type compound, $PGF_\alpha$ or 11-deoxy-$PGF_{60}$ -type compound, PGA-type compound, or, PGB-type compound. Alternatively, the various 8β,12α-PG-type compounds of formula I are prepared from ent PGA-type compounds. In this case, for example, the enantiomer of the formula CCI compound is employed in the preparation of an ent PGA-type compound, which is then epoxidized and reduced to the corresponding (11RS)-8β,12α-PGE-type compound. Methods for this transformation, and the successive transformations of (11RS)-8β,12α-PGE-type compound are described in Belgian Pat. No. 804,873 (Derwent Farmdoc CPI No. 22865V).

Further PGA-type compound or ent-PGA-type compounds are transformed to 11-deoxy-PGE-, 11-deoxy-$PGF_{\alpha}$-, or 11-deoxy-$PGF_{\beta}$-type compounds by a borohydride cyclopentane ring reduction or catalytic ring reduction by the procedure described in Netherlands Pat. No. 7,309,856, (Derwent Farmdoc CPI No. 10095V).

Prostaglandin analogs of formula I with interphenylene-or interphenylene-oxa-containing side chains are prepared by methods known in the art and described in U.S. Pat. No. 3,928,418. For example, Charts L and M therein describe methods whereby interphenylene oxa compounds are conveniently prepared from readily available starting materials. For preparing interphenylene-containing prostaglandin analogs, i.e. those wherein $Z_1$ is

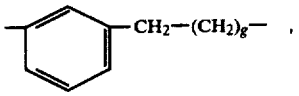

then, the procedure of Chart M of U.S. Pat. No. 3,928,418 is employed except that in step (a) of this Chart an aldehyde of the formula

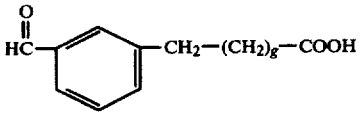

is employed in place of the specified starting material therein.

For the 16-phenoxy interphenylene containing compounds, the preferred method of their preparation proceeds by ozonolysis of the trans-13 double bond of the final $PGF_{\alpha}$ final product to a corresponding 13,14,15,16,17,18,19,20-octanor-13-carboxaldehyde $PGF_{\alpha}$-type product. This aldehyde is then transformed to the 16-phenoxy-3,7-inter-m-phenylene-or 3,7-inter-m-phenylene-3-oxa-16-phenoxy-$PGF_{\alpha}$-type compound by the procedure of chart S (e.g. the transformation affecting the 2β-side chain of the formula CI aldehyde therein).

When interphenylene or interphenylene oxa-containing prostaglandin analogs of formula I are to be prepared wherein $Y_1$ is $—CH_2CH_2—$, catalytic hydrogenation methods of the corresponding trans-13 compound are employed, as described above. When interphenylene or interphenyleneoxa-containing prostaglandin analogs wherein $Y_1$ is cis—CH=CH— or —C≡C are to be prepared, then the preparation first proceeds by oxidation of the 15-hydroxy (of compounds wherein $R_5$ is hydrogen) to a corresponding 15-oxo using reagents known in the art to selectively effect this reduction. For example, 2,3-dichloro-5,6-dicyanobenzoquinone is employed. Thereupon, the transformation of the α,β-unsaturated ketones so formed proceeds as in the transformation of the formula CCII compound to the formula CCIII compound. Thereafter, when the 13-acetylenic moiety is to be introduced, dehydrohalogenation with base is employed. Having prepared each of the various $PGF_{\alpha}$-type interphenylene or interphenylene oxa-containing analogs, transformation to the corresponding PGE-, $PGF_{\beta}$-, PGA-, PGB, 11-deoxy-$PGF_{\alpha}$-, or 11-deoxy-$PGF_{\beta}$-type compounds proceeds by methods described following Chart S. Further, when 8β,12α-type compounds are to be prepared the ent $PGF_{\alpha}$-type compound corresponding to Charts L and M are employed, being transformed to the corresponding ent-PGA-type compound which is thereafter transformed to the various 8β,12α-isomers of the various ring structures described above.

Chart T provides a method whereby the various $PGF_{\alpha}$-type compounds described in and following Chart S are transformed to the various PG-type compounds with 11-oxo-containing cyclopentane ring structures (formulas CCXXV, CCXXVI, and CCXXVII).

With respect to Chart T the transformations therein are all generally described in succeeding Charts. For example, the transformation of the formula CCXXI compound to the formula CCXXII compound is accomplished by the selective blocking described in the transformation of the formula XXXI compound to the formula XXXIV compound of Chart B, followed by the selective silylation described in the transformation of the formula XLI compound to the formula XLII compound of Chart C.

Thereafter, the optional epimerization of the formula CCXXII compound to the formula CCXXIII compound proceeds as is described in the transformation of the formula CLXII compound to the formula CLXIII compound in Chart M. Finally, the C-9 blocking, and selective C-11 hydrolysis of the transformation of the formula CCXXIII compound to the formula CCXXIV compound is described in Chart C wherein the formula CXLII or formula CXLIV compound is transformed to the formula CXLVI compound. Finally, the oxidation of the formula CCXXIV compound to the formula CCXXV compound is described in the transformation of Chart C of the formula XLVII compound to the formula LI compound, and thereafter the formula LII compound.

With respect to the transformation to the formula CCXXV compound to the formula CCXXVI compound the method employed in Chart F and the transformation of the formula XCIII compound to the formula XCIV compound is employed.

Finally, the transformation of the formula CCXXVI compound to the formula CCXXVII compound is achieved by methods described following Chart S for the transformation of PGA-type compounds corresponding 11-deoxy-PGE-type compounds.

I claim:

[1. A prostaglandin-type, 1,9-lactone of the formula

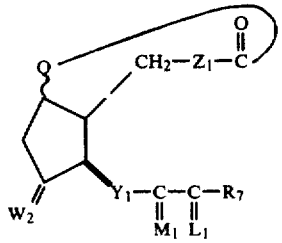

or

-continued

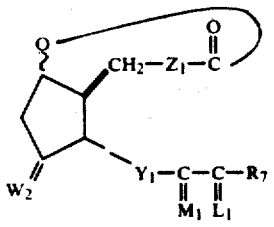

wherein $W_2$ is

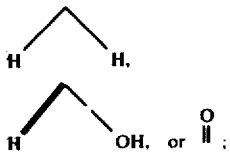

wherein $L_1$ is

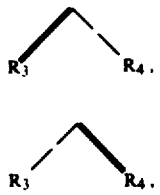

or a mixture of

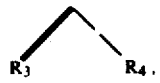

and

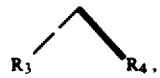

wherein $R_3$ and $R_4$ are hydrogen, methyl, or fluoro, being the same or different, with the proviso that one of $R_3$ and $R_4$ is fluoro, only when the other is hydrogen or fluoro;

wherein $M_1$ is

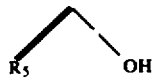

or

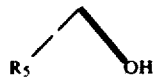

wherein $R_5$ is hydrogen or methyl;

wherein $R_7$ is $-(CH_2)_m-CH_3$, wherein m is one to 5, inclusive, cis—CH=CH—$CH_2$—$CH_3$, or

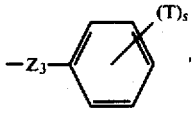

wherein T is chloro, fluoro, trifluoromethyl, alkyl of one to 3 carbon atoms, inclusive, or alkoxy of one to 3 carbon atoms, inclusive, the various T's being the same or different, s is zero, one, 2, or 3, and $Z_3$ is oxa or methylene, with the provisio that not more than two T's are other than alkyl, and the further proviso that $Z_3$ is oxa only when $R_3$ and $4_4$ are hydrogen or methyl, being the same or different;

wherein $Y_1$ is trans—CH=CH—, —$CH_2CH_2$—, cis—CH=CH—, or —C≡C—; and wherein $Z_1$ is cis—CH=CH—$CH_2$—$(CH_2)_g$—$CH_2$—, (1)

cis—CH=CH—$CH_2$—$(CH_2)_g$—$CF_2$—, (2)

cis—$CH_2$—CH=CH—$(CH_2)_g$—$CH_2$—, (3)

—$(CH_2)_3$—$(CH_2)_g$—$CH_2$—, (4)

—$(CH_2)_3$—$(CH_2)_g$—$CF_2$—, (5)

—$CH_2$—O—$CH_2$—$(CH_2)_g$—$CH_2$—, (6)

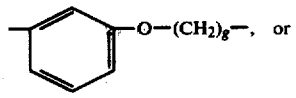

(7)

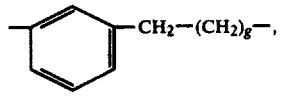

(8)

wherein g is one to 3, inclusive.]

[2. A compound according to claim 1, wherein $W_2$ is

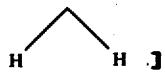

.]

[3. 11-Deoxy-$PGF_{2\alpha}$, 1,9-lactone, a compound according to claim 2.]

[4. A compound according to claim 1, wherein $W_2$ is

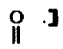

.]

[5. A compound according to claim 4, wherein $Y_1$ is —C≡C—.]

[6. 13,14-Didehydro-$PGD_2$, 1,9-lactone, a compound according to claim 5.]

[7. A compound according to claim 4, wherein $Y_1$ is cis—CH=CH—.]

[8. cis-13-$PGD_2$, 1,9-lactone.]

[9. A compound according to claim 4, wherein $Y_1$ is —$CH_2CH_2$—.]

[10. 13,14-Dihydro-$PGD_2$, 1,9-lactone, a compound according to claim 9.]

[11. A compound according to claim 4, wherein $Y_1$ is trans—CH=CH—.]

[12. $PGD_2$, 1,9-lactone, a compound according to claim 11.]

[13. A compound according to claim 1, wherein $W_2$ is

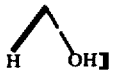

[14. A compound according to claim 13, wherein ~ is α.]

[15. A compound according to claim 14, wherein $M_1$

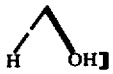

[16. 15-epi-$PGF_{2\alpha}$, 1,9-lactone, a compound according to 15.]

[17. A compound according to claim 14, wherein $M_1$ is

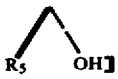

[18. A compound according to claim 17, wherein $Z_1$ is $—CH_2—O—CH_2—(CH_2)_g—CH_2—$.]

[19. 5-oxa-$PGF_{1\alpha}$, 1,9-lactone, a compound according to claim 18.]

[20. A compound according to claim 17, wherein $Z_1$ is

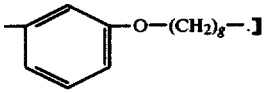

[21. 3-oxa-3,7-inter-m-phenylene-4,5,6-trinor-$PGF_{1\alpha}$, 1,9-lactone, a compound according to claim 20.]

[22. A compound according to claim 17, wherein $Z_1$ is

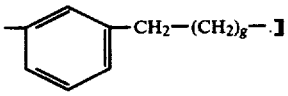

[23. 3,7-inter-m-phenylene-4,5,6-trinor-$PGF_{1\alpha}$, 1,9-lactone, a compound according to claim 22.]

[24. A compound according to claim 17, wherein $Z_1$ is cis—$CH_2$—CH=CH—$(CH_2)_g$—$CH_2$—.]

[25. cis-4,5-Didehydro-$PGF_{1\alpha}$, 1,9-lactone, a compound according to claim 24.]

[26. A compound according to claim 17, wherein $Z_1$ is cis—CH=CH—$CH_2$—$(CH_2)_g$—$CF_2$—.]

[27. 2,2,16,16-Tetrafluoro-$PGF_{2\alpha}$, 1,9-lactone, a compound according to claim 26.]

[28. 2,2-Difluoro-16,16-dimethyl-$PGF_{2\alpha}$,1,9-lactone, a compound according to claim 26.]

[29. 2,2-Difluoro-15-methyl-$PGF_{2\alpha}$, 1,9-lactones, a compound according to claim 26.]

[30. 2,2-Difluoro-$PGF_{2\alpha}$, 1,9-lactone, a compound according to claim 26.]

[31. A compound according to claim 17, wherein $Z_1$ is $—(CH_2)_3—(CH_2)_g—CF_2—$.]

[32. 2,2,16,16-Tetrafluoro-$PGF_{1\alpha}$, 1,9-lactone, a compound according to claim 31.]

[33. 2,2-Difluoro-16,16-dimethyl-$PGF_{1\alpha}$, 1,9-lactone, a compound according to claim 31.]

[34. 2,2-Difluoro-15-methyl-$PGF_{1\alpha}$, 1,9-lactone, a compound according to claim 31.]

[35. 2,2-Difluoro-$PGF_{1\alpha}$, 1,9-lactone, a compound according to claim 31.]

[36. A compound according to claim 17, wherein $Z_1$ is $—(CH_2)_3—(CH_2)_g—CH_2—$.]

[37. 16,16-Difluoro-$PGF_{1\alpha}$, 1,9-lactone, a compound according to claim 36.]

[38. 16,16-Dimethyl-$PGF_{1\alpha}$, 1,9-lactone, a compound according to claim 36.]

[39. 15-Methyl-$PGF_{1\alpha}$, 1,9-lactone, a compound according to claim 36.]

[40. $PGF_{1\alpha}$, 1,9-lactone, a compound according to claim 36.]

[41. A compound according to claim 17, wherein $Z_1$ is cis—CH=CH—$CH_2$—$(CH_2)_g$—$CH_2$—.]

[42. A compound according to claim 41, wherein *g* is 3.]

[43. A compound according to claim 41, wherein *g* is 1.]

[44. A compound according to claim 43, wherein $Y_1$ is —C≡C—.]

[45. 13,14-Didehydro-$PGF_{2\alpha}$, 1,9-lactone, a compound according to claim 44.]

[46. A compound according to claim 43, wherein $Y_1$ is cis—CH=CH—.]

[47. cis-13-$PGF_{2\alpha}$, 1,9-lactone, a compound according to claim 46.]

[48. A compound according to claim 43, wherein $Y_1$ is $—CH_2CH_2—$.]

[49. 13,14-dihydro $PGF_{2\alpha}$, 1,9-lactone, a compound according to claim 48.]

[50. A compound according to claim 43, wherein $Y_1$ is trans—CH=CH—.]

[51. A compound according to claim 50, wherein $R_7$ is cis—CH=CH—$CH_2$—$CH_3$—.]

[52. $PGF_{3\alpha}$, 1,9-lactone, a compound according to claim 51.]

[53. A compound according to claim 50, wherein 7 is

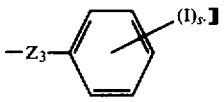

[54. A compound according to claim 53, wherein *s* is zero or one and T is chloro, fluoro, or trifluoromethyl.]

[55. A compound according to claim 54, wherein $Z_3$ is methylene.]

[56. A compound according to claim 55, wherein $R_5$ is methyl.]

[57. 15-Methyl-17-Phenyl-18,19,20-trinor-$PGF_{2\alpha}$, 1,9-lactone, a compound according to claim 56.]

[58. A compound according to claim 55, wherein $R_5$ is hydrogen.]

[59. A compound according to claim 58, wherein at least one of $R_3$ and $R_4$ are fluoro.]

[60. 16,16-Difluoro-17-Phenyl-18,19,20-trinor-$PGF_{2\alpha}$, 1,9-lactone, a compound according to claim 59.]

[61. A compound according to claim 58, wherein at least one of $R_3$ and $R_4$ is methyl.]

[62. 16,16-Dimethyl-17-phenyl-18,19,20-trinor-$PGF_{2\alpha}$, 1,9-lactone, a compound according to claim 61.]

[63. A compound according to claim 58, wherein $R_3$ and $R_4$ are both hydrogen.]

[64. 17-Phenyl-18,19,20-trinor-$PGF_{2\alpha}$, 1,9-lactone, a compound according to claim 63.]

[65. A compound according to claim 54, wherein $Z_3$ is oxa.]

[66. A compound according to claim 65, wherein $R_5$ is methyl.]

[67. 15-Methyl-16-Phenoxy-17,18,19,20-tetranor-$PGF_{2\alpha}$, 1,9-lactone, a compound according to claim 66.]

[68. A compound according to claim 65, wherein $R_5$ is hydrogen.]

[69. A compound according to claim 68, wherein at least one of $R_3$ and $R_4$ is methyl.]

[70. 16-Methyl-16-Phenoxy-18,19,20-trinor-$PGF_{2\alpha}$, 1,9-lactone, a compound according to claim 69.]

[71. A compound according to claim 68, wherein $R_3$ and $R_4$ are both hydrogen.]

[72. 16-Phenoxy-17,18,19,20-tetranor-$PGF_{2\alpha}$, 1,9-lactone, a compound according to claim 71.]

[73. A compound according to claim 50, wherein $R_7$, is $-(CH_2)_m-CH_3-$.]

[74. A compound according to claim 73, wherein m is 30.]

[75. A compound according to claim 74, wherein $R_5$ is methyl.]

[76. A compound according to claim 75, wherein at least one of $R_3$ and $R_4$ is fluoro.]

[77. 15-Methyl-16,16-difluoro-$PGF_{2\alpha}$, 1,9-lactone, a compound according to claim 76.]

[78. A compound according to claim 75, wherein at least one of $R_3$ and $R_4$ is methyl.]

[79. 15,16,16-Trimethyl-$PGF_{2\alpha}$, 1,9-lactone, a compound according to claim 78.]

[80. A compound according to claim 75, wherein $R_3$ and $R_4$ are both hydrogen.]

[81. 15-Methyl-$PGF_{2\alpha}$, 1,9-lactone, a compound according to claim 80.]

[82. A compound according to claim 74, wherein $R_5$ is hydrogen.]

[83. A compound according to claim 82, wherein at least one of $R_3$ and $R_4$ is fluoro.]

[84. A compound according to claim 83, wherein $R_3$ and $R_4$ are both fluoro.]

[85. 16,16-Difluoro-$PGF_{2\alpha}$, 1,9-lactone, a compound according to claim 84.]

[86. A compound according to claim 82, wherein at least one of $R_3$ and $R_4$ is methyl.]

[87. A compound according to claim 86, wherein $R_3$ and $R_4$ are both methyl.]

[88. 16,16-Dimethyl-$PGF_{2\alpha}$, 1,9-lactone, a compound according to claim 87.]

[89. A compound according to claim 82, wherein $R_3$ and $R_4$ are both hydrogen.]

[90. $PGF_{2\alpha}$, 1,9-lactone, a compound according to claim 89.]

*91. A prostaglandin-type, 1,9-lactone of the formula*

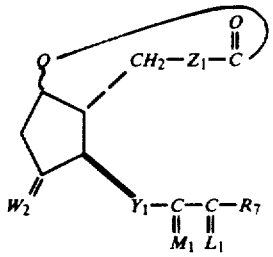

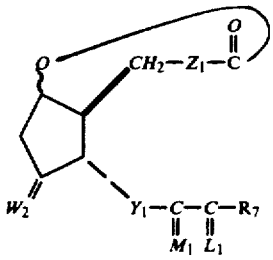

*wherein $W_2$ is*

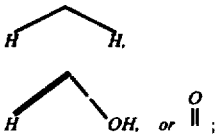

*wherein $L_1$ is*

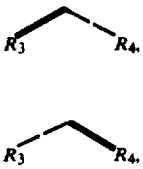

*or a mixture of*

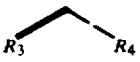

*and*

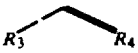

*wherein $R_3$ and $R_4$ are hydrogen, methyl, or fluoro, being the same or different, with the proviso that one of $R_3$ and $R_4$ is fluoro, only when the other is hydrogen or fluoro; wherein $M_1$ is*

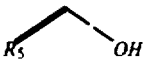

*or*

-continued

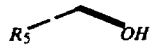

*wherein $R_5$ is hydrogen or methyl;*

*wherein $R_7$ is $-(CH_2)_m-CH_3$, wherein m is one to 5, inclusive, cis—CH=CH—$CH_2$—$CH_3$, or*

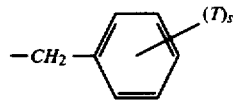

*wherein T is chloro, fluoro, trifluoromethyl, alkyl of one to 3 carbon atoms, inclusive, or alkoxy of one to 3 carbon atoms, inclusive, the various T's being the same or different, s is zero, one, 2, or 3, with the proviso that not more than two T's are other than alkyl;*

*wherein $Y_1$ is trans—CH=CH—, —$CH_2CH_2$—, cis—CH=CH—, or —C≡C—; and*

*wherein $Z_1$ is* cis—CH=CH—$CH_2$—$(CH_2)_g$—$CH_2$—, (1)

cis—CH=CH—$CH_2$—$(CH_2)_g$—$CF_2$—, (2)

cis—$CH_2$—CH=CH—$(CH_2)_g$—$CH_2$—, (3)

—$CH_2)_3$—$(CH_2)_g$—$CH_2$—, (4)

—$(CH_2)_3$—$(CH_2)_g$—$CF_2$—, (5)

—$CH_2$—O—$CH_2$—$(CH_2)_g$—$CH_2$—, (6)

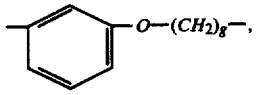

(7)

or

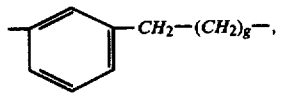

(8)

*wherein g is one to 3 inclusive.*

*92. A compound according to claim 91, wherein $W_2$ is*

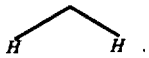

*93. 11-Deoxy-PGF$_2\alpha$, 1,9-lactone, a compound according to claim 92.*

*94. A compound according to claim 91, wherein $W_2$ is*

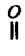

*95. A compound according to claim 94, wherein $Y_1$ is —C≡C—.*

*96. 13,14-Didehydro-PGD$_2$, 1,9-lactone, a compound according to claim 95.*

*97. A compound according to claim 94, wherein $Y_1$ is cis—CH=CH—.*

*98. cis-13-PGD$_2$, 1,9-lactone, a compound according to claim 97.*

*99. A compound according to claim 94, wherein $Y_1$ is —$CH_2CH_2$—.*

*100. 13,14-Dihydro-PGD$_2$, 1,9-lactone, a compound according to claim 99.*

*101. A compound according to claim 94, wherein $Y_1$ is trans—CH=CH—.*

*102. PGD$_2$, 1,9-lactone, a compound according to claim 101.*

*103. A compound according to claim 91, wherein $W_2$ is*

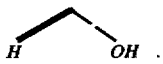

*104. A compound according to claim 103, wherein ~ is α.*

*105. A compound according to claim 104, wherein $M_1$ is*

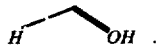

*106. 15-epi-16-Methyl-PGF$_2\alpha$, 1,9-lactone, a compound according to claim 105.*

*107. A compound according to claim 104, wherein $M_1$ is*

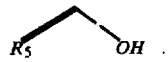

*108. A compound according to claim 107, wherein $Z_1$ is —$CH_2$—O—$CH_2$—$(CH_2)_g$—$CH_2$—.*

*109. 5-Oxa-PGF$_1\alpha$, 1,9-lactone, a compound according to claim 108.*

*110. A compound according to claim 107, wherein $Z_1$ is*

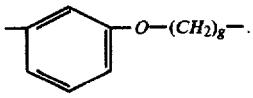

*111. 3-Oxa-3,7-inter-m-phenylene-4,5,6-trinor-PGF$_1\alpha$, 1,9-lactone, a compound according to claim 110.*

*112. A compound according to claim 107, wherein $Z_1$ is*

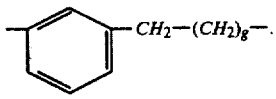

*113. 3,7-inter-m-phenylene-4,5,6-trinor-PGF$_1\alpha$, 1,9-lactone, a compound according to claim 112.*

*114. A compound according to claim 107, wherein $Z_1$ is cis—$CH_2$—CH=CH—$(CH_2)_g$—$CH_2$—.*

*115. cis-4,5-Didehydro-PGF$_1\alpha$, 1,9-lactone, a compound according to claim 114.*

*116. A compound according to claim 107, wherein $Z_1$ is cis—CH=CH—$CH_2$—$(CH_2)_g$—$CF_2$—.*

117. 2,2,16,16-Tetrafluoro-$PGF_{2\alpha}$, 1,9-lactone, a compound according to claim 116. .

118. 2,2-Difluoro-16,16-dimethyl-$PGF_{2\alpha}$, 1,9-lactone, a compound according to claim 116.

119. 2,2-Difluoro-15-methyl-$PGF_{2\alpha}$, 1,9-lactone, a compound according to claim 116.

120. 2,2-Difluoro-$PGF_{2\alpha}$, 1,9-lactone, a compound according to claim 116.

121. A compound according to claim 107, wherein $Z_1$ is $-(CH_2)_3-(CH_2)_g-CF_2-$.

122. 2,2,16,16-Tetrafluoro-$PGF_{1\alpha}$, 1,9-lactone, a compound according to claim 121.

123. 2,2-Difluoro-16,16-dimethyl-$PGF_{1\alpha}$, 1,9-lactone, a compound according to claim 121.

124. 2,2-Difluoro-15-methyl-$PGF_{1\alpha}$, 1,9-lactone, a compound according to claim 121.

125. 2,2-Difluoro-$PGF_{1\alpha}$, 1,9-lactone, a compound according to claim 121.

126. A compound according to claim 107, wherein $Z_1$ is $-(CH_2)_3-(CH_2)_g-CH_2-$.

127. 16,16-Difuoro-$PGF_{1\alpha}$, 1,9-lactone, a compound according to claim 126.

128. 16,16-Dimethyl-$PGF_{1\alpha}$, 1,9-lactone, a compound according to claim 126.

129. 15-Methyl-$PGF_{1\alpha}$, 1,9-lactone, a compound according to claim 126.

130. $PGF_{1\alpha}$, 1,9-lactone, a compound according to claim 126.

131. A compound according to claim 107, wherein $Z_1$ is cis$-CH=CH-CH_2-(CH_2)_g-CH_2-$.

132. A compound according to claim 131, wherein g is 3.

133. A compound according to claim 131, wherein g is one.

134. A compound according to claim 133 wherein $Y_1$ is $-C\equiv C-$.

135. 13,14-Didehydro-$PGF_{2\alpha}$, 1,9-lactone, a compound according to claim 134.

136. A compound according to claim 133, wherein $Y_1$ is cis$-CH=CH-$.

137. cis-13-$PGF_{2\alpha}$, 1,9-lactone, a compound according to claim 136.

138. A compound according to claim 133, wherein $Y_1$ is $-CH_2CH_2-$.

139. 13,14-Dihydro-$PGF_{2\alpha}$, 1,9-lactone, a compound according to claim 138.

140. A compound according to claim 133, wherein $Y_1$ is trans$-CH=CH-$.

141. A compound according to claim 140, wherein $R_7$ is cis$-CH=CH-CH_2-CH_3-$.

142. $PGF_{3\alpha}$, 1,9-lactone, a compound according to claim 141.

143. A compound according to claim 140, wherein $R_7$ is

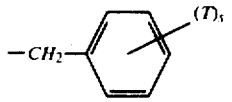

144. A compound according to claim 143, wherein s is zero or one and T is chloro, fluoro, or trifluoromethyl.

145. A compound according to claim 144, wherein $R_5$ is methyl.

146. 15-Methyl-17-phenyl-18,19,20-trinor-$PGF_{2\alpha}$, 1,9-lactone, a compound according to claim 145.

147. A compound according to claim 144, wherein $R_5$ is hydrogen.

148. A compound according to claim 147, wherein at least one of $R_3$ and $R_4$ is fluoro.

149. 16,16-Difluoro-17-phenyl-18,19,20-trinor-$PGF_{2\alpha}$, 1,9-lactone, a compound according to claim 148.

150. A compound according to claim 147, wherein at least one of $R_3$ and $R_4$ is methyl.

151. 16,16-Dimethyl-17-phenyl-18,19,20-trinor-$PGF_{2\alpha}$, 1,9-lactone, a compound according to claim 150.

152. A compound according to claim 147, wherein $R_3$ and $R_4$ are both hydrogen.

153. 17-Phenyl-18,19,20-trinor-$PGF_{2\alpha}$, 1,9-lactone, a compound according to claim 152.

154. A compound according to claim 140, wherein $R_7$ is $-(CH_2)_m-CH_3-$.

155. A compound according to claim 154, wherein m is 3.

156. A compound according to claim 155, wherein $R_5$ is methyl.

157. A compound according to claim 156, wherein at least one of $R_3$ and $R_4$ is fluoro.

158. 15-Methyl-16,16-difuoro-$PGF_{2\alpha}$, 1,9-lactone, a compound according to claim 157.

159. A compound according to claim 156, wherein at least one of $R_3$ and $R_4$ is methyl.

160. 15,16,16-Trimethyl-$PGF_{2\alpha}$, 1,9-lactone, a compound according to claim 159.

161. A compound according to claim 156, wherein $R_3$ and $R_4$ are both hydrogen.

162. 15-Methyl-$PGF_{2\alpha}$, 1,9-lactone, a compound according to claim 161.

163. A compound according to claim 155, wherein $R_5$ is hydrogen.

164. A compound according to claim 163, wherein at least one of $R_3$ and $R_4$ is fluoro.

165. A compound according to claim 164, wherein $R_3$ and $R_4$ are both fluoro.

166. 16,16-Difluoro-$PGF_{2\alpha}$, 1,9-lactone, a compound according to claim 165.

167. A compound according to claim 163, wherein at least one of $R_3$ and $R_4$ is methyl.

168. A compound according to claim 167, wherein $R_3$ and $R_4$ are both methyl.

169. 16,16-Dimethyl-$PGF_{2\alpha}$, 1,9-lactone, a compound according to claim 168.

170. A compound according to claim 163, wherein $R_3$ and $R_4$ are both hydrogen.

171. $PGF_{2\alpha}$, 1,9-lactone, a compound according to claim 170.

172. A prostaglandin-type, 1,9-lactone of the formula

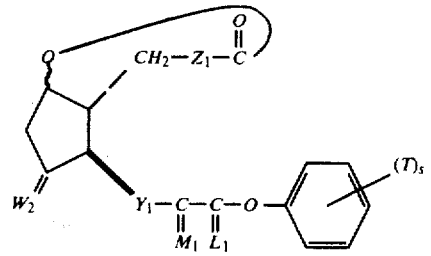

-continued

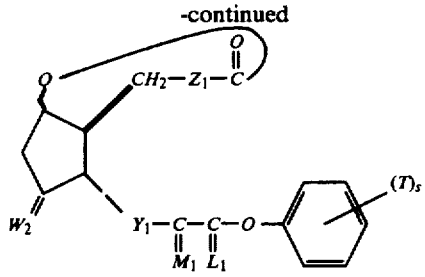

*wherein $W_2$ is*

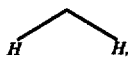

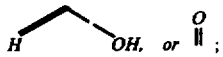

*wherein $L_1$ is*

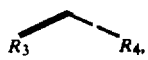

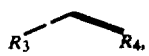

*or a mixture of*

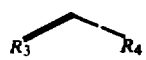

*and*

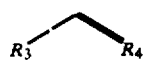

*wherein $R_3$ and $R_4$ are hydrogen or methyl being the same or different;*
*wherein $M_1$ is*

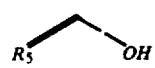

*or*

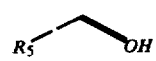

*wherein $R_5$ is hydrogen or methyl*

*wherein T is chloro, fluoro, alkyl of one to 3 carbon atoms, inclusive, or alkoxy of one to 3 carbon atoms, inclusive, the various T's being the same or different, s is zero, one, 2, or 3, with the proviso that not more than two T's are other than alkyl;*

*wherein $Y_1$ is trans—CH=CH—, —$CH_2CH_2$—, cis—CH=CH—, or —C≡C—; and*

*wherein $Z_1$ is* cis—CH=CH—$CH_2$—$(CH_2)_g$—$CH_2$—, (1)

cis—CH=CH—$CH_2$—$(CH_2)_g$—$CF_2$—, (2)

cis—$CH_2$—CH=CH—$(CH_2)_g$—$CH_2$—, (3)

—$(CH_2)_3$—$(CH_2)_g$—$CH_2$—, (4)

—$(CH_2)_3$—$(CH_2)_g$—$CF_2$—, (5)

—$CH_2$—O—$CH_2$—$(CH_2)_g$—$CH_2$—, (6)

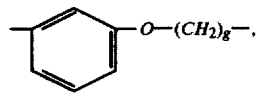
(7)

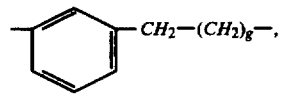
(8)

*wherein g is one to 3, inclusive.*

*173. A compound according to claim 172, wherein $W_2$ is*

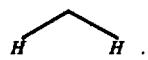

*174. A compound according to claim 172, wherein $W_2$ is*

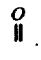

*175. A compound according to claim 174, wherein $Y_1$ is —C≡C—.*

*176. A compound according to claim 174, wherein $Y_1$ is cis—CH=CH—.*

*177. A compound according to claim 174, wherein $Y_1$ is —$CH_2CH_2$—.*

*178. A compound according to claim 174, wherein $Y_1$ is trans—CH=CH—.*

*179. A compound according to claim 172, wherein $W_2$ is*

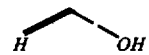

*180. A compound according to claim 179, wherein ~ is α.*

*181. A compound according to claim 180, wherein $M_1$ is*

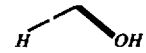

*182. A compound according to claim 180, wherein $M_1$ is*

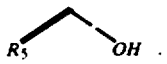

183. A compound according to claim 182, wherein $Z_1$ is $-CH_2-O-CH_2-(CH_2)_g-CH_2-$.

184. A compound according to claim 182, wherein $Z_1$ is

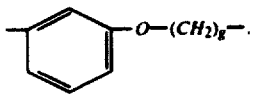

185. A compound according to claim 182, wherein $Z_1$ is

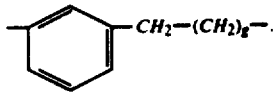

186. A compound according to claim 182, wherein $Z_1$ is cis$-CH_2-CH=CH-(CH_2)_g-CH_2-$.

187. A compound according to claim 182, wherein $Z_1$ is cis$-CH=CH-CH_2-(CH_2)_g-CF_2-$.

188. A compound according to claim 182, wherein $Z_1$ is $-(CH_2)_3-(CH_2)_g-CF_2-$.

189. A compound according to claim 182, wherein $Z_1$ is $-(CH_2)_3-(CH_2)_g-CH_2-$.

190. A compound according to claim 182, wherein $Z_1$ is cis$-CH=CH-CH_2-(CH_2)_g-CH_2-$.

191. A compound according to claim 182, wherein g is 3.

192. A compound according to claim 182, wherein g is one.

193. A compound according to claim 192, wherein $Y_1$ is $-C\equiv C-$.

194. A compound according to claim 192, wherein $Y_1$ is cis$-CH=CH-$.

195. A compound according to claim 192, wherein $Y_1$ is trans$-CH=CH-$.

196. A compound according to claim 192, wherein $Y_1$ is $-CH_2CH_2-$.

197. A compound according to claim 196, wherein s is zero or one and T is chloro, fluoro.

198. A compound according to claim 197, wherein $R_5$ is methyl.

199. 15-Methyl-16-phenoxy-17,18,19,20-tetranor-$PGF_{2\alpha}$, 1,9-lactone, a compound according to claim 198.

200. A compound according to claim 197, wherein $R_5$ is hydrogen.

201. A compound according to claim 200, wherein at least one of $R_3$ and $R_4$ is methyl.

202. 16-Methyl-16-pheoxy-18,19,20-trinor-$PGF_{2\alpha}$, 1,9-lactone, a compound according to claim 201.

203. A compound according to claim 200, wherein $R_3$ and $R_4$ are both hydrogen.

204. 16-Phenoxy-17,18,19,20-tetranor-$PGF_{2\alpha}$, 1,9-lactone, a compound according to claim 203.

* * * * *

UNITED STATES PATENT OFFICE

CERTIFICATE OF CORRECTION

Patent No. Re. 30,053 Dated 24 July 1979

Inventor(s) Gordon L. Bundy

It is certified that error appears in the above-identified patent and that said Letters Patent are hereby corrected as shown below:

Column 186, line 17, "according to claim 196" should read -- according to claim 195 --.

Signed and Sealed this

*Twenty-fifth* Day of *August 1981*

[SEAL]

*Attest:*

GERALD J. MOSSINGHOFF

*Attesting Officer*

*Commissioner of Patents and Trademarks*